(12) United States Patent
Maziarz et al.

(10) Patent No.: US 11,197,889 B2
(45) Date of Patent: *Dec. 14, 2021

(54) IMMUNOMODULATORY PROPERTIES OF MULTIPOTENT ADULT PROGENITOR CELLS AND USES THEREOF

(71) Applicants: ABT Holding Company, Cleveland, OH (US); Oregon Health & Science University, Portland, OR (US)

(72) Inventors: Richard Maziarz, Portland, OR (US); Magdalena Kovacsovics, Portland, OR (US); Philip Streeter, Oregon City, OR (US); Robert Deans, Riverside, CA (US); Wouter Van't Hof, Shaker Hts., OH (US)

(73) Assignees: ABT Holding Company, Cleveland, OH (US); Oregon Health & Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/804,760

(22) Filed: Nov. 6, 2017

(65) Prior Publication Data

US 2018/0055881 A1   Mar. 1, 2018

Related U.S. Application Data

(63) Continuation of application No. 13/345,036, filed on Jan. 6, 2012, now Pat. No. 9,808,485, which is a continuation of application No. 11/269,736, filed on Nov. 9, 2005, now Pat. No. 8,147,824.

(51) Int. Cl.
| | |
|---|---|
| *C12N 5/074* | (2010.01) |
| *A61K 35/12* | (2015.01) |
| *A61K 45/06* | (2006.01) |
| *A61K 35/14* | (2015.01) |
| *A61K 35/28* | (2015.01) |
| *A61N 5/10* | (2006.01) |

(52) U.S. Cl.
CPC ............... *A61K 35/12* (2013.01); *A61K 35/14* (2013.01); *A61K 35/28* (2013.01); *A61K 45/06* (2013.01); *A61N 5/10* (2013.01); *C12N 5/0607* (2013.01); *A61K 2035/122* (2013.01); *A61K 2035/124* (2013.01)

(58) Field of Classification Search
CPC ........ A61K 35/12; A61K 45/06; A61K 35/28; A61K 2035/124; A61K 2035/122; C12N 5/0607
See application file for complete search history.

(56) References Cited

U.S. PATENT DOCUMENTS

| | | |
|---|---|---|
| 4,353,888 A | 10/1982 | Sefton |
| 4,744,933 A | 5/1988 | Rha |
| 4,749,620 A | 6/1988 | Rha |
| 4,814,274 A | 3/1989 | Shioya |
| 5,084,350 A | 1/1992 | Chang |
| 5,089,272 A | 2/1992 | Shioya |
| 5,578,442 A | 11/1996 | Desai |
| 5,639,275 A | 6/1997 | Baetge |
| 5,676,943 A | 10/1997 | Baetge |
| 6,245,781 B1 | 6/2001 | Upadhyay |
| 6,281,012 B1 | 8/2001 | McIntosh |
| 6,306,434 B1 | 10/2001 | Hong |
| 6,328,960 B1 | 12/2001 | McIntosh |
| 6,355,239 B1 | 3/2002 | Bruder |
| 6,368,636 B1 | 4/2002 | McIntosh |
| 6,387,369 B1 | 5/2002 | Pittenger |
| 6,685,936 B2 | 2/2004 | McIntosh |
| 6,797,269 B2 | 9/2004 | Mosca |
| 6,875,430 B2 | 4/2005 | McIntosh et al. |
| 7,015,037 B1 | 3/2006 | Furcht |
| 7,029,666 B2 | 4/2006 | Bruder |
| 7,510,873 B2 | 3/2009 | Mistry |
| 7,514,074 B2 | 4/2009 | Pittenger |
| 7,927,587 B2 | 4/2011 | Blazer |
| 9,808,485 B2 | 11/2017 | Maziarz |
| 11,000,546 B2 | 5/2021 | Deans et al. |
| 2002/0136723 A1 | 9/2002 | Feldmann |
| 2002/0136726 A1 | 9/2002 | Anderson |
| 2004/0037811 A1 | 2/2004 | Penn |
| 2004/0107453 A1 | 6/2004 | Furcht |
| 2006/0008450 A1 | 1/2006 | Verfaillie |
| 2006/0263337 A1 | 11/2006 | Maziarz |
| 2007/0003530 A1 | 1/2007 | Pittenger |
| 2007/0122393 A1 | 5/2007 | McIntosh |
| 2007/0134210 A1 | 6/2007 | Heidaran |
| 2008/0152624 A1 | 6/2008 | Paludan |
| 2008/0226595 A1 | 9/2008 | Edinger |
| 2008/0311084 A1 | 12/2008 | Verfaillie |
| 2008/0317740 A1 | 12/2008 | Blazar |
| 2009/0104163 A1 | 4/2009 | Deans |

(Continued)

FOREIGN PATENT DOCUMENTS

| | | |
|---|---|---|
| EP | 301777 A1 | 2/1989 |
| EP | 2241617 A1 | 10/2010 |

(Continued)

OTHER PUBLICATIONS

Posnett et al. Amplification of autoimmune disease by infection. Arthritis Research & Therapy vol. 7 No 2. p.74-84 (Year: 2005).*

(Continued)

*Primary Examiner* — Taeyoon Kim
(74) *Attorney, Agent, or Firm* — Millen, White, Zelano & Branig; Larry S. Millstein; Jennifer J. Branigan

(57) ABSTRACT

Isolated cells are described that are not embryonic stem cells, not embryonic germ cells, and not germ cells. The cells can differentiate into at least one cell type of each of at least two of the endodermal, ectodermal, and mesodermal lineages. The cells do not provoke a harmful immune response. The cells can modulate immune responses. As an example, the cells can suppress an immune response in a host engendered by allogeneic cells, tissues, and organs. Methods are described for using the cells, by themselves or adjunctively, to treat subjects. For instance, the cells can be used adjunctively for immunosuppression in transplant therapy. Methods for obtaining the cells and compositions for using them also are described.

23 Claims, 8 Drawing Sheets

Specification includes a Sequence Listing.

(56) References Cited

U.S. PATENT DOCUMENTS

| | | |
|---|---|---|
| 2010/0008890 A1 | 1/2010 | Mays |
| 2010/0310570 A1 | 12/2010 | Mays |
| 2012/0121545 A1 | 5/2012 | Kim et al. |
| 2012/0135043 A1 | 5/2012 | Maziarz |
| 2015/0118193 A1 | 4/2015 | Maziarz |

FOREIGN PATENT DOCUMENTS

| | | | |
|---|---|---|---|
| EP | 2377542 | A2 | 10/2011 |
| WO | 9947163 | A2 | 9/1999 |
| WO | 2001011011 | A1 | 2/2001 |
| WO | 2002064748 | A1 | 8/2002 |
| WO | 2003025149 | A1 | 3/2003 |
| WO | 2003059276 | A1 | 7/2003 |
| WO | 2004069172 | A1 | 8/2004 |
| WO | 2004099395 | A1 | 11/2004 |
| WO | 2002056026 | A1 | 6/2005 |
| WO | 2005113748 | A2 | 12/2005 |
| WO | 2006121428 | A1 | 11/2006 |
| WO | 2006121454 | A1 | 11/2006 |
| WO | 07056578 | A1 | 5/2007 |
| WO | 2008019148 | A1 | 2/2008 |

OTHER PUBLICATIONS

Search Report in corresponding EP appl. No. 17200032 dated Jun. 1, 2018.

Lerner, et al., "Stem cell study was flawed, U panel finds," Feb. 2007, pp. 1-4.

Long, et al., "Neural Cell Differentiation in Vitro from Adult Human Bone Marrow Mesenchymal Stem Cells," Stem Cells and Development, 14: 65-69, 2005.

Maitra, et al., "Human mesenchymal stem cells support unrelated donor hematopoietic stem cells and suppress T-cell activation," Bone Marrow Transplantation, 2004, pp. 597-604, vol. 33, Nature Publishing Group.

Menasche, et al., :Skeletal muscle satellite cell transplantation, Cardiovascular Research, 2003, pp. 351-357, vol. 58, Elsevier Science B.V.

Menasche, et al., "Myoblast transplantation for heart failure," The Lancet, Jan. 2001, pp. 279-280, vol. 357, The Lancet Publishing Group.

Miller, et al., "Ex Vivo Culture of CD34/Lin/DR Cells in Stroma-Derived Soluble Factors, Interleukin-3, and Macrophage Inflammatory Protein-1 Maintains Not Only Myeloid But Also Lymphoid Progenitors in a Novel Switch Culture Assay," Blood, Jun. 1998, pp. 4516-4522, The American Society of Hematology.

Moriscot, et al., "Human Bone Marrow Mesenchymal Stem Cells Can Express Insulin and Key Transcription Factors of the Endocrine Pancreas Developmental Pathway upon Genetic and/or Microenvironmental Manipulation in Vitro," Stem Cells, 23: 594-604, 2005.

Motooka Y, et al., Neurogenesis and axonal fiber sprouting following human multipotent adult progenitor cells (MAPC) transplantation in acutely ischemic rats, Neuroscience Meeting Planner [online], 2003, Presentation No. 42.2, [retrieved on Jul. 30, 2012]. Retrieved from the internet.

Myeloproliferative Disorders, 2009, www.labtestsonline.org.au/understanding/conditions/myelopro-disorders-4.html. pp. 1-2.

Nelson et al., Lancet Neural., vol. 2, 2004, pp. 150-158.

Nichols, J. et al., Cell, vol. 95, 1998, pp. 379-391.

Noonan, "Limitations on the Usefullness of Adult Stem Cells," Patent Doc. , Biotech & Pharma Patent Law & News Blog, Mar. 2007, pp. 1-3.

Office Action dated Mar. 18, 2016 for corresponding U.S. Appl. No. 13/954,604.

Office Action dated Mar. 4, 2010 in U.S. Appl. No. 11/269,736 in the name of Richard Maziarz—6 pages.

Orlic, et al., "Transplanted Adult Bone Marrow Cells Repair Myocardial Infarets in Mice," Annals of the New York Academy of Sciences, 2001, pp. 221-230, New York Academy of Sciences.

Oxford online dictionary: definition for "adjunct" p. 1-2. downloaded on Aug. 9, 2013.

Pincock, "Adult stem cell report questioned," The Scientist, Feb. 2007, pp. 1-4.

Pittenger, M. F., Science vol. 284, Apr. 2, 1999.

Prosper, et al., "Phenotypic and Functional Characterization of Long-Term Culture-Initiating Cells Present in Peripheral Blood Progenitor Collections of Normal Donors treated with Granulocyte Colony-Stimulating Factor," Blood, Sep. 1996, pp. 2033-2042, vol. 88, No. 6, The American Society of Hematology.

Punzel, et al., "The Myeloid-Lymphoid Initiating Cell (ML-IC) Assay Assesses the Fate of Multipotent Human Progenitors in Vitro," Blood, Jun. 1999, pp. 3750-3756, vol. 93, No. 11, The American Society of Hematology.

Qi, et al., "Identification of Genes Responsible for Bone Differentiation from Human Bone Marrow Derived Multipotent Adult Stem Cells (MASC) (Abstract)," Gene Expression and Hematopoietic Ste/Progenitor Cell Function, Blood, 2000, pp. 70a-71a, The American Society of Hematology.

Reyes, et al. "Purification and ex vivo expansion of postnatal human marrow mesodemal progenitor cells," Blood, Nov. 2001, pp. 2615-2625, vol. 98, No. 9, The American Society of Hematology.

Reyes, et al., "Characterization of Multipotent Adult Progenitor Cells, a Subpopulation of Mesenchymal Stem Cells," Ann. N.Y. Acad. Sci., 931 (1), pp. 231-235, 2001.

Rice et al., Ann Neurol., vol. 9, 1981, pp. 131-141.

Rodriguez et al. Transplantation of a multipotent cell population from human adipose tissue induces dystrophin expression in the immunocompetent mdx mouse. JEM vol. 201, May 2, 2005. p. 1397-1405.

Rosfjord, E., Rizzino, A., Biochem Biophys Res Commun, vol. 203, 1997, pp. 1795-1802.

Ryan, et al., "Mesenchymal stem cells avoid allogeneic rejection," Journal of Inflammation, Jul. 2005, pp. 1-11, vol. 2, No. 8, BioMed Central.

Sakai, et al., "Fetal Cell Transplantation: A Comparison of Three Cell Types," The Journal of Thoracic and Cardiovascular Surgery, Oct. 1999, pp. 715-725, vol. 118, No. 4, Mosby, Inc.

Schwartz, et al., "Multipotent adult progenitor cells from bone marrow differentiate into functional heatocyte-like cells," The Journal of Clinical Investigation, May 2002, pp, 1291-1302, vol. 109, No, 10, American Society of Sciences.

Serafini, et al., Hematopoietic reconstitution by multipotent adult progenitor cells: precursons to long-term hematopoietic stem cells, : The Journal of Experimental Medicine, Jan. 2007, pp. 1-11, Correction to Serafini et al., J. Exp. Med., vol. 204, No. 1, Jan. 2007, pp. 129-139, The Rockefeller University Press.

Serup et al. Islet and stem cell transplantation for treating diabetes. BMJ 2001;322:29-32.

Shankaran et al, Nengl Jmed., vol. 353, 2005, pp. 1574-1584.

Shimozaki et al., Development, vol. 130, 2003, pp. 2505-2512l.

Sigurjonsson, et al., "Adult human hematopoietic stem cells produce neurons efficiently in the regenerating chicken embryo spinal cord," PNAS, Apr. 2005, pp. 5227-5232, vol. 102, No. 14, The National Academy of Sciences of the USA.

Sohn, et al., "Stem cell therapy for muscular dystrophy," Expert Opin., Biol. Ther., 2004, pp. 1-9, vol. 4, No. 1, Ashley Publications Ltd.

Tomita, et al., "Autologous Transplantation of Bone Marrow Cells Improves Damaged Heart Function," Circulation, 1999, pp. II-247-II-256, American Heart Association, Inc.; Supplement to Circulation, Journal of the American Heart Association, 1998, vol. 100, No. 19.

Tse, et al., "Suppression of Allogeneic T-cell Proliferation by Human Marrow Stomal Cells: Implications in Transplantation," Transplantation, Feb. 2003, pp. 389-397, vol. 75, No. 3, Lippincott Williams & Wilkins, Inc.

Urtizberea, "Therapies in Muscular Dystrophy: Current Concepts and Future Prospects," European Neurology, 2000, pp. 127-132, vol. 43, S. Karger AG.

(56) References Cited

OTHER PUBLICATIONS

US 7,700,089, 04/2010, Messina et al. (withdrawn).
Verfaillie, "Letter to the Editor," International Society for Experimental Hematology, 2007, p. 1, Elsevier.
Volpe: "Neurology of the Newborn", 2001, W.B. Saunders.
Xu L, et al., Intrastriatal transplantation of cryopreserved human bone marrow-derived multipotent adult progenitor cells at seven days after experimental ischemic stroke exerts dose-dependent behavioral recovery, Experimental Neurology, May 2005, vol. 193, No. 1, p. 265.
Yasuhara, et al., "Transplantation of Cryopreserved Human Bone Marrow-derived Multipotent Adult Progenitor Cells for Neonatal Hypoxic-Ischemic Injury: Targeting the Hippocampus," Reviews in the Neurosciences, 2006, pp. 215-225, vol. 17, No. 1-2, Freund & Pettman, U.K.
Zhao, Robert C., et al., "Mechanisms of and perspectives on the mesenchymal stem cell in Immunotherapy," Journal of Laboratory and Clinical Medicine, May 23, 2008, No. 6827673289, pp. 2-9.
Zhao, Robert Chunhua et al. "Mechanisms of and perspectives on the mesenchymal stem cell in Immunotherapy." Journal of Laboratory and Clinical Medicine. May 23, 2008. No. 6827673289, p. 2-9.
Zuk. Adipose-Derived Stem Cells in Tissue Regeneration: A Review. ISRN Stem Cells 2013, Article ID 713959, p. 1-35.
J. Urtizberea, "Therapies in Muscular Dystrophy: Current Concepts and Future Prospects," European Neurology, 2000, pp. 127-132, vol. 43, S. Karger AG. DOI:10.1159/000008150.
Notice of Allowance in co-pending U.S. Appl. No. 12/093,159 dated Feb. 22, 2018 (pp. 1-10).
Corrected Notice of Allowance in copending U.S. Appl. No. 12/093,159 dated Mar. 13, 2018 (pp. 1-6).
Remington's Pharmaceutical Science, 1985.
Abraham et al. Human Pancreatic Islet-Derived Progenitor Cell Engraftment in Immunocompetent Mice. Am J Pathol 2004, 164:817-830.
Aldous, et al., "Flawed stem cell data withdrawn," New Scientist, Feb. 2007, pp. 1-2.
Aldous, et al., "Fresh questions on stem cell findings," New Scientist, Mar. 2007, pp. 12-13, vol. 12.
Atkinson. Thirty Years of Investigating the Autoimmune Basis for Type 1 Diabetes Why Can't We Prevent or Reverse This Disease? Diabetes 54:1253-1263, 2005.
Barker, Ann Med., vol. 31, No. 1, 1999, pp. 3-6.
Barry, Frank P., and J. Mary Murphy. "Mesenchymal stem cells: Clinical applications and biological characterization." The International Journal of Biochemistry & Cell Biology. 2004, 36, p. 568-584.
Bartholomew et al., "Mesenchymal stem cells suppress lymphocyte proliferation in vitro and prolong skin graft survival in vivo," Int'l Society for Experimental Hematology, 2002, pp. 42-48, vol. 30, Elsevier Science Inc.
Ben-Shushan, E. et al., Cell Biol, vol. 18, 1998, pp. 1866-1878.
Bone Marrow Transplantation and Peripheral Blood Stem Cell Transplanation, NCI Factsheet, National Cancer Institute, www.cancer.gov/cancertopics/factsheet/Therapy/bone-marrowtransplant. pp. 1-15, 2010.
Borlongan et al. J neuro sci. vol. 15, 1995, pp. 5372-5378.
Carroll Je, et al., Intracerebral grafts of cryopreserved syngeneic and allogeneic rat bone marrow-derived multipotent adult progenitor cells promote behavioral recovery in neonatal rats exposed to hypoxic-ischemic injury, Experimental Neurology, May 2005, vol. 193, No. 1, p. 241.
Check, "Stem-cell paper corrected," Nature, 2007, p. 1, Nature Publishing Group.
Chi, "Adult stem cell figure retracted," The Scientist, Jun. 2007, pp. 1-5, Nature Publishing Group.
Cutler, et al., "Peripheral Blood Stem Cells for Allogeneic Transplantation: A Review," Stem Cells, 2001, pp. 108-117, vol. 19, AlphaMed Press.

Database Biosis, No. XP002427848, PREV200600133636, Blood, No. 2005, pp. 390B-291B, vol. 106, No. 11, Part 2, The American Society of Hematology.
Decision on Motions—USPTO, TTAB Interference No. 105, 953 SGL, Ho et al. v. Furcht et al, dated Sep. 26, 2014.
Di Nicola, et al., "Human bone marrow stromal cells suppress T-lymphocyte proliferation induced by cellular or nonspecific mitogenic stimuli," Blood, 2002, pp. 3838-3843, vol. 99, No. 10, The American Society of Hematology.
Donovan, et al., "The end of the beginning for pluripotent stem cells," Nature, Nov. 2001, pp. 92-97, vol. 414, Macmillan Magazines Ltd.
English language translation of Japanese Office Action dated Aug. 11, 2015 for corresponding Japanese Application No. 2013-150313.
Farag, "Chronic graft-versus host disease: where do we go from here?," Bone Marrow Transplantation, 2004, pp. 569-577, vol. 33, Nature Publishing Group.
First Redeclaration—USPTO, TTAB Interference No. 105, 953 SGL, Ho et al. v. Furcht et al, dated Sep. 26, 2014.
Frassioni, et al., "Expanded mesenchymal stem cells (MSC), confused with HLA identical hemopoietic stem cell transplants, reduce acute and chronic graft versus host disease: A matched pair analysis," Bone Marrow Transplantation, 2002, p. S2, vol. 29, No. Suppl. 2, XP002424218, Abstract 75, Nature Publishing Group.
Game, et a., "Rejection mechanisms in transplantation," Wiener Klinische Wochernschrift, 2001, pp. 832-838, vol. 1, 113/20-21.
Glenn, "Paper on Versatility of Adult Stem Cells Under Question," The Chronicle, Feb. 2007, pp. 1-4.
Gussoni, et al., "Dystrophin expression in the mdx mouse restored by stem cell transplantation," Nature, Sep. 1999, pp. 390-394, vol. 401, Macmillan Magazines Ltd.
Heinonn et al., Bjog, vol. 109, 2002, pp. 261-264.
Huang et al. Spheroid formation of mesenchymal stem cells on chitosan and chitosan-hyaluronan membranes. Biomaterials 32 (2011) 6929e6945.
Hughes, "Cardiac stem cells," Journal of Pathology, 2002, pp. 468-478, vol. 197, John Wiley Y Sons, Ltd.
Izadpanah, et al., "Biologic Properties of Mesenchymal Stem Cells Derived From Bone Marrow and Adipose Tissue," Journal of Cellular Biochemistry, 99: 1285-1297, 2006.
Jackowski, British Journal of Neurosurgery 9: 303-317 (1995).
Japanese Office Action dated Aug. 11, 2015 for corresponding Japanese Application No. 2013-150313.
Jiang, et al., "Multipotent progenitor cells can be isolated from postnatal murine bone morrow, muscle, and brain," Experimental Hematology, Apr. 2002, pp. 896-904, vol. 30, Elsevier Science Inc.
Jiang, et al., "Pluripotency of Mesenchymal stem cells derived form adult marrow," Nature, Jul. 2002, pp. 41-49, vol. 418, Nature Publishng Group.
Jiang, et al., "Pluripotency of mesenchymal stem cells derived from adult marrow," (Corrections and Amendments), Nature, Jun. 2007, pp. 879-880, vol. 447, Nature Publishing Group.
Jiao et al., "Long-term correction of rat model of Parkinson's disease by gene therapy," Nature, Apr. 1993, pp. 450-453, vol. 362, Nature Publishing Group.
Jorgensen, et al., "Engineering mesenchymal stem cells for immunotherapy," Gene Therapy, 2003, pp. 928-931, vol. 10, Nature Publishing Group.
Judgment—USPTO, TTAB Interference No. 105, 953 SGL, Ho et al. . Furcht et al, dated Sep. 26, 2014.
Keene, et al., "Phenotypic Expression of Transplanted Human Bone Marrow-Derived Multipotent Adult Stem Cells into the Rat CNS," ASNTR Platform Session Abstracts, Apr. 2000, pp. 439, 465, Academic Press.
Kessler, et al., "Myoblast Cell Grafting Into Heart Muscle: Cellular Biology and Potential Applications," Annu. Rev. Physiol. 1999, pp. 219-242, vol. 61, Annual Reviews.
Klug, et al., "Genetically Selected Cardiomyocytes from Differentiating Embryonic Stem Cells Form Stable Intracardiac Grafts," J. Clin. Invest., Jul. 1996, pp. 216-224, vol. 98, No. 1, American Society for Clinical Investigation, Inc.

(56) References Cited

OTHER PUBLICATIONS

Kocher, et al., "Neovacularization of ischemic myocardium by human bone-marrow-derived angioblasts prevents cardiomyocyte apoptosis, reduces remodeling and improves cardiac function," Nature Medicine, Apr. 2001, pp. 430-436, vol. 7, No. 4, Nature Publishing Group.

Koh, et al., "Differentiationand Long-Term Survival of C2C12 Myoblast Grafts in Heart," J. Clin. Invest. Sep. 1993, pp. 1548-1554, vol. 92, American Society for Clinical Investigation, Inc.

Kopen, et al., "Marrow stromal cells migrate throughout forebrain and cerebellum, and they differentiate into astrocytes after injection into neonatal mouse brains," Cell Biology, Sep. 1999, pp. 10711-10716, vol. 96, Proc. Nat'l Acad. Sci. USA.

Kovacsovics-Bankowski, et al., "Multi-stem™ (multipotent adult progenitor cells) are non-immunogenic and display immunosuppressive properties on activated T cells," 12th Annual Meeting of the Int'l Society for Cellular Therapy, 2006, vol. 8, No. Suppl. 1, XP08076051, Abstract 166, Taylor & Francis healthsciences.

Krause, et al., "Multi-Organ, Multi-Lineage Engraftment by a Single Bone Marrow-Derived Stem Cell," Cell, May 2001, pp. 369-377, Bol. 105, Cell Press.

Lagasse, et al., "Purified hematopoietic stem cells can differentiate into hepatocytes invio," Nature Medicine, Nov. 2000, pp. 1229-1234, vol. 6, No. 11, Nature American Inc.

Le Blanc et al., "Treatment of severe acute graft-versus-host disease with third party haploidentical mesenchymal stem cells," Research Letters, May 2004, pp. 1439-1441, vol. 363, The Lancet.

Le Blanc, "Immunomodulatory effects of fetal and adult mesenchymal stem cells," International Society for Cellular Therapy, Cythotherapy 2003, pp. 485-489, vol. 5, No. 6, Taylor & Francis healthsciences.

Le Blanc, et al., "Mesenchymal Stem Cells Inhibit and Stimulate Mixed Lymphocyte Cultures and Mitogenic Response-Independently of the Major Histocompatibility Complex," Scandinavian Journal of Immunology, 2003, pp. 11-20, vol. 57, Blackwell Publishing Ltd.

Office Action in corresponding China application No. 201510185968.0 dated May 10, 2018 (pp. 1-14).

Tropel et al.: Isolation and characterisation of mesenchymal stem cells from adult mouse bone marrow; Exp Cell Res. May 1, 2004;295(2):395-406. (english abstract).

Okuda T : Oct-3/4 repression accelerates differentiation of neural progenitor cells in vitro and in vivo.: Brain Res Mol Brain Res. Dec. 6, 2004;132(1):18-30. (english abstract).

Wang-Xiao et al: reference "Study on Isolated Culture of Human Bone Marrow Pluripotent Adult Progenitor Cells and Differentiation toward Hepatocyte like Cells" Clin J Gasto Hepa, Apr. 2003 (vol. 12 No. 2). (english absract).

Ong, Shin-Yeu et al: "Hepatic Differentiation Potential of Commercially Available Human Mesenchymal Stem Cells" Tissue Engineering— vol. 12, No. 12, Oct. 2006 (pp. 3477-3485).

Jia Yanjie et al; Effects of Notch-1 signalling pathway on differentiation of marrow mesenchymal stem cells into neurons in vitro ;NeuroReport. 18(14):1443-1447, Sep. 2007.

Karaöz E; A comprehensive characterization study of human bone marrow mscs with an emphasis on molecular and ultrastructural properties: J Cell Physiol. May 2011;226(5):1367-82.

Jiang, Wenqi, et al., Cancer Biotherapy, Guangzhou Science & Technology Press, Chapter 6 Stem Cell Therapy, Section 2 Mesenchymal Stem Cells, Apr. 1, 2006, China (With English Translation Attached). pp. 1-9.

Liu, Bin, Editor, Histology and Embryology, 1st Ed., Chap. 5(IV) Blood and Hemopoiesis, Peking University Medical Press, May 2005, China (With English Translation Attached). pp. 1-7.

Pei, Xuetao, Editor, Stem Cell Biology, 1st Ed., 17.2.2 Mesenchymal Stem Cells (MSCs), Jul. 2003, China (With English Translation Attached). pp. 1-17.

Li, Jingyuan et al., Telomerase Activity of Human Bone Marrow Mesenchymal Stem Cells, J. Zhejiang Univ. (Med Sci) 2004 Nov. 2004, 33(6):481-485, China. pp. 1-5.

Office Action in corresponding CN appln. 201810210598.5 dated Dec. 23, 2020 (pp. 1-7) and Search report (pp. 1-4).

Yasuhara T et al: Transplantation of cryopreserved human bone marrow-derived multipotent adult progenitor cells for neonatal hypoxic-ischemic injury: targeting the hippocampus .,Reviews in The Neurosciences,vol. 17, No. 1-2, 2006, pp. 215-225, XP008075910, ISSN: 0334-1763.

Supplemental Search Report in corresponding EP120195663.8 dated Mar. 18, 2021 (pp. 1-11).

Van Raemdonck, Dirk et al., (2013). "Machine perfusion in organ transplantation", Current Opinion in Organ Transplantation, 18(1), 24-33.

Liu, L. et al. Telomerase deficiency impairs differentiation of mesenchymal stem cells. Exp Cell Res, 294(1), 1-8. (Abst).

Examination report in corresponding New Zealand application 714064 dated Mar. 25, 2021 (pp. 1-8).

\* cited by examiner

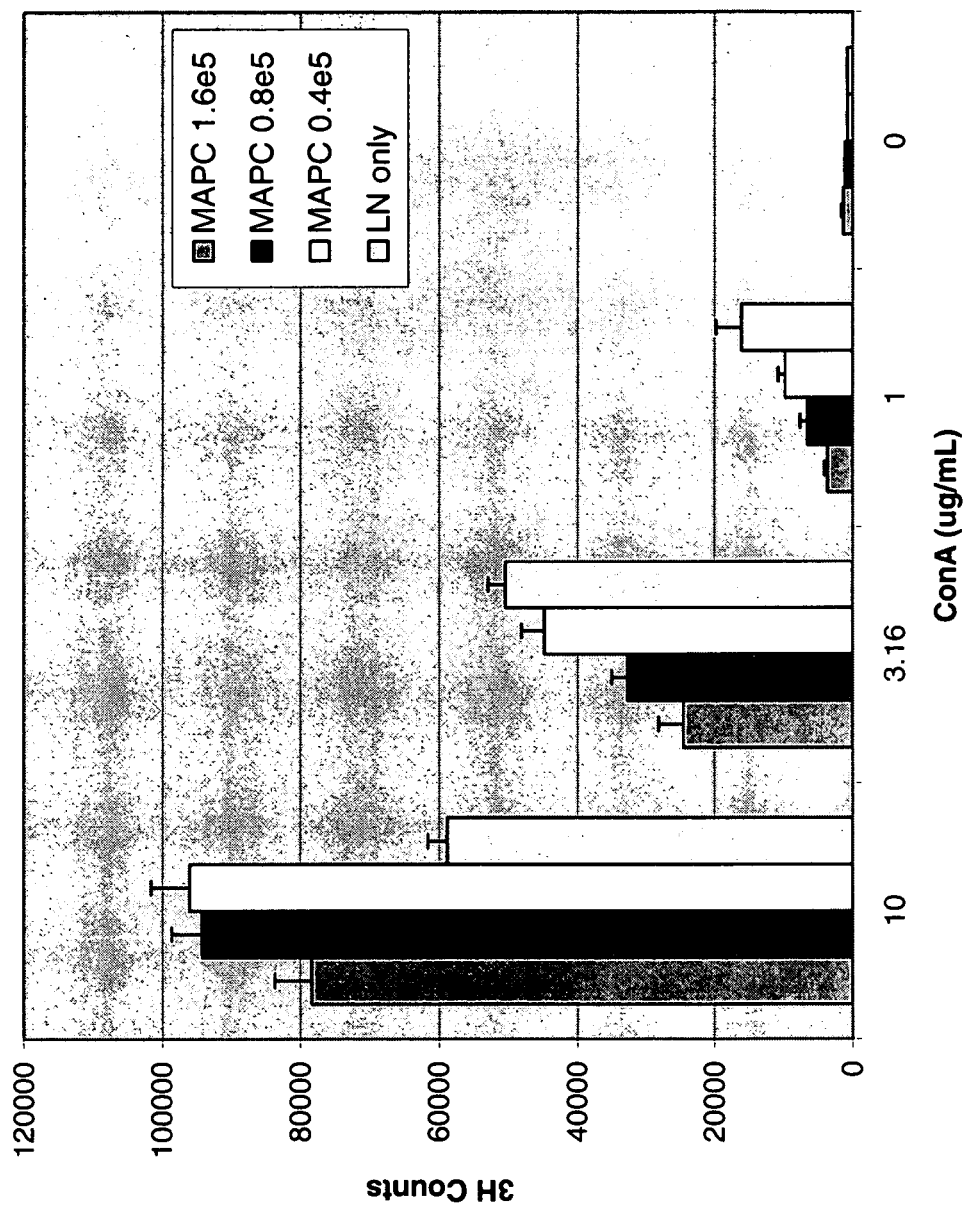

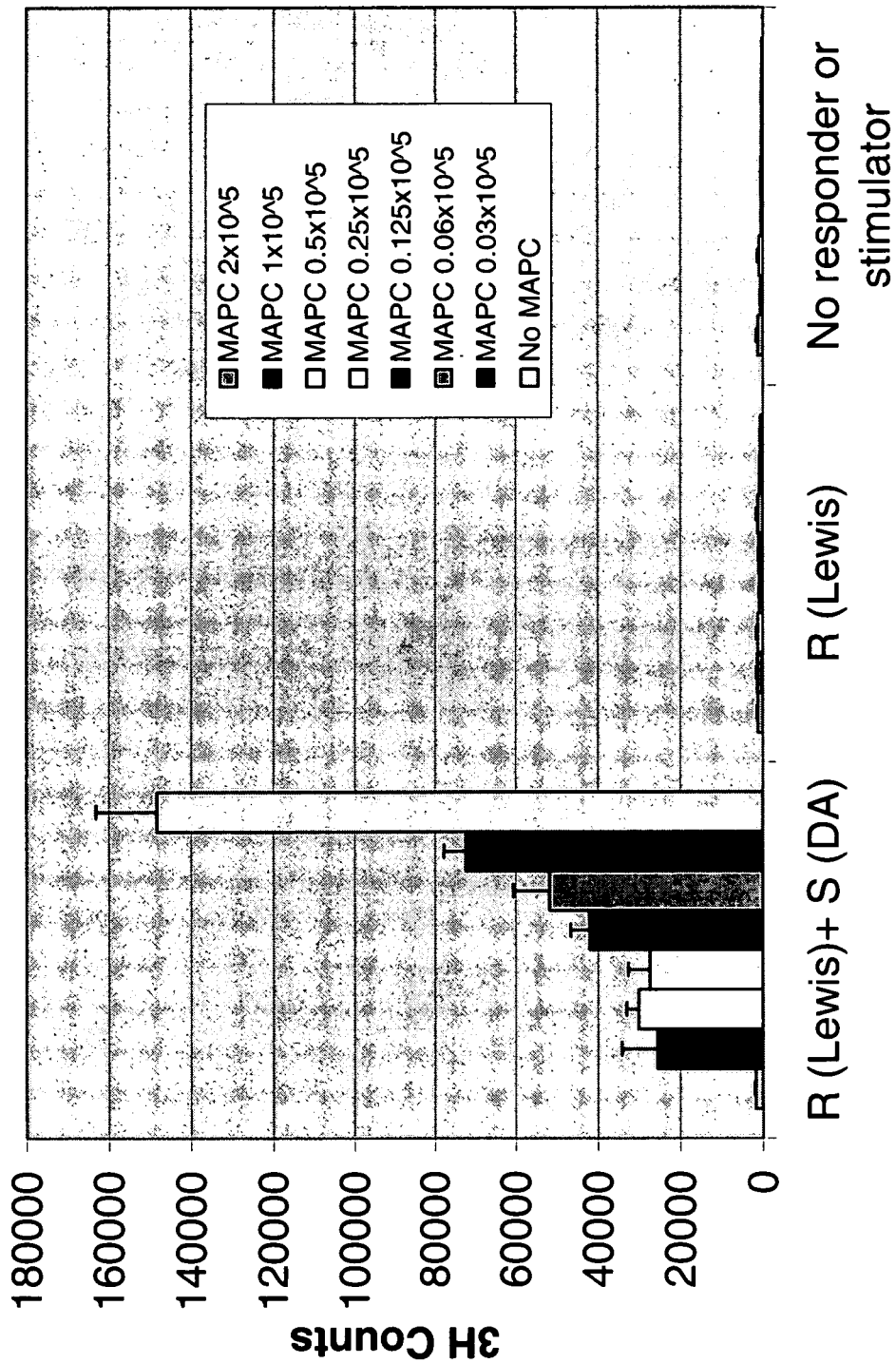

SEQUENCE LISTING

<160> NUMBER OF SEQ ID NOS: 12

<210> SEQ ID NO 1
<211> LENGTH: 19
<212> TYPE: DNA
<213> ORGANISM: Mus musculus

<400> SEQUENCE: 1
tggattgcac gcaggttct                                                 19

<210> SEQ ID NO 2
<211> LENGTH: 19
<212> TYPE: DNA
<213> ORGANISM: Mus musculus

<400> SEQUENCE: 2
ttcgcttggt ggtcgaatg                                                 19

<210> SEQ ID NO 3
<211> LENGTH: 20
<212> TYPE: DNA
<213> ORGANISM: Mus musculus

-continued

```
<400> SEQUENCE: 3
gaagcgtttc tccctggatt                                              20

<210> SEQ ID NO 4
<211> LENGTH: 19
<212> TYPE: DNA
<213> ORGANISM: Mus musculus

<400> SEQUENCE: 4
gtgtaggatt gggtgcgtt                                               19

<210> SEQ ID NO 5
<211> LENGTH: 22
<212> TYPE: DNA
<213> ORGANISM: Mus musculus

<400> SEQUENCE: 5
gaagcgttct ccctggaatt tc                                           22

<210> SEQ ID NO 6
<211> LENGTH: 20
<212> TYPE: DNA
<213> ORGANISM: Mus musculus

<400> SEQUENCE: 6
gtgtaggatt gggtgcgttt                                              20

<210> SEQ ID NO 7
<211> LENGTH: 22
<212> TYPE: DNA
<213> ORGANISM: Mus musculus

<400> SEQUENCE: 7
gctgttcgca aagactcgct ac                                           22

<210> SEQ ID NO 8
<211> LENGTH: 24
<212> TYPE: DNA
<213> ORGANISM: Mus musculus

<400> SEQUENCE: 8
atggctctgg cactgatacg gatg                                         24

<210> SEQ ID NO 9
<211> LENGTH: 25
<212> TYPE: DNA
<213> ORGANISM: Mus musculus

<400> SEQUENCE: 9
ccatgaccta tactcaggct tcagg                                        25

<210> SEQ ID NO 10
<211> LENGTH: 26
<212> TYPE: DNA
<213> ORGANISM: Mus musculus

<400> SEQUENCE: 10
gaagctccat atccctgggt ggaaag                                       26

<210> SEQ ID NO 11
<211> LENGTH: 20
<212> TYPE: DNA
<213> ORGANISM: Mus musculus
```

```
<400> SEQUENCE: 11
ggagtgtcgc ttagaggtgc                                               20

<210> SEQ ID NO 12
<211> LENGTH: 20
<212> TYPE: DNA
<213> ORGANISM: Mus musculus

<400> SEQUENCE: 12
tccagaaagc caagagaagc                                               20
```

IMMUNOMODULATORY PROPERTIES OF MULTIPOTENT ADULT PROGENITOR CELLS AND USES THEREOF

REFERENCE TO RELATED APPLICATIONS

This application is a continuation of U.S. application Ser. No. 13/345,036 filed Jan. 6, 2012, which is a continuation of U.S. application Ser. No. 11/269,736 filed 9 Nov. 2005.

STATEMENT OF GOVERNMENT RIGHTS

Not Applicable.

FIELD OF THE INVENTION

The field of the invention is immunomodulation by multipotent adult progenitor cells ("MAPCs") and their use for modulating immune responses in primary and adjunctive therapies.

BACKGROUND OF THE INVENTION

The therapeutic use of organ transplants, including bone marrow transplants, has steadily increased since its early beginnings. It has become an important therapeutic option for a number of diseases, including, but not limited to, hematologic, immunologic, and malignant disorders.

Unfortunately, the therapeutic uses of transplantation often are complicated, rendered ineffectual, or precluded by adverse immune responses engendered by the transplant. Among the most prominent adverse reactions encountered as a result of transplant therapies are (i) the host versus graft response ("HVG") (rejection of the transplant by an immune competent host), and (ii) graft versus host disease ("GVHD") (processes that occur primarily in an immunocompromised host when it is recognized as non-self by immunocompetent cells of a graft).

Graft rejection in a host can be avoided, of course, by perfectly matching the donor and the host. Except for autologous tissue, however, only identical twins might be expected to be truly syngeneic. Perfect matches between an individual donor and another individual host/recipient are virtually non-existent. Thus, the use of autologous tissue is the only other way to make a perfect match. Unfortunately, the host tissue is typically not suitable or was not isolated in advance of need. Frequently the need for the transplant therapy is, in fact, to replace damaged tissue in the host. The use of syngeneic tissue, therefore, while an effective solution to the problems of adverse host response to graft tissue, is not generally useful in practical applications.

If syngeneic matching is not possible, the adverse immune effects that arise in transplant therapies can be mitigated by matching an allogeneic donor and host as closely as possible. Blood and/or tissue typing is used to match donors and hosts to provide the highest likelihood of therapeutic success. Even the closest matching of allogeneic tissue, however, does not prevent serious HVG, and, accordingly, transplant therapies involve the use of immunosuppression and immunosuppressive drugs, as discussed below.

Another approach to avoid the complications of HVG in transplant therapies has been to disable the immune system of the recipient host. This has been accomplished by using radiation therapy, and/or immunosuppressive chemotherapy, and/or antibody therapy. The resulting suppression of host immune responses often quite effectively aids establishment of the graft (such as bone marrow) in the host. However, immunoablation or suppression compromises the host's immune defenses. This results in the host becoming all too readily susceptible to infections after even minor exposure to infectious agents. The resulting infections are a major cause of morbidity and mortality among transplant patients.

Compromising the host immune system also engenders or exacerbates another serious problem encountered in transplant therapies—graft versus host disease ("GVHD"). GVHD occurs when donor tissue contains immunocompetent cells that recognize MHC proteins of the recipient as non-self. This activates the T-cells, and they secrete cytokines, such as IL-2 (interleukin 2), IFN-γ (interferon γ), and TNF-α (tumor necrosis factor α). These signals trigger an immune attack on recipient targets including the skin, GI tract, liver, and lymphoid organs (Ferrara and Deeg, 1991). GVHD is particularly a problem in bone marrow transplants, where it has been shown to be mediated primarily by T lymphocytes (Grebe and Streilein, 1976). In fact, approximately 50% of bone marrow transplant patients develop acute GVHD. Many of these patients die (from 15% to 45%).

There are also other immune system dysfunctions, disorders, and diseases that arise as primary pathologies and as secondary effects of other pathologies and/or treatments thereof. These include neoplasms, pathologies of the bone marrow, pathologies of the blood, autoimmune disorders, and some inflammatory disorders, as discussed further below. Primary and adjunctive therapy for these disorders and diseases, like primary and adjunctive therapies for HVG and GVHD, often involve the use of immunosuppressive drugs. All of the current therapies have disadvantages and side effects.

Immunosuppressant Drugs

A good deal of effort has been directed to developing drugs to treat these immune system dysfunctions to ameliorate or eliminate their deleterious effects, without causing additional harmful side effects. There has been some progress toward this goal, and a number of drugs have been developed and are in use to prevent and/or treat these dysfunctions. The introduction of the more effective of these drugs marked a great advance in the medical practice of transplant therapies; but, none are ideal. Indeed, none of the immunosuppressive drugs currently available for clinical use in transplant therapies are entirely effective. All of the drugs have serious drawbacks and deleterious side effects, as summarized briefly below. For review see Farag (2004), "Chronic graft-versus-host disease: where do we go from here?," *Bone Marrow Transplantation* 33: 569-577.

Corticosteroids, which are used primarily to treat inflammation and inflammatory diseases, are known to be immunosuppressive and are considered by many to be the best primary treatment for HVG and GVHD. They inhibit T-cell proliferation and T-cell dependent immune responses, at least in part, by inhibiting the expression of certain cytokine genes involved in T-cell activation and T-cell dependent immune response.

Cyclosporin is among the most frequently used drugs for immune suppression and the prevention of HVG and GVHD. It is strongly immunosuppressive in general. Although it can be effective in reducing adverse immune reactions in transplant patients, it also weakens the immune system so much that patients are left highly vulnerable to infections. Consequently, patients are much more easily infected by exposure pathogens, and have little capacity to mount an effective immune response to infections. Even mild pathogens then can be life-threatening. Cyclosporin also causes a variety of other undesirable side effects.

Methotrexate is also widely used in the prophylaxis and treatment of HVG and GVHD, by itself or in combination with other drugs. Studies have shown that, if it is effective at all, it is apparently less effective than cyclosporin. As with cyclosporin, methotrexate causes a variety of side effects, some of which can be deleterious to patient health.

FK-506 is a macrolide-like compound. Similar to cyclosporin, it is derived from fungal sources. The immunosuppressive effects of cyclosporin and FK-506 are similar. They block early events of T-cell activation by forming a heterodimeric complex with their respective cytoplasmic receptor proteins (i.e., cyclophilin and FK-binding protein). This then inhibits the phosphatase activity of calcineurin, thereby ultimately inhibiting the expression of nuclear regulatory proteins and T-cell activation genes.

Other drugs that have been used for immunosuppression include antithymocyte globulin, azathioprine, and cyclophosphamide. They have not proven to be advantageous. Rapamycin, another macrolide-like compound which interferes with the response of T-cells to IL-2, also has been used to block T-cell activated immune response. RS-61443, a derivative of mycophenolic acid, has been found to inhibit allograft rejection in experimental animals. Mizoribine, an imidazole nucleoside, blocks the purine biosynthetic pathway and inhibits mitogen stimulated T- and B-cell proliferation in a manner similar to azathioprine and RS-61443. Deoxyspergualin, a synthetic analog of spergualin, has been found to exert immunosuppressive properties in pre-clinical transplantation models. The anti-metabolite brequinar sodium is an inhibitor of dihydro-orotate dehydrogenase and blocks formation of the nucleotides uridine and cytidine via inhibition of pyrimidine synthesis. Berberine and its pharmacologically tolerable salts have been used as an immunosuppressant for treating autoimmune diseases such as rheumatism, for treating allergies, and for preventing graft rejection. It has been reported that berberine inhibits B-cell antibody production and generally suppresses humoral immune responses, but does not affect T-cell propagation. See Japanese Patent 07-316051 and U.S. Pat. No. 6,245,781.

None of these immunosuppressive drugs, whether used alone or in combination with other agents, are fully effective. All of them generally leave patients still susceptible to HVG and GVHD and weaken their ability to defend against infection. This renders them much more susceptible to infection and much less able to fight off infections when they do occur. Furthermore, all of these drugs cause serious side effects, including, for instance, gastrointestinal toxicity, nephrotoxicity, hypertension, myelosuppression, hepatotoxicity, hypertension, and gum hypertrophy, among others. None of them have proven to be a fully acceptable or effective treatment. In sum, given these drawbacks, there is at present no entirely satisfactory pharmaceutically based treatment for adverse immune system dysfunction and/or responses such as HVG and GVHD.

It has long been thought that a more specific type of immune suppression might be developed without these drawbacks. For example, an agent that suppressed or eliminated alloreactive T-cells, specifically, would be effective against HVG and GVHD (at least for allogeneic grafts) without the deleterious side effects that occur with agents that globally attack and compromise the immune system. However, as yet, no such agent(s) have been developed.

Use of Restricted Stem Cells in Transplantation

The use of stem cells in lieu of or together with immunosuppressive agents has recently attracted interest. There have been some encouraging observations in this area. A variety of stem cells have been isolated and characterized in recent years. They range from those of highly restricted differentiation potential and limited ability to grow in culture to those with apparently unrestricted differentiation potential and unlimited ability to grow in culture. The former have generally been the easier to derive and can be obtained from a variety of adult tissues. The latter have had to be derived from adult germ cells and embryos, and are called embryonal stem ("ES") cells, embryonal germ ("EG") cells, and germ cells. Stem cells derived from adult tissue have been of limited value because they are immunogenic, have limited differentiation potential, and have limited ability to propagate in culture. ES, EG, and germ cells do not suffer from these disadvantages, but they have a marked propensity to form teratomas in allogeneic hosts, raising due concern for their use in medical treatments. For this reason, there is pessimism about their utility in clinical applications, despite their advantageously broad differentiation potential. Stem cells derived from embryos also are subject to ethical controversies that may impede their use in treating disease.

Some efforts to find an alternative to ES, EG, and germ cells have focused on cells derived from adult tissue. While adult stem cells have been identified in most tissues of mammals, their differentiation potential is restricted and considerably more narrow than that of ES, EG, and germ cells. Indeed many such cells can give rise only to one or a few differentiated cell types, and many others are restricted to a single embryonic lineage.

For instance, hematopoietic stem cells, which can be isolated from bone marrow, blood, cord blood, fetal liver, and yolk sac, can reinitiate hematopoiesis and generate multiple hematopoietic lineages. Thus, they can repopulate the erythroid, neutrophil-macrophage, megakaryocyte, and lymphoid hemopoietic cell pools. However, they can differentiate only to form cells of the hematopoietic lineage. They cannot provide cells of any other lineages.

Neural stem cells were initially identified in the subventricular zone and the olfactory bulb of fetal brain. Studies in rodents, non-human primates, and humans have shown that neural stem cells continue to be present in adult brain. These stem cells can proliferate in vivo and continuously regenerate at least some neuronal cells in vivo. When cultured ex vivo, neural stem cells can be induced to proliferate, as well as to differentiate, into different types of neurons and glial cells. When transplanted into the brain, neural stem cells can engraft and generate neural cells and glial cells. Neural stem cells cannot differentiate into cells that are not of neuroectodermal origin.

Mesenchymal stem cells ("MSCs") originally were derived from the embryonal mesoderm and subsequently have been isolated from adult bone marrow and other adult tissues. They can be differentiated to form muscle, bone, cartilage, fat, marrow stroma, and tendon. Mesoderm also differentiates into visceral mesoderm which can give rise to cardiac muscle, smooth muscle, or blood islands consisting of endothelium and hematopoietic progenitor cells. The differentiation potential of the mesenchymal stem cells that have been described thus far is limited to cells of mesenchymal origin, including the best characterized mesenchymal stem cell (See Pittenger, et al. Science (1999) 284: 143-147 and U.S. Pat. No. 5,827,740 (SH2$^+$ SH4$^+$ CD29$^+$ CD44$^+$ CD71$^+$ CD90$^+$ CD106$^+$ CD120a$^+$ CD124$^+$ CD14$^-$ CD34$^-$ CD45$^-$)).

For the reasons noted above regarding the limitations, risks, and controversies of and relating to ES, EG, and germ cells, a substantial portion of work on the use of stem cells in transplantation therapies has utilized MSCs. Results of the last few years appear to show that allografts of MSCs do not engender a HVG immune reaction, which is a response invariably seen when other tissue is transplanted between allogeneic individuals. Moreover, the results suggest that MSCs weaken lymphocyte immune response, at least in some circumstances.

While these results immediately suggest that MSCs might be useful to decrease HVG and/or GVHD that ordinarily would accompany allogeneic transplantation, the observed immunosuppressive effects of MSCs were highly dose dependent, and relatively high doses were required to observe an immunosuppressive effect. In fact, decreased proliferation of lymphocytes in mixed lymphocyte assays in vitro was "marked" only at or above a 1:10 ratio of MSCs to lymphocytes. Furthermore, the observed inhibitory effect decreased and became unobservable as the dose of MSCs decreased, and at ratios below 1:100 the presence of MSCs actually seemed to stimulate proliferation of the T-cells. The same dose effects also were observed in mitogen-stimulated lymphocyte proliferation assays. See, for review, Ryan et al. (2005) "Mesenchymal stem cells avoid allogeneic rejection," *J. Inflammation* 2: 8; Le Blanc (2003) "Immunomodulatory effects of fetal and adult mesenchymal stem cells," *Cytotherapy* 5(6): 485-489, and Jorgensen et al. (2003) "Engineering mesenchymal stem cells for immunotherapy," *Gene Therapy* 10: 928-931. Additional results are summarized below.

For example, Bartholomew and co-workers found that baboon MSCs did not stimulate allogeneic lymphocytes to proliferate in vitro and that MSCs reduced proliferation of mitogen-stimulated lymphocytes by more than 50% in mixed lymphocyte assays in vitro. They further showed that administration of MSCs in vivo prolonged skin graft survival (relative to controls). Both the in vitro results and the in vivo results required a high dose of MSCs: 1:1 ratio with the lymphocytes for the in vitro results. The amount of MSCs that would be required to approach such a ratio in vivo in humans may be too high to achieve, as a practical matter. This may limit the utility of MSCs. See Bartholomew et al. (2002): "Mesenchymal stem cells suppress lymphocyte proliferation in vitro and prolong skin graft survival in vivo," *Experimental Hematology* 30: 42-48.

Maitra and co-workers examined the effects of human MSCs on engraftment of allogeneic human umbilical cord blood cells after co-infusion into sub-lethally irradiated NOD-SCID mice. They found that human MSCs promoted engraftment and did not activate allogeneic T-cells in in vitro proliferation assays. They also found that human MSCs suppressed in vitro activation of allogeneic human T-cells by mitogens. The effects were dose dependent and relatively high ratios were required for suppression. (Maitra et al. (2004) *Bone Marrow Transplantation* 33: 597-604.)

Recently, Le Blanc and co-workers reported successfully treating one patient with Grade IV acute GVHD, which usually is fatal, by administration of "third party haploidentical" MSCs. The patient was a 9-year old boy with acute lymphoblastic leukemia, which was in its third remission. Initially, the patient was treated with radiation and cyclophosphamide and then given blood cells that were identical to his own cells at the HLA-A, HLA-B, and HLA-DRbeta1 loci. These had been obtained from an unrelated female donor. Despite aggressive treatment, including dosing with a variety of immunosuppressants, by 70 days after transplant the patient developed Grade IV acute GVHD. He was frequently afflicted by invasive bacterial, viral, and fungal infections.

Under these clearly dire circumstances, an alternative blood stem cell transplant was attempted. Haploidentical MSCs were isolated from the patient's mother and expanded in vitro for three weeks. The cells were harvested and $2\times10^6$ cells per kilogram were administered to the patient intravenously. There were no signs of toxicity associated with the MSCs, nor were there substantial side effects. Many symptoms resolved within a few days after the transplant; but, residual disease was apparent. After several additional intravenous injections of MSCs using the same methods, the patient's symptoms and GVHD were fully resolved. The patient was still disease free one year after discharge. According to the authors, in their experience, this patient is unique in surviving GVHD of this severity. The results reported by Le Blanc et al. are both promising and inspiring, and should be a spur to developing effective therapies that utilize stem cells. Le Blanc et al. (2004) "Treatment of severe acute graft-versus-host disease with third party haploidentical mesenchymal stem cells," *Lancet* 363: 1439-41.

Nevertheless, these results, including those of Le Blanc and co-workers, reveal potential shortcomings of MSCs. The cells need to be administered with traditional immunosuppressive modalities which then will continue to engender deleterious immune responses. The dosing requirements for MSCs apparently will need to be very high to be effective, which will incur greater cost, more difficulty in administration, greater risk of toxicity and other harmful side effects, and other disadvantages.

In view of these limitations of current stem cell based transplantation-related therapies, there is clearly a strong need for progenitor cells that can be used for all—or at least most—recipient hosts without necessitating a host-recipient haplotype match. Further, there is a need for cells of greater "specific activity" so that they are therapeutically effective at lower doses and their administration does not pose the problems associated with the high dosing regimens required for beneficial results using MSCs. And, there is a need for cells that have essentially unlimited differentiation potential to form cells that occur in the organism of interest.

Unrestricted Stem Cells

Until recently only ES, EG, and germ cells were thought to have both unlimited capacity for self-renewal and unrestricted differentiation potential, i.e., the ability to produce all the different types of cells and tissues of an organism that occur throughout its embryogenesis, development, adulthood, and senescence. Accordingly, these ES, EG, and germ cells traditionally have been seen as the most promising stem cells for medical uses, such as for applications that involve regenerating healthy tissue, and those involving transplantation of cells and/or re-growth of healthy tissue. The embryonal stem ("ES") cell has unlimited self-renewal and can differentiate into all tissue types. ES cells are derived from the inner cell mass of the blastocyst. Embryonal germ ("EG") cells are derived from primordial germ cells of a post-implantation embryo. ES and EG cells have been derived from mouse, and, more recently, from non-human primates and humans. When introduced into blastocysts, ES cells can contribute to all tissues. A drawback to ES cell therapy is that when transplanted in post-natal animals, ES and EG cells generate teratomas.

ES (and EG) cells can be identified by positive staining with antibodies to SSEA1 (mouse) and SSEA4 (human). At the molecular level, ES and EG cells express a number of transcription factors highly specific for these undifferentiated cells. These include oct-4 and rex-1. Rex-1 expression is controlled by oct-4, which activates downstream expression of rex-1. Also found are the LIF-R (in mouse) and the transcription factors sox-2 and rox-1. Rox-1 and sox-2 are also expressed in non-ES cells. A hallmark of ES cells is the presence of telomerase, which provides these cells with an unlimited self-renewal potential in vitro.

Oct-4 (oct-3 in humans) is a transcription factor expressed in the pregastrulation embryo, early cleavage stage embryo, cells of the inner cell mass of the blastocyst, and embryonic carcinoma ("EC") cells (Nichols, J. et al. (1998) *Cell* 95: 379-91), and is down-regulated when cells are induced to differentiate. The oct-4 gene (oct-3 in humans) is transcribed into at least two splice variants in humans, oct-3A and oct-3B. The oct-3B splice variant is found in many differentiated cells whereas the oct-3A splice variant (also previously designated oct-3/4) is reported to be specific for the undifferentiated embryonic stem cell. See Shimozaki et al. (2003) *Development* 130: 2505-12. Expression of oct-3/4 plays an important role in determining early steps in embryogenesis and differentiation. Oct-3/4, in combination with rox-1, causes transcriptional activation of the Zn-finger protein rex-1, which is also required for maintaining ES cells in an undifferentiated state (Rosfjord, E. and Rizzino, A. (1997) *Biochem Biophys Res Commun* 203: 1795-802; Ben-Shushan, E. et al. (1998) *Mol Cell Biol* 18: 1866-78).

In addition, sox-2, expressed in ES/EC cells, but also in other more differentiated cells, is needed together with oct-4 to retain the undifferentiated state of ES/EC cells (Uwanogho, D. et al. (1995) *Mech Dev* 49: 23-36). Maintenance of murine ES cells and primordial germ cells requires the presence of LIF whereas this requirement is not as clear for human and non-human primate ES cells.

As noted above, ES, EG, and germ cells, despite their seemingly unlimited differentiation potential, have not been as intense a focus of attention as they might have been for several reasons. These include, among other things, safety concerns, ethical concerns, logistical issues, limits on the use of federal funding for research on embryo-derived cells and cell lines (other than a limited number of specifically approved human embryonic stem cell lines), economic considerations, and political risk factors that have become associated with human embryonic stem cell research.

Accordingly, there has been a need for cells that have the self-renewing and differentiation capacity of ES, EG, and germ cells but are not immunogenic; do not form teratomas when allografted or xenografted to a host; do not pose other safety issues associated with ES, EG, and germ cells; retain the other advantages of ES, EG, and germ cells; are easy to isolate from readily available sources, such as placenta, umbilical cord, umbilical cord blood, blood, and bone marrow; can be stored safely for extended periods; can be obtained easily and without risk to volunteers, donors or patients, and others giving consent; and do not entail the technical and logistical difficulties involved in obtaining and working with ES, EG, and germ cells.

Recently, a type of cell, called herein multipotent adult progenitor cells ("MAPCs"), has been isolated and characterized. These cells provide many of the advantages of ES, EG, and germ cells without many of their drawbacks.

SUMMARY OF THE INVENTION

In some of its embodiments, therefore, the invention provides cells that: (i) are not embryonic stem cells, not embryonic germ cells, and not germ cells; (ii) can differentiate into at least one cell type of each of at least two of the endodermal, ectodermal, and mesodermal embryonic lineages; (iii) do not provoke a deleterious immune response upon introduction to a non-syngeneic subject; and (iv) can modulate an immune response upon introduction into a subject. In certain embodiments in this regard, the invention provides cells that, in addition to the foregoing, are immunosuppressive. Furthermore, various embodiments of the invention provide cells in accordance with the foregoing that have immunomodulatory properties that are useful for treating, such as to preclude, prevent, ameliorate, lessen, decrease, minimize, eliminate, and/or cure deleterious immune responses and/or processes in a host. In some embodiments of the invention the cells are used in this regard alone or together with other therapeutic agents and modalities as primary therapeutic modalities. In some embodiments of the invention the cells are used in an adjunctive therapeutic modality in which they may be used either as the sole therapeutic agent or together with other therapeutic agents. In some embodiments of the invention the cells are used, alone or with other therapeutic agents or modalities, both in one or more primary therapeutic modalities and in one or move adjunctive therapeutic modalities.

Cells in accordance with the invention are described in greater detail herein and generally are referred to herein as "multipotent adult progenitor cells" and by the acronyms "MAPC" (singular) and "MAPCs" (plural). It is to be appreciated that these cells are not ES, not EG, and not germ cells, and that they have the capacity to differentiate into cell types of at least two of the three primitive germ layer lineages (ectoderm, mesoderm, and endoderm), and, in many cases into cells of all three primitive lineages.

MAPCs express telomerase which is considered to be necessary for self-renewal and is thought to be necessary for maintaining an undifferentiated state. Generally they also express oct-3/4. Oct-3/4 (oct-3A in humans) is otherwise specific to ES, EG, and germ cells. It is considered to be a marker of undifferentiated cells that have broad differentiation abilities. Oct-3/4 also is generally thought to have a role in maintaining a cell in an undifferentiated state. MAPCs generally also express other markers thought to be specific to primitive stem cells. Among these are rex-1, rox-1, and sox-2.

MAPCs are biologically and antigenically distinct from mesenchymal stem cells ("MSCs"). MAPCs have demonstrated differentiation capability encompassing the epithelial, endothelial, neural, myogenic, hematopoietic, osteogenic, hepatogenic, chondrogenic, and adipogenic lineages, among others. They are far less restricted in differentiation potential than MSCs and, therefore, constitute a progenitor cell population that is less committed and less restricted in developmental potential than MSCs. They are apparently more primitive progenitor cells than MSCs. (Verfaillie, C. M. (2002) *Trends Cell Biol.* 12(11): 502-8, Jahagirdar, B. N. et al. (2001) *Exp Hematol.* 29(5): 543-56). Thus, MAPCs are a class of non-ES, non-EG, non-germ cells which emulate the broad biological plasticity characteristics of ES, EG, and germ cells, while maintaining other characteristics that make non-embryonic stem cells appealing. For example, MAPCs are capable of indefinite culture without loss of their differentiation potential. They show efficient, long term engraftment and differentiation along multiple developmental lineages in NOD-SCID mice and do so without evidence of teratoma formation (often seen with ES, EG, and germ cells) (Reyes, M. and C. M. Verfaillie (2001) *Ann N Y Acad Sci.* 938: 231-3; discussion 233-5).

MAPCs were initially isolated from bone marrow but subsequently have been established from other tissues, including brain, muscle, and cord blood (Jiang, Y. et al. (2002) *Exp Hematol.* 30(8): 896-904). MAPCs have been prepared from bone marrow tissue by enriching adherent cells in media containing low serum (2%) dexamethasone, EGF, PDGF, and other additives, and then growing them to high population doublings. At early culture points, more heterogeneity is detected in the population. Around cell doubling 30, many adherent stromal cells undergo replicative senescence. The population of cells that continues to expand thereafter becomes more homogenous and is characterized by cells that have long telomeres. Methods for obtaining and culturing the cells are described in greater detail elsewhere herein.

Various embodiments of the invention provide methods for using MAPCs for precluding, preventing, treating, ameliorating, lessening, decreasing, minimizing, eliminating, and/or curing a disease and/or an adverse immune response and/or processes in a subject. Certain embodiments of the invention provide methods for using the cells by themselves as a primary therapeutic modality. In some embodiments of the invention the cells are used together with one or more other agents and/or therapeutic modalities as the primary therapeutic modality. In some embodiments of the invention the cells are used as an adjunctive therapeutic modality, that is, as an adjunct to another, primary therapeutic modality. In some embodiments the cells are used as the sole active agent of an adjunctive therapeutic modality. In others the cells are used as an adjunctive therapeutic modality together with one or more other agents or therapeutic modalities. In some embodiments the cells are used both as primary and as adjunctive therapeutic agents and/or modalities. In both regards, the cells can be used alone in the primary and/or in the adjunctive modality. They also can be used together with other therapeutic agents or modalities, in the primary or in the adjunctive modality or both.

As discussed above, a primary treatment, such as a therapeutic agent, therapy, and/or therapeutic modality, targets (that is, is intended to act on) the primary dysfunction, such as a disease, that is to be treated. An adjunctive treatment, such as a therapy and/or a therapeutic modality, can be administered in combination with a primary treatment, such as a therapeutic agent, therapy, and/or therapeutic modality, to act on the primary dysfunction, such as a disease, and supplement the effect of the primary treatment, thereby increasing the overall efficacy of the treatment regimen. An adjunctive treatment, such as an agent, therapy, and/or therapeutic modality, also can be administered to act on complications and/or side effects of a primary dysfunction, such as a disease, and/or those caused by a treatment, such as a therapeutic agent, therapy, and/or therapeutic modality. In regard to any of these uses, one, two, three, or more primary treatments may be used together with one, two, three, or more adjunctive treatments.

In some embodiments MAPCs are administered to a subject prior to onset of a dysfunction, such as a disease, side effect, and/or deleterious immune response. In some embodiments the cells are administered while the dysfunction is developing. In some embodiments the cells are administered after the dysfunction has been established. Cells can be administered at any stage in the development, persistence, and/or propagation of the dysfunction or after it recedes.

As discussed above, embodiments of the invention provide cells and methods for primary or adjunctive therapy. In certain embodiments of the invention, the cells are administered to an allogeneic subject. In some embodiments they are autologous to the subject. In some embodiments they are syngeneic to the subject. In some embodiments the cells are xenogeneic to a subject. Whether allogeneic, autologous, syngeneic, or xenogeneic, in various embodiments of the invention the MAPCs are weakly immunogenic or are non-immunogenic in the subject. In some embodiments the MAPCs have sufficiently low immunogenicity or are non-immunogenic and are sufficiently free of deleterious immune responses in general, that when administered to allogeneic subjects they can be used as "universal" donor cells without tissue typing and matching. In accordance with various embodiments of the invention the MAPCs can also be stored and maintained in cell banks, and thus can be kept available for use when needed.

In all of these regards and others, embodiments of the invention provide MAPCs from mammals, including in one embodiment humans, and in other embodiments non-human primates, rats and mice, and dogs, pigs, goats, sheep, horses, and cows. MAPCs prepared from mammals as described above can be used in all of the methods and other aspects of the invention described herein.

MAPCs in accordance with various embodiments of the invention can be isolated from a variety of compartments and tissues of such mammals, including but not limited to, bone marrow, blood, spleen, liver, muscle, brain, and others discussed below. MAPCs in some embodiments are cultured before use.

In some embodiments MAPCs are genetically engineered, such as to improve their immunomodulatory properties. In some embodiments genetically engineered MAPCs are produced by in vitro culture. In some embodiments genetically engineered MAPCs are produced from a transgenic organism.

In various embodiments the MAPCs are administered to a subject by any route for effective delivery of cell therapeutics. In some embodiments the cells are administered by injection, including local and/or systemic injection. In certain embodiments the cells are administered within and/or in proximity to the site of the dysfunction they are intended to treat. In some embodiments, the cells are administered by injection at a location not in proximity to the site of the dysfunction. In some embodiments the cells are administered by systemic injection, such as intravenous injection.

In some embodiments, MAPCs are administered one time, two times, three times, or more than three times until a desired therapeutic effect is achieved or administration no longer appears to be likely to provide a benefit to the subject. In some embodiments MAPCs are administered continuously for a period of time, such as by intravenous drip. Administration of MAPCs may be for a short period of time, for days, for weeks, for months, for years, or for longer periods of time.

The following numbered paragraphs describe a few illustrative embodiments of the invention that exemplify some of its aspects and features. They are not exhaustive in illustrating its many aspects and embodiments, and thus are not in any way limitative of the invention. Many other aspects, features, and embodiments of the invention are described herein. Many other aspects and embodiments will be readily apparent to those skilled in the art upon reading the application and giving it due consideration in the full light of the prior art and knowledge in the field.

The numbered paragraphs below are self-referential. The phrase "according to any of the foregoing or the following" refers to all of the preceding and all of the following numbered paragraphs and their contents. All phrases of the form "according to #" are direct references to that numbered paragraph, e.g., "according to 46." means according to paragraph 46. in this collection of numbered paragraphs. All cross-references are combinatorial, except for redundancies and inconsistencies of scope. The cross-references are used explicitly to provide a concise description showing the inclusion of the various combinations of subject matter with one another.

1. A method of treating an immune dysfunction in a subject, comprising: administering to a subject likely to suffer, suffering, or who has suffered from an immune dysfunction, by an effective route and in an effective amount to treat the immune dysfunction, cells (MAPCs) that: are not embryonic stem cells, embryonic germ cells, or germ cells; can differentiate into at least one cell type of each of at least two of the endodermal, ectodermal, and mesodermal embryonic lineages; do not provoke a deleterious immune response in the subject; and are effective to treat the immune dysfunction.

2. A method of adjunctive treatment of a subject, comprising: administering to a subject likely to suffer, suffering, or who has suffered from an immune dysfunction, by an effective route and in an effective amount to treat the immune dysfunction, cells (MAPCs) that: are not embryonic stem cells, embryonic germ cells, or germ cells; can differentiate into at least one cell type of each of at least two of the endodermal, ectodermal, and mesodermal embryonic lineages; do not provoke a deleterious immune response in the subject; and are effective to treat the immune dysfunction, wherein the cells are administered adjunctively to one or more other treatments administered to the subject to treat the same thing, to treat something different, or both.

3. A method according to any of the foregoing or the following, wherein said cells can differentiate into at least one cell type of each of the endodermal, ectodermal, and mesodermal embryonic lineages.

4. A method according to any of the foregoing or the following, wherein said cells express telomerase.

5. A method according to any of the foregoing or the following, wherein said cells are positive for oct-3/4.

6. A method according to any of the foregoing or the following, wherein said cells have undergone at least 10 to 40 cell doublings in culture prior to their administration to the subject.

7. A method according to any of the foregoing or the following, wherein said cells are mammalian cells.

8. A method according to any of the foregoing or the following, wherein said cells are human, horse, cow, goat, sheep, pig, rat, or mouse cells.

9. A method according to any of the foregoing or the following, wherein said cells are human, rat, or mouse cells.

10. A method according to any of the foregoing or the following, wherein said cells are human cells.

11. A method according to any of the foregoing or the following, wherein said cells are derived from cells isolated from any of placental tissue, umbilical cord tissue, umbilical cord blood, bone marrow, blood, spleen tissue, thymus tissue, spinal cord tissue, adipose tissue, and liver tissue.

12. A method according to any of the foregoing or the following, wherein said cells are derived from cells isolated from any of placental tissue, umbilical cord tissue, umbilical cord blood, bone marrow, blood, and spleen tissue.

13. A method according to any of the foregoing or the following, wherein said cells are derived from cells isolated from any of placental tissue, umbilical cord tissue, umbilical cord blood, bone marrow, or blood.

14. A method according to any of the foregoing or the following, wherein said cells are derived from cells isolated from any one or more of bone marrow or blood.

15. A method according to any of the foregoing or the following, wherein said cells are allogeneic to the subject.

16. A method according to any of the foregoing or the following, wherein said cells are xenogeneic to the subject.

17. A method according to any of the foregoing or the following, wherein said cells are autologous to the subject.

18. A method according to any of the foregoing or the following wherein the subject is a mammal.

19. A method according to any of the foregoing or the following wherein the subject is a mammalian pet animal, a mammalian livestock animal, a mammalian research animal, or a non-human primate.

20. A method according to any of the foregoing or the following, wherein the subject is a human.

21. A method according to any of the foregoing or the following, wherein said cells are administered to the subject in one or more doses comprising $10^4$ to $10^8$ of said cells per kilogram of the subject's mass.

22. A method according to any of the foregoing or the following, wherein said cells are administered to the subject in one or more doses comprising $10^5$ to $10^7$ of said cells per kilogram of the subject's mass.

23. A method according to any of the foregoing or the following, wherein said cells are administered to the subject in one or more doses comprising $5 \times 10^6$ to $5 \times 10^7$ of said cells per kilogram of the subject's mass.

24. A method according to any of the foregoing or the following, wherein said cells are administered to the subject in one or more doses comprising $2 \times 10^7$ to $4 \times 10^7$ of said cells per kilogram of the subject's mass.

25. A method according to any of the foregoing or the following, wherein in addition to said cells, one or more factors are administered to said subject.

26. A method according to any of the foregoing or the following, wherein in addition to said cells, one or more growth factors, differentiation factors, signaling factors, and/or factors that increase homing are administered to said subject.

27. A method according to any of the foregoing or the following, wherein in addition to said cells, one or more cytokines are administered to said subject.

28. A method according to any of the foregoing or the following, wherein said cells are administered to a subject adjunctively to another treatment that is administered before, at the same time as, or after said cells are administered.

29. A method according to any of the foregoing or the following, wherein said cells are administered to the subject adjunctively to administration to the subject of one or more immunosuppressive agents.

30. A method according to any of the foregoing or the following, wherein in addition to treatment with said cells, the subject is to receive or has received a transplant, wherein said cells are administered adjunctively thereto.

31. A method according to any of the foregoing or the following, wherein in addition to treatment with said cells, the subject is to receive or has received a transplant of a kidney, heart, lung, liver, or other organ, wherein said cells are administered adjunctively thereto.

32. A method according to any of the foregoing or the following, wherein in addition to treatment with said cells, the subject is to receive or has received a transplant of bone marrow, vein, artery, muscle, or other tissue, wherein said cells are administered adjunctively thereto.

33. A method according to any of the foregoing or the following, wherein in addition to treatment with said cells, the subject is to receive or has received a transplant of blood cells, islet cells, or other tissue or organ regenerating cells, wherein said cells are administered adjunctively thereto.

34. A method according to any of the foregoing or the following, wherein in addition to treatment with said cells, the subject is to receive or has received a blood cell transplant, wherein said cells are administered adjunctively thereto.

35. A method according to any of the foregoing or the following, wherein in addition to treatment with said cells, the subject is to receive or has received a bone marrow transplant, wherein said cells are administered adjunctively thereto.

36. A method according to any of the foregoing or the following, wherein in addition to treatment with said cells, the subject has been, will be, or is being treated with one or more immunosuppressive agents, wherein said cells are administered adjunctively thereto.

37. A method according to any of the foregoing or the following, wherein in addition to treatment with said cells, the subject has been, will be, or is being treated with one or more of a corticosteroid, cyclosporin A, a cyclosporin-like immunosuppressive agent, cyclophosphamide, antithymocyte globulin, azathioprine, rapamycin, FK-506, and a macrolide-like immunosuppressive agent other than FK-506, rapamycin, and an immunosuppressive monoclonal antibody agent (i.e., an immunosuppressive that is an immunosuppressive monoclonal antibody or is an agent comprising a monoclonal antibody, in whole or in one or more parts, such as a chimeric protein comprising an Fc or a Ag binding site of a monoclonal antibody), wherein said cells are administered adjunctively thereto.

38. A method according to any of the foregoing or the following, wherein in addition to treatment with said cells, the subject has been, will be, or is being treated with one or more of a corticosteroid, cyclosporin A, azathioprine, rapamycin, cyclophosphamide, FK-506, or an immunosuppressive monoclonal antibody agent, wherein said cells are administered adjunctively thereto.

39. A method according to any of the foregoing or the following, wherein said cells are administered to the subject adjunctively to administration to the subject of one or more antibiotic agents.

40. A method according to any of the foregoing or the following, wherein said cells are administered to the subject adjunctively to administration to the subject of one or more anti-fungal agents.

41. A method according to any of the foregoing or the following, wherein said cells are administered to the subject adjunctively to administration to the subject of one or more anti-viral agents.

42. A method according to any of the foregoing or the following, wherein said cells are administered to the subject adjunctively to the administration to the subject of any combination of two or more of any immunosuppressive agents and/or antibiotic agents and/or anti-fungal agents and/or anti-viral agents.

43. A method according to any of the foregoing or the following, wherein said cells are administered to the subject adjunctively to a transplant therapy to treat a host versus graft response in the subject that is impairing or might impair the therapeutic efficacy of the transplant and/or is or might result in transplant rejection.

44. A method according to any of the foregoing or the following, wherein said cells are administered to a subject having a weakened immune system, such as one or more of a compromised immune system and/or an ablated immune system.

45. A method according to any of the foregoing or the following, wherein said cells are administered to a subject adjunctively to radiation therapy or chemotherapy or a combination of radiation and chemotherapy that either have been, are being, or will be administered to the subject.

46. A method according to any of the foregoing or the following, wherein said cells are administered to a subject adjunctively to an on-going regimen of radiation therapy or chemotherapy or a combination of radiation and chemotherapy.

47. A method according to any of the foregoing or the following, wherein the immune system of the subject has been weakened, compromised, and/or or ablated by radiation therapy, chemotherapy, or a combination of radiation and chemotherapy.

48. A method according to any of the foregoing or the following, wherein the subject is the recipient of a non-syngeneic blood cell or bone marrow transplant, the immune system of the subject has been weakened or ablated by radiation therapy, chemotherapy, or a combination of radiation and chemotherapy, and the subject is at risk to develop or has developed graft versus host disease.

49. A method according to any of the foregoing or the following, wherein the subject is the recipient of a non-syngeneic blood cell or bone marrow transplant, the immune system of the subject has been weakened or ablated by radiation therapy, by chemotherapy, or by a combination of radiation therapy and chemotherapy, and immunosuppressive drugs are being administered to the subject, wherein further the subject is at risk to develop or has developed graft versus host disease and said cells are administered to said subject to treat graft versus host disease adjunctively to one or more of the other treatments (that is: the transplant, the radiation therapy, the chemotherapy, and/or the immunosuppressive drugs).

50. A method according to any of the foregoing or the following, wherein the subject will be or is the recipient of a non-syngeneic transplant and is at risk for or has developed a host versus graft response, wherein said cells are administered to treat the host versus graft response.

51. A method according to any of the foregoing or the following, wherein the subject is at risk for or is suffering from a neoplasm and said cells are administered adjunctive to a treatment thereof.

52. A method according to any of the foregoing or the following, wherein the subject is at risk for or is suffering from a neoplasm of blood or bone marrow cells and said cells are administered adjunctive to a treatment thereof.

53. A method according to any of the foregoing or the following, wherein the subject is at risk for or is suffering from a benign neoplasm of bone marrow cells, a myeloproliferative disorder, a myelodysplastic syndrome, or an acute leukemia and said cells are administered adjunctive to a treatment thereof.

54. A method according to any of the foregoing or the following, wherein the subject is at risk for or is suffering from a benign neoplasm of bone marrow cells and said cells are administered adjunctive to a treatment thereof.

55. A method according to any of the foregoing or the following, wherein the subject is at risk for or is suffering from a myeloproliferative disorder and said cells are administered adjunctive to a treatment thereof.

56. A method according to any of the foregoing or the following, wherein the subject is at risk for or is suffering from one or more of chronic myelocytic leukemia ("CML") (also called chronic granulocytic leukemia ("CGL")), agnogenic myelofibrosis, essential thrombocythemia, polycythemia vera, or other myeloproliferative disorder and said cells are administered adjunctive to a treatment thereof.

57. A method according to any of the foregoing or the following, wherein the subject is at risk for or is suffering from a myelodysplastic syndrome and said cells are administered adjunctive to a treatment thereof.

58. A method according to any of the foregoing or the following, wherein the subject is at risk for or is suffering from an acute leukemia and said cells are administered adjunctive to a treatment thereof.

59. A method according to any of the foregoing or the following, wherein the subject is at risk for or is suffering from one or more of acute multiple myeloma, myeloblastic leukemia, chronic myelocytic leukemia ("CML"), acute promyelocytic leukemia, pre-B acute lymphoblastic leukemia, chronic lymphocytic leukemia ("CLL"), B-cell lymphoma, hairy cell leukemia, myeloma, T-acute lymphoblastic leukemia, peripheral T-cell lymphoma, other lymphoid leukemias, other lymphomas, or other acute leukemia and said cells are administered adjunctive to a treatment thereof.

60. A method according to any of the foregoing or the following, wherein the subject is at risk for or is suffering from an anemia or other blood disorder and said cells are administered adjunctive to a treatment thereof.

61. A method according to any of the foregoing or the following, wherein the subject is at risk for or is suffering from hemoglobinopathies, thalassemia, bone marrow failure syndrome, sickle cell anemia, aplastic anemia, Fanconi's anemia, or an immune hemolytic anemia and said cells are administered adjunctive to a treatment thereof.

62. A method according to any of the foregoing or the following, wherein the subject is at risk for or is suffering from one or more of refractory anemia, refractory anemia with ringed sideroblasts, refractory anemia with excess blasts, refractory anemia with excess blasts in transformation, chronic myelomonocytic leukemia, or other myelodysplastic syndrome and said cells are administered adjunctive to a treatment thereof.

63. A method according to any of the foregoing or the following, wherein the subject is at risk for or is suffering from Fanconi's anemia and said cells are administered adjunctive to a treatment thereof.

64. A method according to any of the foregoing or the following, wherein the subject is at risk for or is suffering from an immune dysfunction and said cells are administered adjunctive to a treatment thereof.

65. A method according to any of the foregoing or the following, wherein the subject is at risk for or is suffering from a congenital immune deficiency and said cells are administered adjunctive to a treatment thereof.

66. A method according to any of the foregoing or the following, wherein the subject is at risk for or is suffering from an autoimmune dysfunction, disorder, or disease and said cells are administered adjunctive to a treatment thereof.

67. A method according to any of the foregoing or the following, wherein the subject is at risk for or is suffering from one or more of the following autoimmune dysfunctions: Crohn's disease, Guillain-Barré syndrome, lupus erythematosus (also called "SLE" and systemic lupus erythematosus), multiple sclerosis, myasthenia gravis, optic neuritis, psoriasis, rheumatoid arthritis, Graves' disease, Hashimoto's disease, Ord's thyroiditis, diabetes mellitus (type 1), Reiter's syndrome, autoimmune hepatitis, primary biliary cirrhosis, antiphospholipid antibody syndrome ("APS"), opsoclonus-myoclonus syndrome ("OMS"), temporal arteritis, acute disseminated encephalomyelitis ("ADEM" and "ADE"), Goodpasture's, syndrome, Wegener's granulomatosis, celiac disease, pemphigus, polyarthritis, and warm autoimmune hemolytic anemia and said cells are administered adjunctive to a treatment thereof.

68. A method according to any of the foregoing or the following, wherein the subject is at risk for or is suffering from one or more of the following autoimmune dysfunctionss: Crohn's disease, lupus erythematosus (also called "SLE" and systemic lupus erythematosus), multiple sclerosis, myasthenia gravis, psoriasis, rheumatoid arthritis, Graves' disease, Hashimoto's disease, diabetes mellitus (type 1), Reiter's syndrome, primary biliary cirrhosis, celiac disease, polyarthritis, and warm autoimmune hemolytic anemia and said cells are administered adjunctive to a treatment thereof.

69. A method according to any of the foregoing or the following, wherein the subject is at risk for or is suffering from one or more of the following diseases thought to have an autoimmune component: endometriosis, interstitial cystitis, neuromyotonia, scleroderma, progressive systemic scleroderma, vitiligo, vulvodynia, Chagas' disease, sarcoidosis, chronic fatigue syndrome, and dysautonomia and said cells are administered adjunctive to a treatment thereof.

70. A method according to any of the foregoing or the following, wherein the subject is at risk for or is suffering from an inflammatory disease and said cells are administered adjunctive to a treatment thereof.

71. A method according to any of the foregoing or the following, wherein said cells are administered in a formulation comprising one or more other pharmaceutically active agents.

72. A method according to any of the foregoing or the following, wherein said cells are administered in a formulation comprising one or more other immunosuppressive agents.

73. A method according to any of the foregoing or the following, wherein said cells are administered in a formulation comprising one or more of a corticosteroid, cyclosporin A, a cyclosporin-like immunosuppressive agent, cyclophosphamide, antithymocyte globulin, azathioprine, rapamycin, FK-506, and a macrolide-like immunosuppressive agent other than FK-506, rapamycin, and an immunosuppressive monoclonal antibody agent.

74. A method according to any of the foregoing or the following, wherein said cells are administered in a formulation comprising one or more of a corticosteroid, cyclosporin A, azathioprine, cyclophosphamide, rapamycin, FK-506, and an immunosuppressive monoclonal antibody agent.

75. A method according to any of the foregoing or the following, wherein said cells are administered in a formulation comprising one or more antibiotic agents.

76. A method according to any of the foregoing or the following, wherein said cells are administered in a formulation comprising one or more antifungal agents.

77. A method according to any of the foregoing or the following, wherein said cells are administered in a formulation comprising one or more antiviral agents.

78. A method according to any of the foregoing or the following, wherein said cells are administered to the subject by a parenteral route.

79. A method according to any of the foregoing or the following, wherein said cells are administered to the subject by any one or more of the following parenteral routes: intravenous, intraarterial, intracardiac, intraspinal, intrathecal, intraosseous, intraarticular, intrasynovial, intracutaneous, intradermal, subcutaneous, and intramuscular injection.

80. A method according to any of the foregoing or the following, wherein said cells are administered by any one or more of the following parenteral routes: intravenous, intraarterial, intracutaneous, intradermal, subcutaneous, and intramuscular injection.

81. A method according to any of the foregoing or the following, wherein said cells are administered by any one or more of the following parenteral routes: intravenous, intraarterial, intracutaneous, subcutaneous, and intramuscular injection.

82. A method according to any of the foregoing or the following, wherein said cells are administered to the subject through a hypodermic needle by a syringe.

83. A method according to any of the foregoing or the following, wherein said cells are administered to the subject through a catheter.

84. A method according to any of the foregoing or the following, wherein said cells are administered by surgical implantation.

85. A method according to any of the foregoing or the following, wherein said cells are administered to the subject by implantation using an arthroscopic procedure.

86. A method according to any of the foregoing or the following, wherein said cells are administered to the subject in or on a support.

87. A method according to any of the foregoing or the following, wherein said cells are administered to the subject in an encapsulated form.

88. A method according to any of the foregoing or the following, wherein said cells are formulated suitably for administration by any one or more of the following routes: oral, rectal, epicutaneous, ocular, nasal, and pulmonary.

89. A method according to any of the foregoing or the following, wherein said cells are administered to the subject in one dose.

90. A method according to any of the foregoing or the following, wherein said cells are administered to the subject in a series of two or more doses in succession.

91. A method according to any of the foregoing or the following, wherein said cells are administered in a single dose, in two doses, or in more than two doses, wherein the doses are the same or different, and they are administered with equal or with unequal intervals between them.

92. A method according to any of the foregoing or the following, wherein said cells are administered over a period of less than one day to one week, one week to one month, one month to one year, one year to two years, or longer than two years.

93. A method of treatment of an immune dysfunction in a subject, comprising administering to a subject suffering from an immune dysfunction, by a route and in an amount effective for treating the immune dysfunction in the subject, cells that: are not embryonic stem cells, embryonic germ cells, or germ cells; can differentiate into at least one cell type of each of at least two of the endodermal, ectodermal, and mesodermal embryonic lineages; do not provoke a deleterious immune response in the subject; and are effective to treat the immune dysfunction in the subject.

94. A method of adjunctive treatment of an immune dysfunction in a subject, comprising administering to a subject suffering from an immune dysfunction, by a route and in an amount effective for treating the immune dysfunction in the subject, cells that: are not embryonic stem cells, embryonic germ cells, or germ cells; can differentiate into at least one cell type of each of at least two of the endodermal, ectodermal, and mesodermal embryonic lineages; do not provoke a deleterious immune response in the subject; and are effective to treat the immune dysfunction in the subject, wherein the cells are administered to the subject adjunctively to one or more other treatments that are being administered to the subject to treat the same immune dysfunction, to treat one or more other dysfunctions, or both.

Other aspects of the invention are described in or are obvious from the following disclosure, and are within the ambit of the invention.

BRIEF DESCRIPTIONS OF THE FIGURES

FIG. 1 is a schematic representation of the transcriptional profiling studies that were performed to generate (identify) gene and surface receptor-based markers that distinguish between MAPCs of the invention and other stem and progenitor cells that are more lineage committed. The experiments have resulted in a panel of 75 markers having 10-fold different expression between MSC cultures and the MAPCs.

FIG. 2 is a set of graphs showing the tri-lineage differentiation of GFP-labeled rat MAPCs. The results show that MAPCs can differentiate into cells of all three embryonic lineages. As further described below, for endothelial differentiation, MAPCs were cultured on fibronectin-coated plates in the presence of vascular endothelial growth factor B (VEGF-B). For hepatocyte differentiation, cells were grown on matrigel-coated plates and treated with fibroblast growth factor-4 (FGF-4) and hepatocyte growth factor (HGF). Neuronal differentiation was induced by sequential treatment with basic-FGF (bFGF), with both FGF-8 and Sonic Hedgehog (SHH), and with brain-derived neurotrophic factor (BDNF). After two weeks, mRNA was extracted from cells and applied to qPCR analysis using primers specific for detection of various lineage markers. In all assays, cells cultured in the absence of lineage-inducing cytokines served as controls. The expression levels of lineage markers were first normalized to the expression level of an internal control gene (GAPDH) which is unaffected during differentiation. Differentiation success was then assessed by calculation of the relative expression in the differentiated or the control cells compared to the levels in the parental rat line, using an increase of more than 5-fold in the relative expression as a cut-off for successful differentiation. Differentiated rat MAPCs displayed significant expression of the endothelial markers, von Willebrand factor, and PECAM-1 (top panel); the hepatic markers albumin, cytokeratin-18, and HNF-1a (middle panel); and the neuronal/astrocyte markers GFAP, nestin, and NF-200 (bottom panel).

FIG. 3 is a pair of bar charts showing the low immunogenicity (top panel) and immunosuppressivity (bottom panel) of MAPCs in mixed lymphocyte reactions (MLR), as described further below. In the top panel: B+B=donor B+donor B; B+A=donor B+donor A; B+K=donor B+donor K; B+R=donor B+donor R; B+T=donor B+donor T; donor B+PHA; B+BMPC=donor B+MAPC. The same result was achieved with twelve different donors. In the bottom panel: donor W+donor W; donor W+donor A; donor W+donor T; donor W+MSC; donor W+MAPC (17); donor W+PHA; donor W+donor A+MSC; donor W+donor A+MAPC (17); donor W+donor T+MSC; donor W+donor T+MAPC (17); donor W+donor P+MSC; donor W+donor P+MAPC (17). PHA is phytohemagglutinin (positive control for T-cell activation).

FIG. 4 is a chart showing that MAPCs can suppress the proliferation of ConA stimulated T-cells as described in Example 6. The caption "LN Only" designates the results for control reactions omitting MAPCs. The numbers for MAPCs indicate how many cells were used in the assays.

FIG. 5A is a chart showing the immunosuppressive effects of Lewis MAPCs in mixed lymphocyte reactions, as described in Example 7. The box in FIG. 5A enumerates the number of MAPCs in each reaction. In the box, R designates responder cells and S designates stimulator cells (splenocytes from irradiated DA rats).

Figure 7:
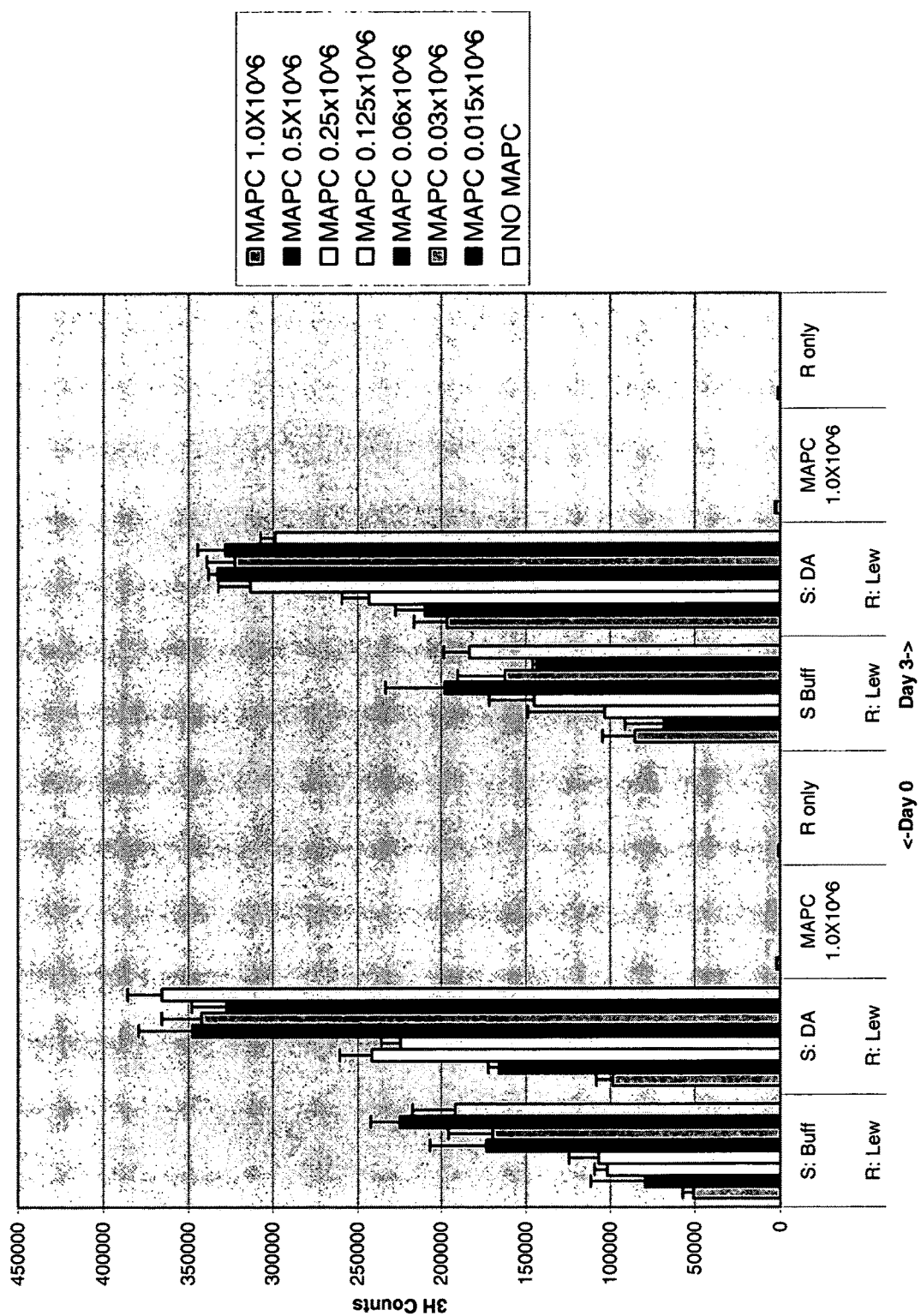

FIG. 7 is a bar chart that depicts the results of an experiment demonstrating the ability of MAPCs to suppress an on-going immune response. The chart shows that MAPCs are strongly immunosuppressive in MLRs, both when they are added at the same time as the T-cell activator (stimulator) (Day 0, left side of chart), and when they are added 3 days after addition of the T-cell activator (stimulator) (Day 3, right side of chart). Details of the experiments are further described in Example 10.

DEFINITIONS

As used herein, certain terms have the meanings set out below.

"A" or "an" means one or more; at least one.

"Adjunctive" means jointly, together with, in addition to, in conjunction with, and the like.

"Co-administer" can include simultaneous or sequential administration of two or more agents.

"Cytokines" refer to cellular factors that induce or enhance cellular movement, such as homing of MAPCs or other stem cells, progenitor cells, or differentiated cells. Cytokines may also stimulate such cells to divide.

"Deleterious" means, as used herein, harmful. By way of illustration, "deleterious immune response" means, as used herein, a harmful immune response, such as those that are lacking or are too weak, those that are too strong, and/or those that are misdirected. Among deleterious immune responses are the harmful immune responses that occur in immune diseases. Examples include the lack of immune responses in immunodeficiency diseases, and the exaggerated and/or misdirected immune responses in autoimmune diseases. Also among deleterious immune responses are immune responses that interfere with medical treatment, including otherwise normal immune responses. Examples include immune responses involved in rejecting transplants and grafts, and the response of immunocompetent cells in transplants and grafts that cause graft versus host disease.

"Differentiation factors" refer to cellular factors, such as growth factors, that induce lineage commitment.

"Dysfunction" means, as used herein, a disorder, disease, or deleterious effect of an otherwise normal process. By way of illustration, an immune dysfunction includes immune diseases, such as autoimmune diseases and immune deficiencies. It also includes immune responses that interfere with medical treatment, including otherwise normal immune responses that interfere with medical treatment. Examples of such dysfunctions include immune responses involved in rejecting transplants and grafts, and the response of immunocompetent cells in transplants and grafts that cause graft versus host disease.

"EC cells" refers to embryonic carcinoma cells.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. For instance, an effective amount of MAPCs could be administered in one or more administrations and could include any preselected amount of cells. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. Thus, for instance, the skilled artisan in this art, such as a physician, based on the known properties of MAPCs as disclosed herein and in the art, together with a consideration of the foregoing factors, will be able to determine the effective amount of MAPCs for a given subject. As used herein, "effective dose" means the same as "effective amount."

"EG cells" refers to embryonal germ cells.

"Engraft" refers to the process of cellular contact and incorporation into an existing tissue of interest in vivo.

"Enriched population" means a relative increase in numbers of MAPCs relative to other cells or constituents in an initial population, such as an increase in numbers of MAPCs relative to one or more non-MAPC cell types in culture, such as primary culture, or in vivo.

"ES cells" refers to embryonal stem cells.

"Expansion" refers to the propagation of a cell or cells without differentiation.

"Fanconi's anemia" as used herein means the same as Fanconi anemia, an inherited disease.

"GVHD" refers to graft versus host disease, which means processes that occur primarily in an immunocompromised host when it is recognized as non-self by immunocompetent cells of a graft.

"HVG" refers to host versus graft response, which means processes which occur when a host rejects a graft. Typically, HVG is triggered when a graft is recognized as foreign (non-self) by immunocompetent cells of the host.

"Isolated" refers to a cell or cells which are not associated with one or more cells or one or more cellular components that are associated with the cell or cells in vivo.

"MAPC" is an acronym for "multipotent adult progenitor cell." It refers to a non-ES, non-EG, non-germ cell that can give rise to cell lineages of more than one germ layer, such as all three germ layers (i.e., endoderm, mesoderm, and ectoderm). MAPCs also may express telomerase. They may be positive for oct-3/4 (e.g., human oct-3A). They also may express rex-1 and rox-1. Further, they may express sox-2, SSEA-4, and/or nanog. The term "adult" in MAPC is not restrictive. It only denotes that these cells are not ES, EG, or germ cells. Typically, as used herein, MAPC is singular and MAPCs is plural. MAPCs also have been referred to as multipotent adult stem cells (MASCs) and as multipotent progenitor cells (MPCs).

MAPCs may constitutively express oct-3/4 and high levels of telomerase (Jiang, Y. et al. (2002) *Nature* 418 (6893): 41; *Exp Hematol.* 30(8): 896. MAPCs derived from human, mouse, rat, or other mammals appear to be the only normal, non-malignant, somatic cells (non-germ cells) known to date to express very high levels of telomerase even in late passage cells. The telomeres are extended in many MAPCs, and MAPCs are karyotypically normal. MAPCs are self-renewing stem cells that can be cultured through many passages without differentiation. They also can be stimulated to differentiate into a wide variety of cells. In addition, MAPCs injected into a mammal can migrate to and assimilate within multiple organs. As such, they have utility in the repopulation of organs, either in a self-renewing state or in a differentiated state compatible with the organ of interest. They have the capacity to replace cell types that could have been damaged, died, or otherwise might have an abnormal function because of genetic or acquired disease. They may contribute to the preservation of healthy cells or production of new cells in a tissue.

"MASC," see MAPC.

"MNC" refers to mononuclear cells.

"Modality" means a type, approach, avenue, or method, such as, a therapeutic modality; i.e., a type of therapy.

"MPC," see MAPC.

"MSC" is an acronym for mesenchymal stem cells.

"Multipotent" with respect to MAPCs, refers to the ability to give rise to cell lineages of more than one germ layer, such as all three primitive germ layers (i.e., endoderm, mesoderm, and ectoderm) upon differentiation.

"Persistence" refers to the ability of cells to resist rejection and remain and/or increase in number over time (e.g., days, weeks, months, or years) in vivo.

"Progenitor" as used in multipotent adult progenitor cells (MAPCs) indicates that these cells can give rise to other cells such as further differentiated cells. The term is not limitative and does not limit these cells to a particular lineage.

"Self-renewal" refers to the ability to produce replicate daughter stem cells having differentiation potential that is identical to those from which they arose. A similar term used in this context is "proliferation."

A "subject" is a vertebrate, such as a mammal, such as a human. Mammals include, but are not limited to, humans, farm animals, sport animals, and pets. Subjects in need of treatment by methods of the present invention include those suffering from a disorder, dysfunction, or disease (such as an immune deficiency or dysfunction, such as HVG and GVHD), or a side effect of the same, or a treatment thereof, that can benefit from administration of MAPCs either as a primary or an adjunctive treatment.

"Transplant" as used herein means to introduce into a subject, cells, tissues, or organs. The transplant can be derived from the subject, from culture, or from a non-subject source.

"Treat," "treating," or "treatment" includes treating, preventing, ameliorating, inhibiting, or curing a deficiency, dysfunction, disease, or other process resulting in a deleterious effect, such as an immune system deficiency, dysfunction, disease, or other process that deleteriously affects immune system functions or properties or that interferes with a therapy.

DETAILED DESCRIPTION OF THE INVENTION

Introduction

The cells described herein (MAPCs) have the ability to regenerate at least two and often all three primitive germ layers (endodermal, mesodermal, and ectodermal) in vitro and in vivo. In this context they are equivalent to embryonal stem cells and distinct from mesenchymal stem cells. The biological potency of MAPCs has been proven in various animal models, including mouse, rat, and xenogeneic engraftment of human stem cells in rats and NOD/SCID mice (Reyes, M. and C. M. Verfaillie (2001) *Ann N Y Acad Sci.* 938: 231-3, discussion pp. 233-5; Jiang, Y. et al. (2002) *Exp Hematol.* 30(8): 896-904).

The clonal potency of MAPCs has been conclusively demonstrated by injecting single genetically marked MAPCs into mouse blastocysts, implanting the blastocysts, and allowing the embryos to develop to term (Jiang, Y. et al. (2002) *Nature* 418(6893): 41-9). Post-natal marker analysis showed that all of the animals were highly chimeric and that the single injected MAPCs proliferated to form differentiated cells of all tissues and organs. No abnormalities or organ dysfunction were observed in any of the animals.

Accordingly, MAPCs are very promising for treating disease by cell transplantation techniques, such as for tissue and organ regeneration, both when used alone and when used in combination with other treatments. Among the potential obstacles to realizing the promise of MAPCs for treating diseases, and for tissue and organ regeneration, are the adverse immune reactions that typically complicate or prevent success in transplantation therapies, such as blood and bone marrow transplantation therapies and solid organ transplantation. Prominent among these immune complications are graft rejection by a host's immune system (referred to herein as host versus graft response and as "HVG") and systemic damage to an immunocompromised host that results when immunocompetent cells in a graft are activated by contact with non-self components of the host (referred to herein as graft versus host disease and as "GVHD").

It has been found (as described in greater detail elsewhere herein) that MAPCs do not provoke an immune response in allogeneic hosts. Thus, transplantation of MAPCs to an allogeneic host should not engender allogeneic graft rejection (i.e., HVG).

Furthermore, it has also been found that allogeneic MAPCs can be administered to a host at high concentration without deleterious effects on respiration, suggesting that undue clumping and/or deposition in the lungs does not occur.

In addition, it has been found (as described in greater detail elsewhere herein) that MAPCs can modulate immune responses. In particular in this regard, it has been found that MAPCs can suppress immune responses, including but not limited to immune responses involved in, for example, HVG and GVHD, to name just two. In an even more detailed particular in this regard, it has been found that MAPCs can suppress proliferation of T-cells, even in the presence of potent T-cell stimulators, such as Concanavalin A and allogeneic stimulator cells.

Moreover, it has been found that even relatively small amounts of MAPCs can suppress these responses. Indeed, only 3% MAPCs in mixed lymphocyte reactions is sufficient to reduce T-cell response to potent stimulators by 50% in vitro.

Accordingly, in certain aspects of the invention in this regard, certain of the embodiments provide compositions and methods and the like for treating, ameliorating, and/or curing or eliminating, adverse immune reactions, such as those that occur in transplantation therapies.

The low immunogenicity of allogeneic MAPCs, their ability to suppress adverse immune responses, and their high specific activity makes them particularly valuable for adjunctive therapies in the treatment of diseases with an adverse immune component. Among such diseases are autoimmune diseases in which, typically, dysfunction of the subject's own immune system causes disease. MAPCs also are useful as immunosuppressive adjunctive therapeutics for treating adverse immune responses that occur in transplantation therapy. Examples include HVG in immunocompetent hosts and GVHD in immunocompromised hosts. MAPCs further can be useful in adjunctive immunosuppressive therapy in the treatment of a variety of neoplasms, anemias and blood disorders, and in the treatment of certain inflammatory diseases. Diseases in this regard are discussed in greater detail below.

Using the methods described herein for MAPC isolation, characterization, and expansion, together with the disclosure herein on immune-suppressing properties of MAPCs, MAPCs can be used to prevent, suppress, or diminish immune disorders, dysfunctions, or diseases, including, for example, adverse immune reactions, such as those that result from other therapies, including those that complicate transplantation therapies, such as HVG and GVHD. Such disorders, dysfunctions, and diseases also include congenital immune disorders and autoimmune diseases, among others.

MAPCs are useful in these regards and others both as primary and adjunctive therapeutic agents and modalities. MAPCs can be used therapeutically alone or together with other agents. MAPCs can be administered before, during, and/or after such agents. Likewise, whether used alone or with other agents, MAPCs can be administered before, during, and/or after a transplant. If administered during transplant, MAPCs can be administered together with the transplant material or separately. If separately administered, the MAPCs can be administered sequentially or simultaneously with the transplant. Furthermore, MAPCs may be administered in advance of the transplant and/or after the transplant.

Other agents that can be used in conjunction with MAPCs, in transplantation therapies in particular, include immunomodulatory agents. A variety of such agents are described elsewhere herein. In certain embodiments of the invention, the immunomodulatory agents are immunosuppressive agents, such as those described elsewhere herein. Among such agents are corticosteroids, cyclosporin A, cyclosporin-like immunosuppressive compounds, azathioprine, cyclophosphamide, and methotrexate.

MAPCs can be administered to hosts by a variety of methods as discussed elsewhere herein. In certain embodiments the MAPCs are administered by injection, such as by intravenous injection. In some embodiments MAPCs are encapsulated for administration. In some embodiments the MAPCs are administered in situ. Examples include in situ administration of MAPCs in solid organ transplantation and in organ repair. These and other forms of administration are discussed below.

In some embodiments of the invention, MAPCs are administered in doses measured by the ratio of MAPCs (cells) to body mass (weight). Alternatively, MAPCs can be administered in doses of a fixed number of cells. Dosing, routes of administration, formulations, and the like are discussed in greater detail elsewhere herein.

Mechanisms of Action

Without being limited to any one or more explanatory mechanisms for the immunomodulatory and other properties, activities, and effects of MAPCs, it is worth nothing that they can modulate immune responses through a variety of modalities. For instance, MAPCs can have direct effects on a graft or host. Such direct effects are primarily a matter of direct contact between MAPCs and cells of the host or graft. The contact may be with structural members of the cells or with constituents in their immediate environment. Such direct mechanisms may involve direct contact, diffusion, uptake, or other processes well known to those skilled in the art. The direct activities and effects of the MAPCs may be limited spatially, such as to an area of local deposition or to a bodily compartment accessed by injection.

MAPCs also can "home" in response to "homing" signals, such as those released at sites of injury or disease. Since homing often is mediated by signals whose natural function is to recruit cells to the sites where repairs are needed, the homing behavior can be a powerful tool for concentrating MAPCs to therapeutic targets. This effect can be stimulated by specific factors, as discussed below.

MAPCs may also modulate immune processes by their response to factors. This may occur additionally or alternatively to direct modulation. Such factors may include homing factors, mitogens, and other stimulatory factors. They may also include differentiation factors, and factors that trigger particular cellular processes. Among the latter are factors that cause the secretion by cells of other specific factors, such as those that are involved in recruiting cells, such as stem cells (including MAPCs), to a site of injury or disease.

MAPCs may, in addition to the foregoing or alternatively thereto, secrete factors that act on endogenous cells, such as stem cells or progenitor cells. The factors may act on other cells to engender, enhance, decrease, or suppress their activities. MAPCs may secrete factors that act on stem, progenitor, or differentiated cells causing those cells to divide and/or differentiate. MAPCs that home to a site where repair is needed may secrete trophic factors that attract other cells to the site. In this way, MAPCs may attract stem, progenitor, or differentiated cells to a site where they are needed. MAPCs also may secrete factors that cause such cells to divide or differentiate.

Secretion of such factors, including trophic factors, can contribute to the efficacy of MAPCs in, for instance, limiting inflammatory damage, limiting vascular permeability, improving cell survival, and engendering and/or augmenting homing of repair cells to sites of damage. Such factors also may affect T-cell proliferation directly. Such factors also may affect dendritic cells, by decreasing their phagocytic and antigen presenting activities, which also may affect T-cell activity By these and other mechanisms, MAPCs can provide beneficial immunomodulatory effects, including, but not limited to, suppression of undesirable and/or deleterious immune reactions, responses, functions, diseases, and the like. MAPCs in various embodiments of the invention provide beneficial immunomodulatory properties and effects that are useful by themselves or in adjunctive therapy for precluding, preventing, lessening, decreasing, ameliorating, mitigating, treating, eliminating and/or curing deleterious immune processes and/or conditions. Such processes and conditions include, for instance, autoimmune diseases, anemias, neoplasms, HVG, GVHD, and certain inflammatory disorders, as described in greeter detail elsewhere herein. MAPCs are useful in these other regards particularly in mammals. In various embodiments of the invention in this regard, MAPCs are used therapeutically in human patients, often adjunctively to other therapies.

MAPC Administration

MAPC Preparations

MAPCs can be prepared from a variety of tissues, such as bone marrow cells, as discussed in greater detail elsewhere herein. Initially the tissue isolates from which the MAPCs are isolated comprise a mixed populations of cells. MAPCs constitute a very small percentage in these initial populations. They must be purified away from the other cells before they can be expanded in culture sufficiently to obtain enough cells for therapeutic applications.

In many embodiments the MAPC preparations are clonally derived. In principle, the MAPCs in these preparations are genetically identical to one another and, if properly prepared and maintained, are free of other cells.

In some embodiments MAPC preparations that are less pure than these may be used. While rare, less pure populations may arise when the initial cloning step requires more than one cell. If these are not all MAPCs, expansion will produce a mixed population in which MAPCs are only one of at least two types of cells. More often mixed populations arise when MAPCs are administered in admixture with one or more other types of cells.

In many embodiments the purity of MAPCs for administration to a subject is about 100%. In other embodiments it is 95% to 100%. In some embodiments it is 85% to 95%. Particularly in the case of admixtures with other cells, the percentage of MAPCs can be 25%-30%, 30%-35%, 35%-40%, 40%-45%, 45%-50%, 60%-70%, 70%-80%, 80%-90%, or 90%-95%.

The number of MAPCs in a given volume can be determined by well known and routine procedures and instrumentation. The percentage of MAPCs in a given volume of a mixture of cells can be determined by much the same procedures. Cells can be readily counted manually or by using an automatic cell counter. Specific cells can be determined in a given volume using specific staining and visual examination and by automated methods using specific binding reagent, typically antibodies, fluorescent tags, and a fluorescence activated cell sorter.

MAPC immunomodulation may involve undifferentiated MAPCs. It may involve MAPCs that are committed to a differentiation pathway. Such immunomodulation also may involve MAPCs that have differentiated into a less potent stem cell with limited differentiation potential. It also may involve MAPCs that have differentiated into a terminally differentiated cell type. The best type or mixture of MAPCs will be determined by the particular circumstances of their use, and it will be a matter of routine design for those skilled in the art to determine an effective type or combination of MAPCs.

Formulations

The choice of formulation for administering MAPCs for a given application will depend on a variety of factors. Prominent among these will be the species of subject, the nature of the disorder, dysfunction, or disease being treated and its state and distribution in the subject, the nature of other therapies and agents that are being administered, the optimum route for administration of the MAPCs, survivability of MAPCs via the route, the dosing regimen, and other factors that will be apparent to those skilled in the art. In particular, for instance, the choice of suitable carriers and other additives will depend on the exact route of administration and the nature of the particular dosage form, for example, liquid dosage form (e.g., whether the composition is to be formulated into a solution, a suspension, gel or another liquid form, such as a time release form or liquid-filled form).

For example, cell survival can be an important determinant of the efficacy of cell-based therapies. This is true for both primary and adjunctive therapies. Another concern arises when target sites are inhospitable to cell seeding and cell growth. This may impede access to the site and/or engraftment there of therapeutic MAPCs. Various embodiments of the invention comprise measures to increase cell survival and/or to overcome problems posed by barriers to seeding and/or growth.

Examples of compositions comprising MAPCs include liquid preparations, including suspensions and preparations for intramuscular or intravenous administration (e.g., injectable administration), such as sterile suspensions or emulsions. Such compositions may comprise an admixture of MAPCs with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Compositions of the invention often are conveniently provided as liquid preparations, e.g., isotonic aqueous solutions, suspensions, emulsions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

Various additives often will be included to enhance the stability, sterility, and isotonicity of the compositions, such as antimicrobial preservatives, antioxidants, chelating agents, and buffers, among others. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents that delay absorption, for example, aluminum monostearate, and gelatin. According to the present invention, however, any vehicle, diluent, or additive used would have to be compatible with the cells.

MAPC solutions, suspensions, and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose) may also be present.

Typically, the compositions will be isotonic, i.e., they will have the same osmotic pressure as blood and lacrimal fluid when properly prepared for administration.

The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or cell stabilizer can be employed to increase the life of MAPC compositions. If such preservatives are included, it is well within the purview of the skilled artisan to select compositions that will not affect the viability or efficacy of the MAPCs.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells utilized in practicing the present invention in the required amount of the appropriate solvent with various amounts of the other ingredients, as desired.

In some embodiments, MAPCs are formulated in a unit dosage injectable form, such as a solution, suspension, or emulsion. Pharmaceutical formulations suitable for injection of MAPCs typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

For any composition to be administered to an animal or human, and for any particular method of administration, it is preferred to determine therefore: toxicity, such as by determining the lethal dose (LD) and LD50 in a suitable animal model, e.g., rodent such as mouse or rat; and, the dosage of the composition(s), concentration of components therein, and timing of administering the composition(s), which elicit a suitable response. Such determinations do not require undue experimentation from the knowledge of the skilled artisan, this disclosure, and the documents cited herein. And, the time for sequential administrations can be ascertained without undue experimentation.

In some embodiments MAPCs are encapsulated for administration, particularly where encapsulation enhances the effectiveness of the therapy, or provides advantages in handling and/or shelf life. Encapsulation in some embodiments where it increases the efficacy of MAPC mediated immunosuppression may, as a result, also reduce the need for immunosuppressive drug therapy.

Also, encapsulation in some embodiments provides a barrier to a subject's immune system that may further reduce a subject's immune response to the MAPCs (which generally are not immunogenic or are only weakly immunogenic in allogeneic transplants), thereby reducing any graft rejection or inflammation that might occur upon administration of the cells.

In a variety of embodiments where MAPCs are administered in admixture with cells of another type, which are more typically immunogenic in an allogeneic or xenogeneic setting, encapsulation may reduce or eliminate adverse host immune responses to the non-MAPC cells and/or GVHD that might occur in an immunocompromised host if the admixed cells are immunocompetent and recognize the host as non-self.

MAPCs may be encapsulated by membranes, as well as capsules, prior to implantation. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval.

A wide variety of materials may be used in various embodiments for microencapsulation of MAPCs. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation of cells that may be used for administration of MAPCs are known to those of skill in the art and are described, for example, in Chang, P., et al., 1999; Matthew, H. W., et al., 1991; Yanagi, K., et al., 1989; Cai Z. H., et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of MAPCs.

Certain embodiments incorporate MAPCs into a polymer, such as a biopolymer or synthetic polymer. Examples of biopolymers include, but are not limited to, fibronectin, fibin, fibrinogen, thrombin, collagen, and proteoglycans. Other factors, such as the cytokines discussed above, can also be incorporated into the polymer. In other embodiments of the invention, MAPCs may be incorporated in the interstices of a three-dimensional gel. A large polymer or gel, typically, will be surgically implanted. A polymer or gel that can be formulated in small enough particles or fibers can be administered by other common, more convenient, non-surgical routes.

Pharmaceutical compositions of the invention may be prepared in many forms that include tablets, hard or soft gelatin capsules, aqueous solutions, suspensions, and liposomes and other slow-release formulations, such as shaped polymeric gels. Oral liquid pharmaceutical compositions may be in the form of, for example, aqueous or oily suspensions, solutions, emulsions, syrups, or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives. An oral dosage form may be formulated such that cells are released into the intestine after passing through the stomach. Such formulations are described in U.S. Pat. No. 6,306,434 and in the references contained therein.

Pharmaceutical compositions suitable for rectal administration can be prepared as unit dose suppositories. Suitable carriers include saline solution and other materials commonly used in the art.

For administration by inhalation, cells can be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, a means may take the form of a dry powder composition, for example, a powder mix of a modulator and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, cells may be administered via a liquid spray, such as via a plastic bottle atomizer.

Other Active Ingredients

MAPCs may be administered with other pharmaceutically active agents. In some embodiments one or more of such agents are formulated together with MAPCs for administration. In some embodiments the MAPCs and the one or more agents are in separate formulations. In some embodiments the compositions comprising the MAPCs and/or the one or more agents are formulated with regard to adjunctive use with one another.

MAPCs may be administered in a formulation comprising a immunosuppressive agents, such as any combination of any number of a corticosteroid, cyclosporin A, a cyclosporin-like immunosuppressive agent, cyclophosphamide, antithymocyte globulin, azathioprine, rapamycin, FK-506, and a macrolide-like immunosuppressive agent other than FK-506 and rapamycin. In certain embodiments, such agents include a corticosteroid, cyclosporin A, azathioprine, cyclophosphamide, rapamycin, and/or FK-506. Immunosuppressive agents in accordance with the foregoing may be the only such additional agents or may be combined with other agents, such as other agents noted herein. Other immunosuppressive agents include Tacrolimus, Mycophenolate mofetil, and Sirolimus.

Such agents also include antibiotic agents, antifungal agents, and antiviral agents, to name just a few other pharmacologically active substances and compositions that may be used in accordance with embodiments of the invention.

Typical antibiotics or anti-mycotic compounds include, but are not limited to, penicillin, streptomycin, amphotericin, ampicillin, gentamicin, kanamycin, mycophenolic acid, nalidixic acid, neomycin, nystatin, paromomycin, polymyxin, puromycin, rifampicin, spectinomycin, tetracycline, tylosin, zeocin, and cephalosporins, aminoglycosides, and echinocandins.

Further additives of this type relate to the fact that MAPCs, like other stems cells, following administration to a subject may "home" to an environment favorable to their growth and function. Such "homing" often concentrates the cells at sites where they are needed, such as sites of immune disorder, dysfunction, or disease. A number of substances are known to stimulate homing. They include growth factors and trophic signaling agents, such as cytokines. They may be used to promote homing of MAPCs to therapeutically targeted sites. They may be administered to a subject prior to treatment with MAPCs, together with MAPCs, or after MAPCs are administered.

Certain cytokines, for instance, alter or affect the migration of MAPCs or their differentiated counterparts to sites in need of therapy, such as immunocompromised sites. Cytokines that may be used in this regard include, but are not limited to, stromal cell derived factor-1 (SDF-1), stem cell factor (SCF), angiopoietin-1, placenta-derived growth factor (PlGF), granulocyte-colony stimulating factor (G-CSF), cytokines that stimulate expression of endothelial adhesion molecules such as ICAMs and VCAMs, and cytokines that engender or facilitate homing.

They may be administered to a subject as a pre-treatment, along with MAPCs, or after MAPCs have been administered, to promote homing to desired sites and to achieve improved therapeutic effect, either by improved homing or by other mechanisms. Such factors may be combined with MAPCs in a formulation suitable for them to be administered together. Alternatively, such factors may be formulated and administered separately.

Order of administration, formulations, doses, frequency of dosing, and routes of administration of factors (such as the cytokines discussed above) and MAPCs generally will vary with the disorder or disease being treated, its severity, the subject, other therapies that are being administered, the stage of the disorder or disease, and prognostic factors, among others. General regimens that have been established for other treatments provide a framework for determining appropriate dosing in MAPC-mediated direct or adjunctive therapy. These, together with the additional information provided herein, will enable the skilled artisan to determine appropriate administration procedures in accordance with embodiments of the invention, without undue experimentation.

Routes

MAPCs can be administered to a subject by any of a variety of routes known to those skilled in the art that may be used to administer cells to a subject.

Among methods that may be used in this regard in embodiments of the invention are methods for administering MAPCs by a parenteral route. Parenteral routes of administration useful in various embodiments of the invention include, among others, administration by intravenous, intraarterial, intracardiac, intraspinal, intrathecal, intraosseous, intraarticular, intrasynovial, intracutaneous, intradermal, subcutaneous, and/or intramuscular injection. In some embodiments intravenous, intraarterial, intracutaneous, intradermal, subcutaneous and/or intramuscular injection are used. In some embodiments intravenous, intraarterial, intracutaneous, subcutaneous, and/or intramuscular injection are used.

In various embodiments of the invention MAPCs are administered by systemic injection. Systemic injection, such as intravenous injection, offers one of the simplest and least invasive routes for administering MAPCs. In some cases, these routes may require high MAPC doses for optimal effectiveness and/or homing by the MAPCs to the target sites. In a variety of embodiments MAPCs may be administered by targeted and/or localized injections to ensure optimum effect at the target sites.

MAPCs may be administered to the subject through a hypodermic needle by a syringe in some embodiments of the invention. In various embodiments, MAPCs are administered to the subject through a catheter. In a variety of embodiments, MAPCs are administered by surgical implantation. Further in this regard, in various embodiments of the invention, MAPCs are administered to the subject by implantation using an arthroscopic procedure. In some embodiments MAPCs are administered to the subject in or on a solid support, such as a polymer or gel. In various embodiments, MAPCs are administered to the subject in an encapsulated form.

In additional embodiments of the invention, MAPCs are suitably formulated for oral, rectal, epicutaneous, ocular, nasal, and/or pulmonary delivery and are administered accordingly.

Dosing

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of MAPCs appropriate to be used in accordance with various embodiments of the invention will depend on numerous factors. It may vary considerably for different circumstances. The parameters that will determine optimal doses of MAPCs to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the MAPCs are syngeneic, autologous, allogeneic, or xenogeneic; their potency (specific activity); the site and/or distribution that must be targeted for the MAPCs to be effective; and such characteristics of the site such as accessibility to MAPCs and/or engraftment of MAPCs. Additional parameters include co-administration with MAPCs of other factors (such as growth factors and cytokines). The optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose of MAPCs outweighs the advantages of the increased dose.

The optimal dose of MAPCs for some embodiments will be in the range of doses used for autologous, mononuclear bone marrow transplantation. For fairly pure preparations of MAPCs, optimal doses in various embodiments will range from $10^4$ to $10^8$ MAPC cells/kg of recipient mass per administration. In some embodiments the optimal dose per administration will be between $10^5$ to $10^7$ MAPC cells/kg. In many embodiments the optimal dose per administration will be $5 \times 10^5$ to $5 \times 10^6$ MAPC cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, MAPCs may be administered in an initial dose, and thereafter maintained by further administration of MAPCs. MAPCs may be administered by one method initially, and thereafter administered by the same method or one or more different methods. The subject's MAPC levels can be maintained by the ongoing administration of the cells. Various embodiments administer the MAPCs either initially or to maintain their level in the subject or both by intravenous injection. In a variety of embodiments, other forms of administration, are used, dependent upon the patient's condition and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regiments can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer MAPCs.

In some embodiments MAPCs are administered to a subject in one dose. In others MAPCs are administered to a subject in a series of two or more doses in succession. In some other embodiments wherein MAPCs are administered in a single dose, in two doses, and/or more than two doses, the doses may be the same or different, and they are administered with equal or with unequal intervals between them.

MAPCs may be administered in many frequencies over a wide range of times. In some embodiments, MAPCs are administered over a period of less than one day. In other embodiment they are administered over two, three, four, five, or six days. In some embodiments MAPCs are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

Therapeutic Uses of Immunomodulating MAPCs

The immunomodulatory properties of MAPCs may be used in treating a wide variety of disorders, dysfunctions and diseases, such as those that, intrinsically, as a secondary effect or as a side effect of treatment, present with deleterious immune system processes and effects. Several illustrations are discussed below.

Many embodiments in this regard involve administering MAPCs to a subject having a weakened (or compromised) immune system, either as the sole therapy or as adjunctive therapy with another treatment. In a variety of embodiments in this regard MAPCs are administered to a subject adjunctively to radiation therapy or chemotherapy or a combination of radiation and chemotherapies that either have been, are being, or will be administered to the subject. In many such embodiments, the radiation therapy, chemotherapy, or a combination of radiation and chemotherapies are part of a transplant therapy. And in a variety of embodiments MAPCs are administered to treat a deleterious immune response, such as HVG or GVHD.

In a variety of embodiments in this regard, the subject is the recipient of a non-syngeneic, typically allogeneic, blood cell or bone marrow cell transplant, the immune system of the subject has been weakened or ablated by radiation therapy, chemotherapy, or a combination of radiation and chemotherapy, immunosuppressive drugs are being administered to the subject, the subject is at risk to develop or has developed graft versus host disease, and MAPCs are administered to the subject adjunctively to any one or more of the transplant, the radiation therapy and/or the chemotherapy, and the immunosuppressive drugs to treat, such as ameliorate, arrest, or eliminate, graft versus host disease in the subject.

Neoplasms

The term "neoplasm" generally denotes disorders involving the clonal proliferation of cells. Neoplasms may be benign, which is to say, not progressive and non-recurrent, and, if so, generally are not life-threatening. Neoplasms also may be malignant, which is to say, that they progressively get worse, spread, and, as a rule, are life threatening and often fatal.

In various embodiments, MAPCs are administered to a subject suffering from a neoplasm, adjunctive to a treatment thereof. For example, in some embodiments of the invention in this regard, the subject is at risk for or is suffering from a neoplasm of blood or bone marrow cells and has undergone or will undergo a blood or bone marrow transplant. Using the methods described herein for MAPC isolation, characterization, and expansion, together with the disclosures herein on immune-suppressing properties of MAPCs, MAPCs are administered to treat, such as to prevent, suppress, or diminish, the deleterious immune reactions, such as HVG and GVHD, that may complicate the transplantation therapy.

In a variety of embodiments involving transplant therapies, MAPCs can be used alone for an immunosuppressive purpose, or together with other agents. MAPCs can be administered before, during, or after one or more transplants. If administered during transplant, MAPCs can be administered separately or together with transplant material. If separately administered, the MAPCs can be administered sequentially or simultaneously with the other transplant materials. Furthermore, MAPCs may be administered well in advance of the transplant and/or well after, alternatively to or in addition to administration at or about the same time as administration of the transplant.

Other agents that can be used in conjunction with MAPCs, in transplantation therapies in particular, include immunomodulatory agents, such as those described elsewhere herein, particularly immunosuppressive agents, more particularly those described elsewhere herein, especially in this regard, one or more of a corticosteroid, cyclosporin A, a cyclosporin-like immunosuppressive compound, azathioprine, cyclophosphamide, methotrexate, and an immunosuppressive monoclonal antibody agent.

Among neoplastic disorders of bone marrow that are treated with MAPCs in embodiments of the invention in this regard are myeloproliferative disorders ("MPDs"); myelodysplastic syndromes (or states) ("MDSs"), leukemias, and lymphoproliferative disorders including multiple myeloma and lymphomas.

MPDs are distinguished by aberrant and autonomous proliferation of cells in blood marrow. The disorder may involve only one type of cell or several. Typically, MPDs involve three cell lineages and are erythrocytic, granulocytic, and thrombocytic. Involvement of the three lineages varies from one MPD to another and between occurrences of the individual types. Typically, they are differently affected and one cell lineage is affected predominately in a given neoplasm. MPDs are not clearly malignant; but, they are classified as neoplasms and are characterized by aberrant, self-replication of hematopoietic precursor cells in blood marrow. MPDs have the potential, nonetheless, to develop into acute leukemias.

MDSs like MPDs are clonal disorders, and they are characterized by aberrant, self-replication of hematopoietic precursor cells in blood marrow. Like MPDs, they can develop into acute leukemias. Most, but not all, MDSs manifest peripheral blood cytopenias (chronic myelomonocytic leukemia is the exception), whereas MPDs do not.

The laboratory and clinical manifestations of these disorders may vary with their course and between individual occurrences. Manifestations can overlap, and it can be difficult to make a certain diagnosis that distinguishes one disease from all the others. Diagnosis of neoplasms of bone marrow hematopoietic cells thus requires special caution, so as to not misdiagnose as a benign disorder one that is, in reality, deadly malignant.

The following diseases are among the myeloproliferative disorders (MPDs) that may be treated with MAPCs, typically or adjunctively, in various embodiments of the invention: chronic myelocytic leukemia ("CML")/chronic granulocytic leukemia ("CGL"), agnogenic myelofibrosis, essential thrombocythemia, and polycythemia vera The following diseases are among the myelodysplastic syndromes (MDSs) that may be treated with MAPCs, typically or adjunctively, in various embodiments of the invention: refractory anemia, refractory anemia with ringed sideroblasts, refractory anemia with excess blasts, refractory anemia with excess blasts in transformation, and chronic myelomonocytic leukemia.

The following diseases are among the lymphoproliferative disorders, including multiple myelomas and lymphomas that may be treated with MAPCs, typically adjunctively, in various embodiments of the invention: pre-B acute lymphoblastic leukemia, chronic lymphocytic leukemia ("CLL"), B-cell lymphoma, hairy cell leukemia, myeloma, multiple myeloma, T-acute lymphoblastic leukemia, peripheral T-cell lymphoma, other lymphoid leukemias, and other lymphomas.

Also among neoplasms that may be treated with MAPCs, typically adjunctively, in a variety of embodiments of the invention are the following: a benign neoplasm of bone marrow cells, a myeloproliferative disorder, a myelodysplastic syndrome, or an acute leukemia; chronic myelocytic leukemia ("CML") (also called chronic granulocytic leukemia ("CGL")), agnogenic myelofibrosis, essential thrombocythemia, polycythemia vera, other myeloproliferative disorders, acute multiple myeloma, myeloblastic leukemia, acute promyelocytic leukemia, pre-B acute lymphoblastic leukemia, chronic lymphocytic leukemia ("CLL"), B-cell lymphoma, hairy cell leukemia, myeloma, T-acute lymphoblastic leukemia, peripheral T-cell lymphoma, other lymphoid leukemias, other lymphomas, or other acute leukemia.

MAPCs may be administered adjunctively to a treatment for any of the foregoing diseases.

Treatments Involving Immunoablation or Compromise

Acute leukemias often are difficult to treat by methods that have been effective for other malignancies. This is partly due to the mobility of cells from bone marrow, including those of a neoplasm. Partly it may be due to the diffuse distribution of bone marrow throughout the skeleton. And partly it is due, no doubt, to the nature of the cells themselves and their transformation.

At present, a standard treatment for hematologic malignancies involves ablating all hematopoietic cells in the patient. There is no way to do this without also ablating the patient's healthy hematopoietic cells. Typically, the patient is treated using chemo-radiotherapy in sufficiently high doses to kill virtually all bone marrow cells, both normal and neoplastic. The treatment's side effects are severe, and its effects on patients are unpleasant, painful, and physically and emotionally debilitating. The treatment not only ablates the diseased tissue and cells, it also eviscerates the patient's hematopoietic system and immune system. The treatment leaves them compromised, dependent on transfusions, and so highly susceptible to infection that even an otherwise minor exposure to an infectious agent can be fatal.

Normal hematopoietic capacity is restored thereafter by either autologous or allogeneic peripheral blood or bone marrow transplants. Unfortunately, the patient's immune system not only is severely compromised by the ablative treatment, but, also in the case of allogeneic transplantation, by intentional immune suppression to prevent rejection of the transplant and ensure engraftment and proliferation of the new hematopoietic stem cells that will repopulate the patient's marrow and regenerate the patient's hematopoietic and immune systems.

Many complications have been encountered in carrying out such transplants to regenerate the hematopoietic and immune systems in an immunocompromised host. One is rejection by residual immune competent cells and processes in the host, referred to herein as HVG response. Another is triggered by immunocompetent cells in the graft, referred to herein as GVHD.

These complications might be avoided by using syngeneic or autologous donor material. However, syngeneic donors generally are rare and autologous transplants have a high risk of disease recurrence. Hence, transplants generally use allogeneic cells and tissues obtained from an HLA compatible donor. Unfortunately this procedure results in GVHD, ranging from mild to severe in the preponderance of those receiving this form of therapy. If not at least ameliorated, these immune reactions will result in failure of the transplant therapy, and may themselves be fatal to the patient.

A variety of agents have been developed to suppress immune responses that ameliorate graft complications, such as HVG and GVHD, as discussed herein above. Some are sufficiently effective to reduce adverse immune reactions to a manageable level in some transplant therapies, such as bone marrow and peripheral blood transplantation. These agents have improved the prognosis for transplant patients, to some extent; but, none of them is fully effective, and all of them have rather substantial shortcomings.

It has been found (as described in greater detail elsewhere herein) that MAPCs do not provoke an immune response in allogeneic hosts. Transplantation of MAPCs to an allogeneic host does not, thus, engender allogeneic graft rejection (i.e., HVG).

Furthermore, it has also been found that allogeneic MAPCs can be administered to a host at high concentration without deleterious effects on respiration.

In addition, it has been found, (as described in greater detail elsewhere herein) that MAPCs can modulate immune responses. In particular in this regard, it has been found that MAPCs can suppress immune responses, including but not limited to immune responses involved in, for example, HVG response and GVHD, to name just two. In an even more detailed particular in this regard, it has been found that MAPCs can suppress proliferation of T-cells, even in the presence of potent T-cell stimulators, such as Concanavalin A and allogeneic or xenogeneic stimulator cells.

Moreover, it has been found that even relatively small amounts of MAPCs can suppress these responses. Indeed, only 3% MAPCs in mixed lymphocyte reactions is sufficient to reduce T-cell response by 50% in vitro.

Accordingly, embodiments of the invention provide compositions and methods and the like for treating, such as for ameliorating, and/or curing or eliminating, neoplasms, such as neoplasms of hematopoietic cells, particularly those of bone marrow.

Among these are those that are myeloproliferative disorders (MPDs), such as chronic myelocytic leukemia (also called "chronic granulocytic leukemia" and "CGL"), agnogenic myelofibrosis, essential thrombocythemia, polycythemia vera; myelodysplastic syndromes (MDSs), such as refractory anemia, refractory anemia with ringed sideroblasts, refractory anemia with excess blasts, refractory anemia with excess blasts in transformation, chronic myelomonocytic leukemia; and clearly malignant neoplasms—the acute leukemias—such as acute myeloblastic leukemia, chronic myelogenous leukemia (CML), acute promyelocytic leukemia, B-acute lymphoblastic leukemia, CLL, B-cell lymphoma, hairy cell leukemia, myeloma, T-acute lymphoblastic leukemia, peripheral T-cell lymphoma, and other lymphoid leukemias and lymphomas.

MAPCs may be administered adjunctively to a treatment for any of the foregoing diseases.

Anemias and Other Disorders of the Blood

In various embodiments of the invention, MAPCs may be used to treat an anemia or other blood disorder, often adjunctively. Among various embodiments in this regard are embodiments in which MAPCs are used to treat the following anemias and/or blood disorders, either solely or, typically, adjunctively: hemoglobinopathies, thalassemia, bone marrow failure syndrome, sickle cell anemia, aplastic anemia, or an immune hemolytic anemia. Also, disorders include refractory anemia, refractory anemia with ringed sideroblasts, refractory anemia with excess blasts, refractory anemia with excess blasts in transformation, chronic myelomonocytic leukemia, or other myelodysplastic syndrome, and in some embodiments, Fanconi's anemia.

MAPCs may be administered adjunctively to a treatment for any of the foregoing diseases.

Immune Diseases

Embodiments of the invention relate to using MAPC immunomodulation to treat an immune dysfunction, disorder, or disease, either solely, or as an adjunctive therapy. Embodiments in this regard relate to congenital immune deficiencies and autoimmune dysfunctions, disorders, and diseases. Various embodiments relate, in this regard, to using MAPCs to treat, solely or adjunctively, Crohn's disease, Guillain-Barré syndrome, lupus erythematosus (also called "SLE" and systemic lupus erythematosus), multiple sclerosis, myasthenia gravis, optic neuritis, psoriasis, rheumatoid arthritis, Graves' disease, Hashimoto's disease, Ord's thyroiditis, diabetes mellitus (type 1), Reiter's syndrome, autoimmune hepatitis, primary biliary cirrhosis, antiphospholipid antibody syndrome ("APS"), opsoclonus-myoclonus syndrome ("OMS"), temporal arteritis, acute disseminated encephalomyelitis ("ADEM" and "ADE"), Goodpasture's, syndrome, Wegener's granulomatosis, celiac disease, pemphigus, polyarthritis, and warm autoimmune hemolytic anemia.

Particular embodiments among these relate to Crohn's disease, lupus erythematosus (also called "SLE" and systemic lupus erythematosus), multiple sclerosis, myasthenia gravis, psoriasis, rheumatoid arthritis, Graves' disease, Hashimoto's disease, diabetes mellitus (type 1), Reiter's syndrome, primary biliary cirrhosis, celiac disease, polyarthritis, and warm autoimmune hemolytic anemia.

In addition, MAPCs are used in a variety of embodiments in this regard, solely and, typically, adjunctively, to treat a variety of diseases thought to have an autoimmune component, including but not limited to embodiments that may be used to treat endometriosis, interstitial cystitis, neuromyotonia, scleroderma, progressive systemic scleroderma, vitiligo, vulvodynia, Chagas' disease, sarcoidosis, chronic fatigue syndrome, and dysautonomia.

Inherited immune system disorders include Severe Combined Immunodeficiency (SCID) including but not limited to SCID with Adenosine Deaminase Deficiency (ADA-SCID), SCID which is X-linked, SCID with absence of T & B Cells, SCID with absence of T Cells, Normal B Cells, Omenn Syndrome, Neutropenias including but not limited to Kostmann Syndrome, Myelokathexis; Ataxia-Telangiectasia, Bare Lymphocyte Syndrome, Common Variable Immunodeficiency, DiGeorge Syndrome, Leukocyte Adhesion Deficiency; and phagocyte Disorders (phagocytes are immune system cells that can engulf and kill foreign organisms) including but not limited to Chediak-Higashi Syndrome, Chronic Granulomatous Disease, Neutrophil Actin Deficiency, Reticular Dysgenesis.

MAPCs may be administered adjunctively to a treatment for any of the foregoing diseases.

Inflammatory Diseases

Additionally, in a variety of embodiments of the invention, MAPCs may be used to treat inflammatory diseases, either as a sole agent or adjunctively. In many such embodiments MAPCs may be used to treat serious inflammatory states, such as those that arise from acute allergic reaction, or ancillary to other diseases or treatments. For the most part, at present, the use of MAPCs in this regard is limited to acute cases in which the subject is at risk of great incapacity or loss or life.

MAPCs may be administered adjunctively to a treatment for any of the foregoing diseases.

MAPCs as Described in PCT/US00/21387

Human MAPCs are described in U.S. patent application Ser. No. 10/048,757 (PCT/US00/21387 (published as WO 01/11011)) and Ser. No. 10/467,963 (PCT/US02/04652 (published as WO 02/064748)), the contents of which are incorporated herein by reference for their description of MAPCs. MAPCs have been identified in other mammals. Murine MAPCs, for example, are also described in PCT/US00/21387 (published as WO 01/11011) and PCT/US02/04652 (published as WO 02/064748). Rat MAPCs are also described in WO 02/064748.

Isolation and Growth of MAPCs as Described in PCT/US00/21387

Methods of MAPC isolation for humans and mouse are known in the art. They are described in PCT/US00/21387 (published as WO 01/11011) and for rat in PCT/US02/04652 (published as WO 02/064748), and these methods, along with the characterization of MAPCs disclosed therein, are incorporated herein by reference.

MAPCs were initially isolated from bone marrow, but were subsequently established from other tissues, including brain and muscle (Jiang, Y. et al., 2002). Thus, MAPCs can be isolated from multiple sources, including bone marrow, placenta, umbilical cord and cord blood, muscle, brain, liver, spinal cord, blood or skin. For example, MAPCs can be derived from bone marrow aspirates, which can be obtained by standard means available to those of skill in the art (see, for example, Muschler, G. F., et al., 1997; Batinic, D., et al., 1990). It is therefore now possible for one of skill in the art to obtain bone marrow aspirates, brain or liver biopsies, and other organs, and isolate the cells using positive or negative selection techniques available to those of skill in the art, relying upon the genes that are expressed (or not expressed) in these cells (e.g., by functional or morphological assays such as those disclosed in the above-referenced applications, which have been incorporated herein by reference).

MAPCs from Human Bone Marrow as Described in PCT/US00/21387

Bone marrow mononuclear cells were derived from bone marrow aspirates, which were obtained by standard means available to those of skill in the art (see, for example, Muschler, G. F., et al., 1997; Batinic, D., et al., 1990). Multipotent adult stem cells are present within the bone marrow (or other organs such as liver or brain), but do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of CD45+ and Gly-A+ cells, and the remaining approximately 0.1% of marrow mononuclear cells were then recovered. Cells could also be plated in fibronectin-coated wells and cultured as described below for 2-4 weeks to deplete the cells of CD45+ and Gly-A+ cells.

Alternatively, positive selection could be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman et al., eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch et al., 1983 (immunoaffinity chromatography), and Wysocki and Sato, 1978 (fluorescence-activated cell sorting).

Recovered CD45$^-$/GlyA$^-$ cells were plated onto culture dishes coated with 5-115 ng/ml (about 7-10 ng/ml can be used) serum fibronectin or other appropriate matrix coating. Cells were maintained in Dulbecco's Minimal Essential Medium (DMEM) or other appropriate cell culture medium, supplemented with 1-50 ng/ml (about 5-15 ng/ml can be used) platelet-derived growth factor-BB (PDGF-BB), 1-50 ng/ml (about 5-15 ng/ml can be used) epidermal growth factor (EGF), 1-50 ng/ml (about 5-15 ng/ml can be used) insulin-like growth factor (IGF), or 100-10,000 IU (about 1,000 IU can be used) LIF, with $10^{-10}$ to $10^{-8}$ M dexamethasone (or other appropriate steroid), 2-10 µg/ml linoleic acid, and 0.05-0.15 µM ascorbic acid. Other appropriate media include, for example, MCDB, MEM, IMDM, and RPMI. Cells can either be maintained without serum, in the presence of 1-2% fetal calf serum, or, for example, in 1-2% human AB serum or autologous serum.

When re-seeded at $2 \times 10^3$ cells/cm$^2$ every 3 days, >40 cell doublings were routinely obtained, and some populations underwent >70 cell doublings. Cell doubling time was 36-48 h for the initial 20-30 cell doublings. Afterwards cell-doubling time was extended to as much as 60-72 h.

Telomere length of MAPCs from 5 donors (age about 2 years to about 55 years) cultured at re-seeding densities of $2 \times 10^3$ cells/cm$^2$ for 23-26 cell doublings was between 11-13 KB. This was 3-5 KB longer than telomere length of blood lymphocytes obtained from the same donors. Telomere length of cells from 2 donors evaluated after 23 and 25 cell doublings, respectively, and again after 35 cells doublings, was unchanged. The karyotype of these MAPCs was normal.

Phenotype of Human MAPCs Under Conditions Described in PCT/US00/21387

Immunophenotypic analysis by FACS of human MAPCs obtained after 22-25 cell doublings indicated that the cells do not express CD31, CD34, CD36, CD38, CD45, CD50, CD62E and -P, HLA-DR, Muc18, STRO-1, cKit, Tie/Tek; and express low levels of CD44, HLA-class I, and β2-microglobulin, but express CD10, CD13, CD49b, CD49e, CDw90, Flk1 (N>10).

Once cells underwent >40 doublings in cultures re-seeded at about $2 \times 10^3$/cm$^2$, the phenotype became more homogenous, and no cell expressed HLA class-I or CD44 (n=6). When cells were grown at higher confluence, they expressed high levels of Muc18, CD44, HLA class I and β2-microglobulin, which is similar to the phenotype described for MSC (N=8) (Pittenger, 1999).

Immunohistochemistry showed that human MAPCs grown at about $2 \times 10^3$/cm$^2$ seeding density expressed EGF-R, TGF-R1 and -2, BMP-R1A, PDGF-R1a and -B, and that a small subpopulation (between 1 and 10%) of MAPCs stained with anti-SSEA4 antibodies (Kannagi, R, 1983).

Using Clontech cDNA arrays the expressed gene profile of human MAPCs cultured at seeding densities of about $2 \times 10^3$ cells/cm$^2$ for 22 and 26 cell doublings was determined:

A. MAPCs did not express CD31, CD36, CD62E, CD62P, CD44-H, cKit, Tie, receptors for IL1, IL3, IL6, IL11, G CSF, GM-CSF, Epo, Flt3-L, or CNTF, and low levels of HLA-class-I, CD44-E and Muc-18 mRNA.

B. MAPCs expressed mRNA for the cytokines BMP1, BMP5, VEGF, HGF, KGF, MCP1; the cytokine receptors Flk1, EGF-R, PDGF-R1a, gp130, LIF-R, activin-R1 and -R2, TGFR-2, BMP-R1A; the adhesion receptors CD49c, CD49d, CD29; and CD10.

C. MAPCs expressed mRNA for hTRT and TRF1; the POU domain transcription factor oct-4, sox-2 (required with oct-4 to maintain undifferentiated state of ES/EC, Uwanogho D., 1995), sox 11 (neural development), sox 9 (chondrogenesis) (Lefebvre V., 1998); homeodeomain transcription factors: Hox-a4 and -a5 (cervical and thoracic skeleton specification; organogenesis of respiratory tract) (Packer A I, 2000), Hox-a9 (myelopoiesis) (Lawrence H, 1997), Dlx4 (specification of forebrain and peripheral structures of head) (Akimenko M A, 1994), MSX1 (embryonic mesoderm, adult heart and muscle, chondro- and osteogenesis) (Foerst-Potts L. 1997), PDX1 (pancreas) (Offield M F, 1996).

D. Presence of oct-4, LIF-R, and hTRT mRNA was confirmed by RT-PCR.

E. In addition, RT-PCR showed that rex-1 mRNA and rox-1 mRNA were expressed in MAPCs.

Oct-4, rex-1 and rox-1 were expressed in MAPCs derived from human and murine marrow and from murine liver and brain. Human MAPCs expressed LIF-R and stained positive with SSEA-4. Finally, oct-4, LIF-R, rex-1 and rox-1 mRNA levels were found to increase in human MAPCs cultured beyond 30 cell doublings, which resulted in phenotypically more homogenous cells. In contrast, MAPCs cultured at high density lost expression of these markers. This was associated with senescence before 40 cell doublings and loss of differentiation to cells other than chondroblasts, osteoblasts, and adipocytes. Thus, the presence of oct-4, combined with rex-1, rox-1, and sox-2, correlated with the presence of the most primitive cells in MAPCs cultures.

Culturing MAPCs as Described in PCT/US00/21387

MAPCs isolated as described herein can be cultured using methods disclosed herein and in PCT/US00/21387, which is incorporated by reference for these methods.

Briefly, for the culture of MAPCs, culture in low-serum or serum-free medium was preferred to maintain the cells in the undifferentiated state. Serum-free medium used to culture the cells, as described herein, was supplemented as described in Table 1. Human MAPCs do not require LIF.

TABLE 1

| | |
|---|---|
| Insulin | 10-50 μg/ml (10 μg/ml)* |
| Transferrin | 0-10 μg/ml (5.5 μg/ml) |
| Selenium | 2-10 μg/ml (5 ng/ml) |
| Bovine serum albumin (BSA) | 0.1-5 μg/ml (0.5 μg/ml) |
| Linoleic acid | 2-10 μg/ml (4.7 μg/ml) |
| Dexamethasone | 0.005-0.15 μM (.01 μM) |
| L-ascorbic acid 2-phosphate | 0.1 mM |
| Low-glucose DMEM (DMEM-LG) | 40-60% (60%) |
| MCDB-201 | 40-60% (40%) |
| Fetal calf serum | 0-2% |
| Platelet-derived growth | 5-15 ng/ml (10 ng/ml) |
| Epidermal growth factor | 5-15 ng/ml (10 ng/ml) |
| Insulin like growth factor | 5-15 ng/ml (10 ng/ml) |
| Leukemia inhibitory factor | 10-10,000 IU (1,000 IU) |

*Preferred concentrations are shown in parentheses.

Addition of 10 ng/ml LIF to human MAPCs did not affect short-term cell growth (same cell doubling time till 25 cell doublings, level of oct-4 (oct-3/4) expression). In contrast to what was seen with human cells, when fresh murine marrow mononuclear cells, depleted on day 0 of CD45$^+$ cells, were plated in MAPC culture, no growth was seen. When murine marrow mononuclear cells were plated, and cultured cells 14 days later depleted of CD45$^+$ cells, cells with the morphology and phenotype similar to that of human MAPCs appeared. This suggested that factors secreted by hemopoietic cells were needed to support initial growth of murine MAPCs. When cultured with PDGF-BB and EFG alone, cell doubling was slow (>6 days) and cultures could not be maintained beyond 10 cell doublings. Addition of 10 ng/m LIF significantly enhanced cell growth.

Once established in culture, cells could be frozen and stored as frozen stocks, using DMEM with 40% FCS and 10% DMSO. Other methods for preparing frozen stocks for cultured cells are also available to those of skill in the art.

Thus, MAPCs could be maintained and expanded in culture medium that is available to the art. Such media include, but are not limited to Dulbecco's Modified Eagle's Medium® (DMEM), DMEM F12 Medium®, Eagle's Minimum Essential Medium®, F-12K Medium®, Iscove's Modified Dulbecco's Medium® and RPMI-1640 Medium®. Many media are also available as low-glucose formulations, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at 55-65° C. if deemed necessary to inactivate components of the complement cascade. Additional supplements can also be used advantageously to supply the cells with the necessary trace elements for optimal growth and expansion. Such supplements include insulin, transferrin, sodium selenium, and combinations thereof. These components can be included in a salt solution such as, but not limited to, Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin. Antibiotic and antimycotic additives can be of some concern, depending on the type of work being performed. One possible situation that can arise is an antibiotic-containing media wherein bacteria are still present in the culture, but the action of the antibiotic performs a bacteriostatic rather than bacteriocidal mechanism. Also, antibiotics can interfere with the metabolism of some cell types.

Hormones can also be advantageously used in cell culture and include, but are not limited to D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of fastidious cultured cells, particularly ES cells. Feeder cells are normal cells that have been inactivated by γ-irradiation. In culture, the feeder layer serves as a basal layer for other cells and supplies cellular factors without further growth or division of their own (Lim, J. W. and Bodnar, A., 2002). Examples of feeder layer cells are typically human diploid lung cells, mouse embryonic fibroblasts, and Swiss mouse embryonic fibroblasts, but can be any post-mitotic cell that is capable of supplying cellular components and factors that are advantageous in allowing optimal growth, viability, and expansion of stem cells. In many cases, feeder cell layers are not necessary to keep the ES cells in an undifferentiated, proliferative state, as leukemia inhibitory factor (LIF) has anti-differentiation properties. Therefore, supplementation with LIF could be used to maintain MAPC in some species in an undifferentiated state.

Cells in culture can be maintained either in suspension or attached to a solid support, such as extracellular matrix components and synthetic or biopolymers. Stem cells often require additional factors that encourage their attachment to a solid support, such as type I, type II, and type IV collagen, concanavalin A, chondroitin sulfate, fibronectin, "superfibronectin" and fibronectin-like polymers, gelatin, laminin, poly-D and poly-L-lysine, thrombospondin, and vitronectin.

The maintenance conditions of stem cells can also contain cellular factors that allow stem cells, such as MAPCs, to remain in an undifferentiated form. It is advantageous under conditions where the cell must remain in an undifferentiated state of self-renewal for the medium to contain epidermal growth factor (EGF), platelet derived growth factor (PDGF), leukemia inhibitory factor (LIF, in selected species), and combinations thereof. It is apparent to those skilled in the art that supplements that allow the cell to self-renew but not differentiate must be removed from the culture medium prior to differentiation.

Stem cell lines and other cells can benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce, and it is within the capabilities of the skilled artisan to select the appropriate cells for co-culture.

Methods of identifying and subsequently separating differentiated cells from their undifferentiated counterparts can be carried out by methods well known in the art. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e., formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. A preferred embodiment of the invention envisions the use of FACS to identify and separate cells based on cell-surface antigen expression.

Additional Culture Methods

In additional experiments it has been found that the density at which MAPCs are cultured can vary from about 100 cells/cm$^2$ or about 150 cells/cm$^2$ to about 10,000 cells/cm$^2$, including about 200 cells/cm$^2$ to about 1500 cells/cm$^2$ to about 2000 cells/cm$^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 3-5%, can be used at any time during the isolation, growth, and differentiation of MAPCs in culture.

Inducing MAPCs to Differentiate to Form Committed Progenitors and Tissue-Specific Cell Types as Described in PCT/US00/21387

Using appropriate growth factors, chemokines, and cytokines, MAPCs can be induced to differentiate to form a wide variety of cells, including cells of all three embryonic lineages, mesodermal, endodermal, and ectodermal. These methods have been published and are described in U.S. and PCT applications referenced above, which are herein incorporated by reference in their entirety, particularly as to methods for isolating MAPCs, culturing them, inducing them to differentiate, and expanding both undifferentiated and differentiated MAPCs in vitro. The ability to differentiate MAPCs in vitro reflects the multipotency of these cells in vivo, where experiments have shown that they can form virtually all (if not all) cells of an organism.

In particular, the ability of MAPCs to differentiate in vitro into cells of hematopoietic lineage and immune cells has been well demonstrated.

Approaches for Transplantation to Prevent Immune Rejection a. Universal donor cells: MAPCs have cell surface profiles consistent with evasion of immune recognition, and in their natural state may not stimulate immune sensitization and rejection. They may serve as natural universal donor cells even if their progeny mature to cells which ordinarily would be immune-recognized and rejected.

Alternatively, MAPCs also can be manipulated to serve as universal donor cells. MAPCs can be modified to serve as universal donor cells by eliminating HLA-type I and HLA-type II antigens, and potentially introducing the HLA-antigens from the prospective recipient to avoid the cells becoming easy targets for NK-mediated killing, or becoming susceptible to unlimited viral replication and/or malignant transformation. Elimination of HLA-antigens can be accomplished by homologous recombination or via introduction of point-mutations in the promoter region or by introduction of a point mutation in the initial exon of the antigen to introduce a stop-codon, such as with chimeroplasts. Transfer of the host HLA-antigen can be achieved by retroviral, lentiviral, adeno associated virus or other viral transduction or by transfection of the target cells with the HLA-antigen cDNAs. MAPCs can be used to establish a set amount or a given range or level of a protein in the body or blood.

b. Gene therapy: MAPCs can be extracted and isolated from the body, grown in culture in the undifferentiated state or induced to differentiate in culture, and genetically altered using a variety of techniques, especially viral transduction. Uptake and expression of genetic material is demonstrable, and expression of foreign DNA is stable throughout development. Retroviral and other vectors for inserting foreign DNA into stem cells are known to those of skill in the art. (Mochizuki, H., et al. (1998) *J. Virol* 72(11): 8873-8883; Robbins, P., et al. (1997) *J. Virol.* 71(12): 9466-9474; Bierhuizen, M., et al. (1997) *Blood* 90(9): 3304-3315; Douglas, J., et al. (1999) *Hum. Gene Ther.* 10(6): 935-945; Zhang, G., et al. (1996) *Biochem. Biophys. Res. Commun.* 227(3): 707-711). Once transduced using a retroviral vector, enhanced green fluorescent protein (eGFP) expression persists in terminally differentiated muscle cells, endothelium, and c-Kit positive cells derived from the isolated MAPCs, demonstrating that expression of retroviral vectors introduced into MAPC persists throughout differentiation. Terminal differentiation was induced from cultures initiated with 10 eGFP+ cells previously transduced by retroviral vector and sorted a few weeks into the initial MAPC culture period.

Genetically-Modified Stem Cells as Described in PCT/US00/21387

MAPCs can be genetically altered ex vivo, eliminating one of the most significant barriers for gene therapy. For example, a subject's bone marrow aspirate is obtained, and from the aspirate MAPCs are isolated. The MAPCs are then genetically altered to express one or more desired gene products. The MAPCs can then be screened or selected ex vivo to identify those cells which have been successfully altered, and these cells can be reintroduced into the subject, either locally or systemically. Alternately, MAPCs can be genetically altered and cultured to induce differentiation to form a specific cell lineage for transplant. In either case, the transplanted MAPCs provide a stably-transfected source of cells that can express a desired gene product. Especially where the patient's own bone marrow aspirate is the source of the MAPCs, this method provides an immunologically safe method for producing transplant cells.

Methods for Genetically Altering MAPCs as Described in PCT/US00/21387

Cells isolated by the method described herein can be genetically modified by introducing DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer. MAPCs can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

Homologous Recombination as Described in PCT/US00/21387

Calcium phosphate transfection, which relies on precipitates of plasmid DNA/calcium ions, can be used to introduce plasmid DNA containing a target gene or polynucleotide into isolated or cultured MAPCs. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., ProFection® from Promega Corp., Madison, Wis.).

DEAE-dextran transfection, which is also known to those of skill in the art, may be preferred over calcium phosphate transfection where transient transfection is desired, as it is often more efficient.

Since the MAPCs are isolated cells, microinjection can be particularly effective for transferring genetic material into the cells. Briefly, cells are placed onto the stage of a light microscope. With the aid of the magnification provided by the microscope, a glass micropipette is guided into the nucleus to inject DNA or RNA. This method is advantageous because it provides delivery of the desired genetic material directly to the nucleus, avoiding both cytoplasmic and lysosomal degradation of the injected polynucleotide. This technique has been used effectively to accomplish germline modification in transgenic animals.

MAPCs can also be genetically modified using electroporation. The target DNA or RNA is added to a suspension of cultured cells. The DNA/RNA-cell suspension is placed between two electrodes and subjected to an electrical pulse, causing a transient permeability in the cell's outer membrane that is manifested by the appearance of pores across the membrane. The target polynucleotide enters the cell through the open pores in the membrane, and when the electric field is discontinued, the pores close in approximately one to 30 minutes.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPC) can be added. A recommended reagent for liposomal transfer is Lipofectin® (Life Technologies, Inc.), which is commercially available. Lipofectin®, for example, is a mixture of the cationic lipid N-[1-(2,3-dioleyloxy) propyl]-N—N—N-trimethyl ammonia chloride and DOPE. Delivery of linear DNA, plasmid DNA, or RNA can be accomplished either in vitro or in vivo using liposomal delivery, which may be a preferred method due to the fact that liposomes can carry larger pieces of DNA, can generally protect the polynucleotide from degradation, and can be targeted to specific cells or tissues. A number of other delivery systems relying on liposomal technologies are also commercially available, including Effectene™ (Qiagen), DOTAP (Roche Molecular Biochemicals), FuGene 6™ (Roche Molecular Biochemicals), and Transfectam® (Promega). Cationic lipid-mediated gene transfer efficiency can be enhanced by incorporating purified viral or cellular envelope components, such as the purified G glycoprotein of the vesicular stomatitis virus envelope (VSV-G), in the method of Abe, A., et al. (*J. Virol.* (1998) 72: 6159-6163).

Gene transfer techniques which have been shown effective for delivery of DNA into primary and established mammalian cell lines using lipopolyamine-coated DNA can be used to introduce target DNA into MAPCs. This technique is generally described by Loeffler, J. and Behr, J. (*Methods in Enzymology* (1993) 217: 599-618).

Naked plasmid DNA can be injected directly into a tissue mass formed of differentiated cells from the isolated MAPCs. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA.

Microprojectile gene transfer can also be used to transfer genes into MAPCs either in vitro or in vivo. The basic procedure for microprojectile gene transfer was described by J. Wolff (*Gene Therapeutics* (1994) at page 195). Briefly, plasmid DNA encoding a target gene is coated onto microbeads, usually 1-3 micron sized gold or tungsten particles. The coated particles are placed onto a carrier sheet inserted above a discharge chamber. Once discharged, the carrier sheet is accelerated toward a retaining screen. The retaining screen forms a barrier which stops further movement of the carrier sheet while allowing the polynucleotide-coated particles to be propelled, usually by a helium stream, toward a target surface, such as a tissue mass formed of differentiated MAPCs. Microparticle injection techniques have been described previously, and methods are known to those of skill in the art (see Johnston, S. A., et al. (1993) *Genet. Eng.* (*NY*) 15: 225-236; Williams, R. S., et al. (1991) *Proc. Natl. Acad. Sci. USA* 88: 2726-2730; Yang, N. S., et al. (1990) *Proc. Natl. Acad. Sci. USA* 87: 9568-9572).

Signal peptides can be attached to plasmid DNA, as described by Sebestyen, et al. (*Nature Biotech.* (1998) 16: 80-85), to direct the DNA to the nucleus for more efficient expression.

Viral vectors are used to genetically alter MAPCs and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors which can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Retroviral vectors are effective for transducing rapidly-dividing cells, although a number of retroviral vectors have been developed to effectively transfer DNA into non-dividing cells as well (Mochizuki, H., et al. (1998) *J. Virol.* 72: 8873-8883). Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector which is ecotropic, xenotropic, or amphotropic, providing a degree of specificity for retroviral vector systems.

A retroviral DNA vector is generally used with the packaging cell line to produce the desired target sequence/vector combination within the cells. Briefly, a retroviral DNA vector is a plasmid DNA which contains two retroviral LTRs positioned about a multicloning site and SV40 promoter so that a first LTR is located 5' to the SV40 promoter, which is operationally linked to the target gene sequence cloned into the multicloning site, followed by a 3' second LTR. Once formed, the retroviral DNA vector can be transferred into the packaging cell line using calcium phosphate-mediated transfection, as previously described. Following approximately 48 hours of virus production, the viral vector, now containing the target gene sequence, is harvested.

Targeting of retroviral vectors to specific cell types was demonstrated by Martin, F., et al., (*J. Virol.* (1999) 73: 6923-6929), who used a single-chain variable fragment antibody directed against the surface glycoprotein high-molecular-weight melanoma-associated antigen fused to the amphotropic murine leukemia virus envelope to target the vector to deliver the target gene to melanoma cells. Where targeted delivery is desired, as, for example, when differentiated cells are the desired objects for genetic alteration, retroviral vectors fused to antibody fragments directed to the specific markers expressed by each cell lineage differentiated from the MAPCs can be used to target delivery to those cells.

Lentiviral vectors are also used to genetically alter MAPCs. Many such vectors have been described in the literature and are known to those of skill in the art (Salmons, B. and Gunzburg, W. H. (1993) *Hum. Gene Therapy* 4: 129-141. These vectors have been effective for genetically altering human hematopoietic stem cells (Sutton, R., et al. (1998) *J. Virol.* 72: 5781-5788). Packaging cell lines have been described for lentivirus vectors (see Kafri, T., et al. (1999) *J. Virol.* 73: 576-584; Dull, T., et al. (1998) *J. Virol.* 72: 8463-8471).

Recombinant herpes viruses, such as herpes simplex virus type I (HSV-1) have been used successfully to target DNA delivery to cells expressing the erythropoietin receptor (Laquerre, S., et al. (1998) *J. Virol.* 72: 9683-9697). These vectors can also be used to genetically alter the MAPCs, which the inventors have demonstrated to be stably transduced by a viral vector.

Adenoviral vectors have high transduction efficiency, can incorporate DNA inserts up to 8 Kb, and can infect both replicating and differentiated cells. A number of adenoviral vectors have been described in the literature and are known to those of skill in the art (see, for example, Davidson, B. L., et al. (1993) *Nature Genetics* 3: 219-223; Wagner, E., et al. (1992) *Proc. Natl. Acad. Sci. USA* 89: 6099-6103). Methods for inserting target DNA into an adenovirus vector are known to those of skill in the art of gene therapy, as are methods for using recombinant adenoviral vectors to introduce target DNA into specific cell types (Wold, W. (1998) *Humana Methods in Molecular Medicine*, Blackwell Science, Ltd.). Binding affinity for certain cell types has been demonstrated by modification of the viral vector fiber sequence. Adenovirus vector systems have been described which permit regulated protein expression in gene transfer (Molin, M., et al. (1998) *J. Virol.* 72: 8358-8361). A system has also been described for propagating adenoviral vectors with genetically modified receptor specificities to provide transductional targeting to specific cell types (Douglas, J., et al. (1999) *Nature Biotech.* 17: 470-475). Recently described ovine adenovirus vectors even address the potential for interference with successful gene transfer by preexisting humoral immunity (Hofmann, C., et al. (1999) *J. Virol.* 73: 6930-6936).

Adenovirus vectors are also available which provide targeted gene transfer and stable gene expression using molecular conjugate vectors, constructed by condensing plasmid DNA containing the target gene with polylysine, with the polylysine linked to a replication-incompetent adenovirus. (Schwarzenberger, P., et al. (1997) *J. Virol.* 71: 8563-8571.)

Alphavirus vectors, particularly the Sindbis virus vectors, are also available for transducing the cells of the present invention. These vectors are commercially available (Invitrogen, Carlsbad, Calif.) and have been described in, for example, U.S. Pat. No. 5,843,723, as well as by Xiong, C., et al. (1989) *Science* 243: 1188-1191; Bredenbeek, P. J., et al. (1993) *J. Virol.* 67: 6439-6446; and Frolov, I., et al. (1996) *Proc. Natl. Acad. Sci. USA* 93: 11371-11377.

The inventors have shown that MAPCs possess good transduction potential using the eGFP-MND lentiviral vector described by Robbins, et al. (*J. Virol.* (1997) 71(12): 9466-9474) and eGFP-MGF vector. Using this method, 30-50% of MAPC can be transduced after a short exposure of 4.6 hours to an enhanced green fluorescent protein (eGFP) vector containing supernatants made in PA3-17 packaging cells (an amphotropic packaging cell line derived from NIH 3T3 fibroblasts and described by Miller, A. D., and C. Buttimore (*Mol. Cell. Biol.* (1986) 6: 2895-2902), combined with protamine (8 mg/ml). Expression of eGFP persists throughout the culture of undifferentiated MAPCs. In addition, transfection using lipofectamine has been successfully used to introduce transgenes in MAPCs.

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells (Persons, D., et al. (1998) *Nature Medicine* 4: 1201-1205). Alternative selectable markers include the β-Gal gene, the truncated nerve growth factor receptor, and drug selectable markers (including but not limited to NEO, MTX, and hygromycin).

Any of these techniques can also be applied to introducing a transcriptional regulatory sequence into MAPCs to activate a desired endogenous gene. This can be done by both homologous (e.g., U.S. Pat. No. 5,641,670) or non-homologous (e.g., U.S. Pat. No. 6,602,686) recombination. These are incorporated by reference for teaching of methods of endogenous gene activation.

The present invention is additionally described by way of the following illustrative, non-limiting examples.

EXAMPLES

Example 1

Human MAPCs (from Bone Marrow Mononuclear Cells)

Bone marrow mononuclear cells were obtained from bone marrow aspirates from the posterior iliac crest of >80 healthy human volunteers. Ten to 100 cubic centimeters of bone marrow was obtained from each subject, as shown in Table 2, which indicates the approximate number of mononuclear cells isolated from each subject. Mononuclear cells ("MNCs") were obtained from bone marrow by centrifugation over a Ficoll-Paque density gradient (Sigma Chemical Co., St Louis, Mo.). Bone marrow MNCs were incubated with CD45 and Glycophorin A microbeads (Miltenyi Biotec, Sunnyvale, Calif.) for 15 minutes and $CD45^+GlyA^+$ cells removed by placing the sample in front of a SuperMACS magnet. The eluted cells are 99.5% $CD45^-GlyA^-$.

As shown in Table 2, depletion of $CD45^+GlyA^+$ cells resulted in recovery of $CD45^- GlyA^-$ cells which constituted approximately 0.05 to 0.10% of the total bone marrow mononuclear cells.

TABLE 2

Number of MAPCs in Human Bone Marrow Estimated by LDA

| Volume of Bone Marrow (cc) | Number of Mononuclear BM Cells Post Ficoll (in millions) | Number of $CD45^-$ $GlyA^-$ Cells Post-SuperMACS | Number of MAPCs (estimated by limiting dilution assay, LDA) |
|---|---|---|---|
| 50 | 100 | 100,000 | 50 |
| 25 | 80 | 60,000 | 35 |
| 25 | 50 | 14,000 | 10 |
| 50 | 100 | 50,000 | 30 |
| 10 | 150 | 75,000 | 30 |
| 30 | 100 | 100,000 | 25 |
| 25 | 80 | 75,000 | 35 |
| 100 | 190 | 78,000 | 25 |
| 100 | 150 | 60,000 | 15 |
| 100 | 160 | 160,000 | 85 |
| 100 | 317 | 400,000 | 50 |
| 100 | 200 | 150,000 | 70 |
| 50 | 160 | 160,000 | 85 |
| 50 | 115 | 150,000 | 70 |
| 25 | 60 | 60,000 | 30 |
| 100 | 307 | 315,000 | 100 |
| 100 | 216 | 140,000 | 80 |
| 50 | 130 | 150,000 | 40 |
| 100 | 362 | 190,000 | 60 |
| 50 | 190 | 150,000 | 40 |
| 100 | 200 | 185,000 | 100 |
| 100 | 387 | 300,000 | 170 |
| 50 | 100 | 130,000 | 20 |
| 150 | 588 | 735,000 | 300 |

Cells were selected that do not express the common leukocyte antigen CD45, or the erythroid precursor marker glycophorin-A (GlyA). $CD45^-GlyA^-$ cells constitute $1/10^3$ marrow mononuclear cells. $CD45^-GlyA^-$ cells were plated in wells coated with fibronectin in 2% FCS, EGF, PDGF-BB, dexamethasone, insulin, linoleic acid, and ascorbic acid. After 7-21 days, small clusters of adherent cells developed. Using limiting dilution assays, the frequency of cells giving rise to these adherent clusters is $1/5 \times 10^3$ $CD45^-GlyA^-$ cells.

When colonies appeared (about $10^3$ cells), cells were recovered by trypsinization and re-plated every 3-5 days at a 1:4 dilution under the same culture conditions. Cell densities were maintained between $2-8 \times 10^3$ cells/cm². Cell doubling time was 48-60 h. Immunophenotypic analysis by FACS of cells obtained after 10-12 cell doubling showed that cells did not express CD31, CD34, CD36, CD38, CD45, CD50, CD62E and CD62-P, Muc18, cKit, Tie/Tek, and CD44. Cells expressed no HLA-DR or HLA-class-I and expressed low levels of $\beta$2-microglobulin. Cells stained highly positive with antibodies against CD10, CD13, CD49b, CD49e, CDw90, and Flk1. The MAPC phenotype remained unchanged for >30 cell doublings (n=15). MAPC cultures with cells capable of proliferating beyond 30 cell doublings and differentiating to all mesodermal cell-types have been established from >85% of donors, age 2-50 years. In ten donors, we have expanded MAPCs for >50 cell doublings. When cells were cultured in serum-free medium, also supplemented with 10 ng/ml IGF, cell doubling was slower (>60 h), but >40 cell doublings could be obtained. As was seen for cells cultured with 2% FCS without IGF, cells cultured in serum-free medium were HLA-class-I and CD44 negative, and could differentiate into all mesodermal phenotypes.

When cells were plated on collagen-type-I or laminin instead of fibronectin, they expressed CD44 and HLA-DR, and could not be expanded beyond 30 cell doublings. When EGF or PDGF were omitted, cells did not proliferate and died. Increased concentrations of these cytokines allowed initial growth of MAPCs but caused loss of proliferation beyond 20-30 cell doublings. Addition of higher concentrations of dexamethasone also caused loss of proliferation beyond 30 cell doubling. When cells were cultured with >2% FCS in the culture medium, they expressed CD44, HLA-DR, and HLA-class-I. Likewise, culture at high density ($>8 \times 10^3$ cells/cm²) was associated with the acquisition of CD44, HLA-DR and HLA-class-I, and Muc-18. Culture at high density or with higher concentrations of FCS was also associated with loss of expansion capacity, and cells did not proliferate beyond 25-30 cell doublings.

MAPCs were replated at 1 cell/well once cultures had been established. From three donors, >2000 cells were plated singly in FN coated 96 well plates with the same culture medium. Cell growth was not detected. When cells were deposited at 10 cells/well, cell growth in approximately 4% of wells was detected. Progeny of 5% of these wells could be expanded to $>10^7$ cells.

Telomere length of MAPCs from five donors (age 2-50 years) cultured for 15 cell doublings was between 11-16 kb. In three donors, this was 3 kb longer than telomere length of blood lymphocytes obtained from the same donors. Telomere length of cells from one donor evaluated after 15 cell doublings, 30 cells doublings, and 45 cell doublings remained unchanged. Cytogenetic analysis of MAPCs recovered after 30 cell doublings showed a normal karyotype.

Example 2

Mouse MAPCs

All tissues were obtained according to guidelines from the University of Minnesota IACUC. BM mononuclear cells (BMMNC) were obtained by Ficoll Hypaque separation. BM was obtained from 5-6 week old ROSA26 mice or C57/BL6 mice. Alternatively, muscle and brain tissue was obtained from 3-day old 129 mice. Muscles from the proximal parts of fore and hind limbs were excised and thoroughly minced. The tissue was treated with 0.2% collagenase (Sigma Chemical Co., St Louis, Mo.) for 1 hour at 37° C., followed by 0.1% trypsin (Invitrogen, Grand Island, N.Y.) for 45 minutes. Cells were then triturated vigorously and passed through a 70 µm filter. Cell suspensions were collected and centrifuged for 10 minutes at 1600 rpm. Brain tissue was dissected and minced thoroughly. Cells were dissociated by incubation with 0.1% trypsin and 0.1% DNAse (Sigma) for 30 minutes at 37° C. Cells were then triturated vigorously and passed through a 70 µm filter. Cell suspensions were collected and centrifuged for 10 minutes at 1600 rpm.

BMMNC or muscle or brain suspensions were plated at $1\times10^5/cm^2$ in expansion medium [2% FCS in low glucose Dulbecco's minimal essential medium (LG-DMEM), 10 ng/ml each of platelet derived growth factor (PDGF), epidermal growth factor (EGF) and leukemia inhibitory factor (LW)] and maintained at $5\times10^3/cm^2$. After 3-4 weeks, cells recovered by trypsin/EDTA were depleted of $CD45^+GlyA^+$ cells with micromagnetic beads. Resulting $CD45^-GlyA^-$ cells were replated at 10 cells/well in 96 well plates coated with FN and were expanded at cell densities between 0.5 and $1.5\times10^3/cm^2$. The expansion potential of MAPCs was similar regardless of the tissue from which they were derived.

Murine MAPCs obtained after 46 to >80 PDs were tested by Quantitative (Q)-RT-PCR for expression levels of oct-4 and rex-1, two transcription factors important in maintaining an undifferentiated status of ES cells. RNA was extracted from mouse MAPCs, neuroectodermal differentiated progeny (day 1-7 after addition of bFGF) and mouse ES cells. RNA was reverse transcribed and the resulting cDNA underwent 40 rounds of amplification (ABI PRISM 7700, Perkin Elmer/Applied Biosystems) with the following reaction conditions: 40 cycles of a two step PCR (95° C. for 15 seconds, 60° C. for 60 seconds) after initial denaturation (95° C. for 10 minutes) with 2 µl of DNA solution, 1× TaqMan SYBR Green Universal Mix PCR reaction buffer. Primers are listed in Table 3.

TABLE 3

Primers Used

| | |
|---|---|
| NEO | 5'-TGGATTGCACGCAGGTTCT-3' |
| | 5'-TTCGCTTGGTGGTCGAATG-3' |
| Oct4 | 5'-GAAGCGTTTCTCCCTGGATT-3' |
| | 5'-GTGTAGGATTGGGTGCGTT-3' |
| Rex1 | 5'-GAAGCGTTCTCCCTGGAATTTC-3' |
| | 5'-GTGTAGGATTGGGTGCGTTT-3' |
| Otx1 | 5'-GCTGTTCGCAAAGACTCGCTAC-3' |
| | 5'-ATGGCTCTGGCACTGATACGGATG-3' |
| Otx2 | 5'-CCATGACCTATACTCAGGCTTCAGG-3' |
| | 5'-GAAGCTCCATATCCCTGGGTGGAAAG-3' |
| Nestin 5' | 5'-GGAGTGTCGCTTAGAGGTGC-3' |
| | 5'-TCCAGAAAGCCAAGAGAAGC-3' | mRNA levels were normalized using GAPDH as housekeeping gene, and compared with levels in mouse ES cells. Oct-4 and rex-1 mRNA were present at similar levels in BM, muscle, and brain derived MAPCs. Rex-1 mRNA levels were similar in mMAPCs and mES cells, while oct-4 mRNA levels were about 1,000 fold lower in MAPCs than in ES cells.

The Gene Expression Profiles of Mouse MAPCs from Bone Marrow, Muscle, and Brain are Highly Similar To further evaluate whether MAPCs derived from different tissues were similar, the expressed gene profiles of BM, muscle, and brain derived MAPCs were examined using U74A Affymetrix gene arrays. Briefly, mRNA was extracted from $2-3\times10^6$ BM, muscle, or brain derived-MAPCs cultured for 45 population doublings. Preparation of cDNAs, hybridization to the U74A arrays containing 6,000 murine genes and 6,000 EST clusters, and data acquisition were done per manufacturer's recommendations (all from Affymetrix, Santa Clara, Calif.). Data analysis was done using GeneChip® software (Affymetrix). Increased or decreased expression by a factor of 2.2 fold (Iyer, V. R. et al. (1999) *Science* 283: 83-7; Scherf, U. et al. (2000) *Nat. Biotech* 24: 236-44; Alizadeh, A. A. et al. (2000) *Nature* 403: 503-11) was considered significant. r2 value was determined using linear regression analysis.

Comparison between the expressed gene profiles of MAPCs from the three tissues showed that <1% of genes were expressed at >2.2-fold different levels in MAPCs from BM than muscle. Likewise, the expression of <1% of genes in BM derived MAPCs was >2.2-fold different than in brain derived MAPCs. As the correlation coefficient between the different MAPC populations was >0.975, it was concluded that MAPCs derived from the different tissues are highly homologous, in line with the phenotypic and differentiation characteristics described herein.

Using the mouse-specific culture conditions, mMAPC cultures have been maintained for more than 100 cell doublings. mMAPC cultures have been initiated with marrow from C57Bl/6 mice, ROSA26 mice, and C57BL/6 mice transgenic for HMG-LacZ.

Example 3

Rat MAPCs

BM and MNCs from Sprague Dawley, Lewis, or Wistar rats were obtained and plated under conditions similar to those described for mMAPCs. After 21-28 days, cells were depleted of $CD45^+$ cells, and the resulting $CD45^-$ cells were subcultured at 10 cells/well.

Similar to mMAPCs, rMAPCs have been culture expanded for >100 PDs. Expansion conditions for rat MAPC culture required the addition of EGF, PDGF-BB, and LW, and culture on FN, but not collagen type I, laminin, or Matrigel™.

Rat MAPCs that had undergone 42 PDs, 72 PDs, 80 PDs, and 100 PDs, were harvested and telomere lengths evaluated. Telomeres did not shorten in culture, as determined by Southern blot analysis after 42 PDs, 72 PDs, 80 PDs, and 100 PDs. Monthly cytogenetic analysis of rat MAPCs revealed normal karyotype.

Example 4

Clonality of Mouse and Rat MAPCs

To demonstrate that differentiated cells were single cell-derived and MAPCs are indeed "clonal" multipotent cells, cultures were made in which MAPCs had been transduced with a retroviral vector. Undifferentiated MAPCs and their progeny were found to have the retrovirus inserted in the same site in the genome.

Studies were done using two independently derived ROSA26 MAPCs, two C57BL/6 MAPCs, and one rMAPC population expanded for 40 to >90 PDs, as well as with the eGFP transduced "clonal" mouse and "clonal" rMAPCs. No differences were seen between eGFP transduced and untransduced cells. Of note, eGFP expression persisted in differentiated MAPCs.

Specifically, murine and rat BMMNCs cultured on FN with EGF, PDGF-BB, and LIF for three weeks were transduced on two sequential days with an eGFP oncoretroviral vector. Afterwards, $CD45^+$ and $GlyA^+$ cells were depleted and cells sub-cultured at 10 cells/well. eGFP-transduced rat BMMNCs were expanded for 85 PDs. Alternatively, mouse MAPCs expanded for 80 PDS were used. Subcultures of undifferentiated MAPCs were generated by plating 100 MAPCs from cultures maintained for 75 PDs and re-expanding them to $>5\times10^6$ cells. Expanded MAPCs were induced to differentiate in vitro to endothelium, neuroectoderm, and endoderm. Lineage differentiation was shown by staining with antibodies specific for these cell types.

Example 5

Human MAPCs are not Immunogenic

Mesenchymal stem cells have demonstrated low in vitro immunogenicity and the ability to engraft across allogeneic recipients (Di Nicola, M. et al. (2002) *Blood* 99: 3838-3843; Jorgensen, C. et al. (2002) *Gene Therapy* 10: 928-931; Le Blanc, K. et al. (2003) *Scandinavian Journal of Immunology* 57: 11-20; McIntosh, K. et al. (2000) *Graft* 6: 324-328; Tse, W. et al. (2003) *Transplantation* 75: 389-397).

Figure 1:
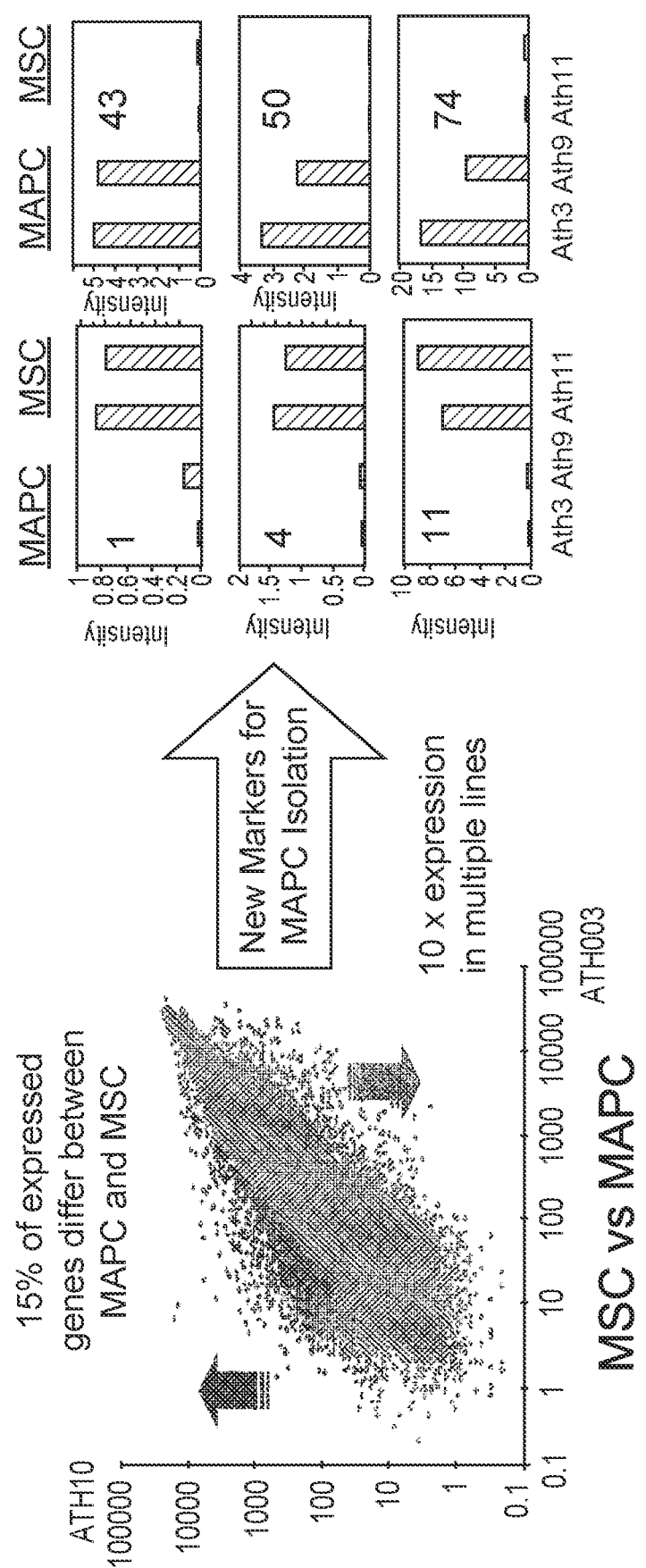
Figure 2:
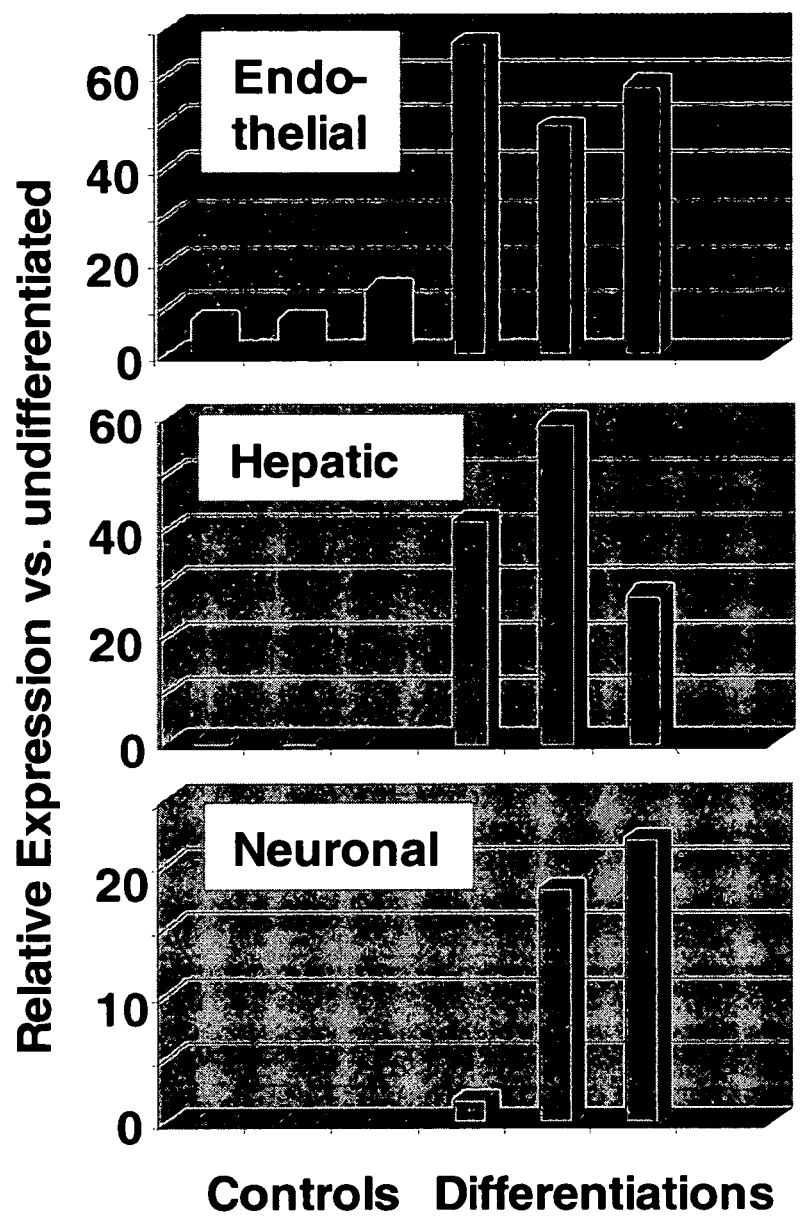
Figure 3:
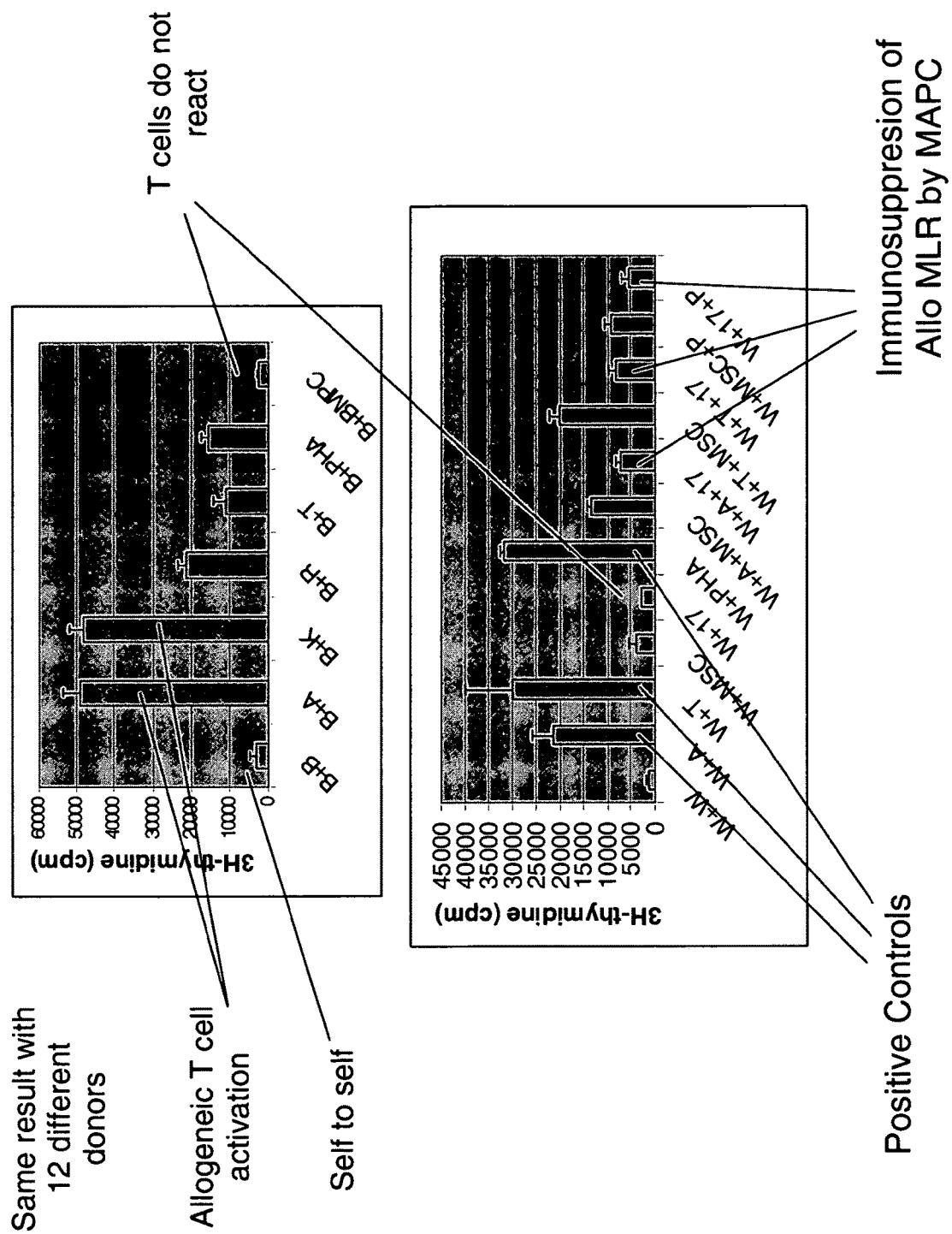

FIG. 3 shows that human MAPCs exhibit low in vitro immunogenicity and are immunosuppressive when added to otherwise potent T-cell MLRs (Tse, W. et al. (2003)). Results were consistent across all donor and responder pairs tested.

Responder and stimulator cells were prepared for these experiments and the MLRs were performed according to the procedures described by Tse, W. et al. (2003).

Example 6

MAPCs Modulate T-Cell Responses

The ability of MAPCs to modulate, and in this case suppress, immune responsiveness is illustrated by T-cell proliferation assays, for example, which can be carried out as follows.
Preparation of Responder T-Cells
Responder cells were prepared from lymph nodes of Lewis rats. Lymph nodes were surgically removed from the rats and immediately placed into 3 to 5 ml of media (complete RPMI or complete DMEM) in 60×15 mm Petri plates. The lymph nodes were dispersed through a nylon filter (using the hand plunger of a syringe). The dispersions were loaded into 50 ml tubes and centrifuged at 1,250 rpm for 8 minutes. The resulting supernatants (media) were discarded. The pellets (containing the cells) were resuspended in fresh media (complete RPMI or complete DMEM). The cells were washed three times, and then resuspended in fresh media. Resuspended cell densities were determined by counting the number of cells in a known volume thereof. The cells were maintained on ice. Prior to use, the cells were resuspended in media (complete RPMI or complete DMEM) at a density of $1.25\times10^6$ cells/ml.
Preparation of MAPCs
MAPCs were prepared from Lewis or from Sprague-Dawley rats and then frozen as described above. They were thawed and then irradiated at 3000 rad. The irradiated cells were then resuspended in media (complete RPMI or complete DMEM) to densities of $0.4\times10^6$ cells/ml, $0.8\times10^6$ cells/ml, and $1.6\times10^6$ cells/ml.

Preparation of Concanavalin A
Concanavalin A ("ConA") was used to activate the T-cells. The ConA was dissolved in PBS (complete RPMI or complete DMEM) to final concentrations of 0 (PBS only) 10, 30, and 100 µg/ml.
Assay Procedure
Each data point is based on at least three determinations.
20 µl of each of the ConA solutions was added to wells of microtiter plates (96 well, flat bottom), followed by 80 µl/well of the responder cells and 100 µl/well of the MAPCs. The plates were incubated at 37° C. in humidified incubators under 5% $CO_2$ for 4-5 days. The plates were pulsed with 1 µCi/well $^3$H-thymidine during the last 14-18 hours of culture. Thereafter, the cells were automatically harvested on glass fiber filters using a Tomtec harvesting machine. The thymidine uptake was quantified in a micro-plate scintillation counter. Results were expressed as mean counts per minute (CPM)+/−SD.

Final concentrations of ConA in the growth media in the wells were 0, 1, 3.16, and 10 µg/ml. MAPCs were present in the wells in the amounts of 0, 0.4, 0.8, and $1.6\times10^5$ cells/well.

The results, described below, are illustrated in FIG. 4.
Results
Increasing amounts of ConA resulted in a dose-dependent stimulation of T-cell proliferation (FIG. 4, LN only). Lewis MAPCs inhibited proliferation of the ConA stimulated T-cells. The inhibition depended on the dose of MAPCs. The maximum inhibition, 50%, occurred at the highest dose of MAPCs used in these experiments and with low and intermediate doses of ConA. These results are displayed graphically in FIG. 4 and show that MAPCs suppress the proliferation of activated T-cells.

Example 7

MAPCs Suppress Proliferation of Stimulated T-Cells

The ability of MAPCs to suppress proliferation of syngeneic and non-matched (allogeneic) T-cell proliferative responses is demonstrated by the results of mixed lymphocyte reactions. The example below shows the suppressive effects of MAPCs on T-cells from Lewis rats stimulated by splenocytes from irradiated DA rats. MAPCs from syngeneic Lewis rats and non-matched (allogeneic) Sprague-Dawley rats both inhibited T-cell responses in a dose-dependent manner. The experiments were carried out as follows.
Preparation of Responder T-Cells
Responder cells were prepared from the lymph nodes of Lewis rats as described above.
Irradiated Spleen Stimulator Cells
Spleens were surgically removed from DA rats. Splenocytes then were isolated from the spleens essentially as described above for the isolation of responder cells from the lymph nodes of Lewis rats. The isolated spleen cells were irradiated at 1800 rad. The cells then were resuspended to $4\times10^6$/ml and kept on ice until they were used.
Preparation of MAPCs
Syngeneic MAPCs were prepared from Lewis rats as described above. Non-matched (allogeneic) MAPCs were prepared from Sprague-Dawley rats in the same way. Both Lewis and Sprague-Dawley MAPCs were irradiated at 3000 rad, then resuspended in complete RPMI media at densities of $0.03\times10^6$/ml, $0.06\times10^6$/ml, $0.125\times10^6$/ml, $0.25\times10^6$/ml, $0.5\times10^6$/ml, $1\times10^6$/ml, and $2\times10^6$/ml.

Assay Procedure 96 well microtiter plate wells were loaded with: 100 µl of MAPCs (at the dilutions indicated above) or 100 µl of media; 50 µl of a stimulator cell stock or control; 50 µl each of a responder cell stock or control; and media (complete RPMI or complete DMEM) as required to equalize total volumes to a final volume of 200 µl/well. 96 well flat bottom microtiter plates were used for all assays.

Each data point is based on at least three determinations.

The plates were incubated at 37° C. in humidified incubators under 5% $CO_2$ for 4-5 days. The plates were pulsed with 1 µCi/well $^3$H-thymidine during the last 14-18 hours of culture. Thereafter, the cells were automatically harvested on glass fiber filters using a Tomtec harvesting machine. The thymidine uptake was quantified in a micro-plate scintillation counter. Results were expressed as mean counts per minute (CPM)+/−SD.

Results

Figure 5B:
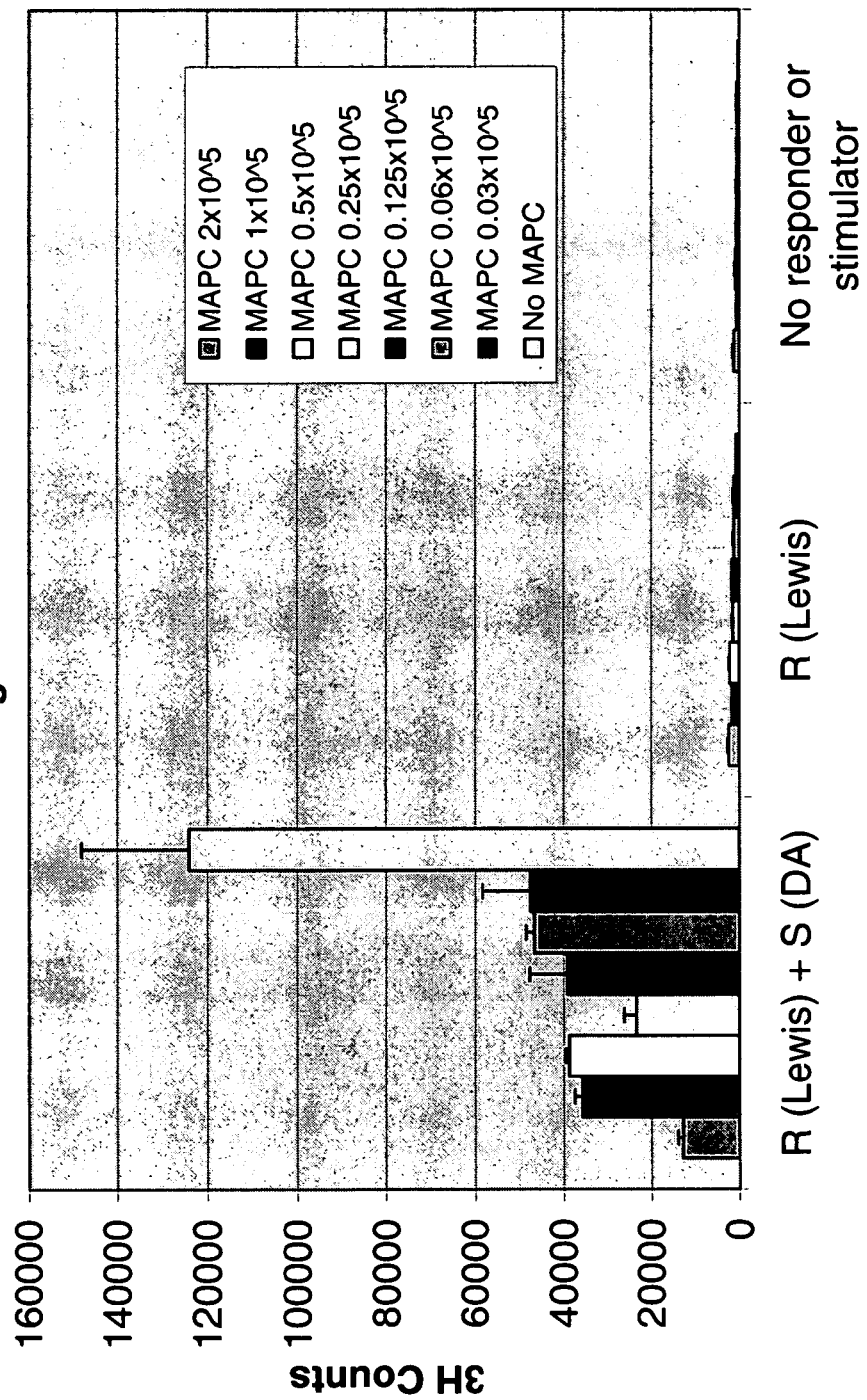
FIG. 5B is a chart showing the immunosuppressive effects of Sprague-Dawley MAPCs in mixed lymphocyte reactions, as described in Example 7. Captions and abbreviations are the same as in FIG. 5A.

Exposure of T-cells derived from the lymph nodes of Lewis rats (Responders) to stimulator cells consisting of irradiated splenocytes from DA rats (Stimulators) resulted in very robust proliferative responses of responder cells, as shown in FIGS. 5A and 5B, for "no MAPC".

Addition of increasing doses of syngeneic Lewis MAPCs (FIG. 5A) and non-matched (allogeneic) third-party Sprague-Dawley MAPCs (FIG. 5B) resulted in a significant and dose-dependent inhibition of T-cell activation. Maximal levels of inhibition were ~80%. Even at the lowest doses of MAPCs, there was 40-50% inhibition.

There was no $^3$H-thymidine incorporation in the controls, showing that incorporation was due solely to proliferation of activated responder T-cells, as shown in FIGS. 5A and 5B.

In summary, the results show that syngeneic and third-party (allogeneic) MAPCs suppress T-cell proliferation even in the presence of potent activator splenocytes from non-matched rats. In these experiments, inhibition peaked when there were similar numbers (200,000 cells) each of stimulators, responders, and MAPCs in the reaction. Under these conditions, there was ~80% inhibition. There was very substantial inhibition at much lower ratios of MAPCs to the other cells in the reaction. For instance, at 1.5% MAPCs, there was 50% inhibition (3,000 MAPCs versus 200,000 of each of the types of cells). The results demonstrate not only that MAPCs have a strong immunosuppressive effect, but also that a relatively small number of MAPCs is sufficient to inhibit a relatively large number of competent T-cells even in the presence of very potent T-cell activators.

Example 8

MAPCs are Safe

The main immediate risk of intravenous injection of large numbers of cells is the accumulation of cell clumps in the lungs which results in respiratory distress and can cause cardiac arrest. To show the safety of MAPCs in this regard, we measured the effects of intravenous injection of MAPCs on respiratory rates in Buffalo rats.

MAPCs were prepared from Lewis rats as described above ("Lewis MAPCs"). Splenocytes also were prepared from Lewis rats as described above for use as controls ("Lewis Splenocytes").

One female Lewis rat served as the splenocyte donor for each group (experimental condition). Two female Buffalo rats were used as recipients for each group (experimental condition).

The cells were administered to the rats as indicated below. The data are displayed graphically in FIG. 6. The concordance of data points to the individual rats as numbered below is enumerated in the vertical legend at the right of FIG. 6. All rats were Buffalo rats.

| | |
|---|---|
| 1.1, 1.2 | $10 \times 10^6$ Lewis MAPC per rat |
| 2.1, 2.2 | $5 \times 10^6$ Lewis MAPC per rat |
| 3.1, 3.2 | $2.5 \times 10^6$ Lewis MAPC per rat |
| 4.1, 4.2 | $1.2 \times 10^6$ Lewis MAPC per rat |
| 5.1, 5.2 | $10 \times 10^6$ Lewis Splenocytes per rat |
| 6.1, 6.2 | $5 \times 10^6$ Lewis Splenocytes per rat |
| 7.1, 7.2 | $2.5 \times 10^6$ Lewis Splenocytes per rat |
| 8.1, 8.2 | $1.2 \times 10^6$ Lewis Splenocytes per rat |

As indicated above, rats were injected with 1.2, 2.5, 5, or 10 million MAPCs or 1.2, 2.5, 5, or 10 million splenocytes. This corresponded to 5, 10, 25, or 50 million cells/kg. Respiratory rates were measured before (0 min) and at 1, 5, and 10 min after intravenous injection of the MAPCs or splenocytes. Respiratory rates were measured for 20 seconds and the counts were multiplied by 3 to derive the per minute respiratory rates. Normal rat respiratory rates are between 60 and 140/min.

Results

Figure 6:
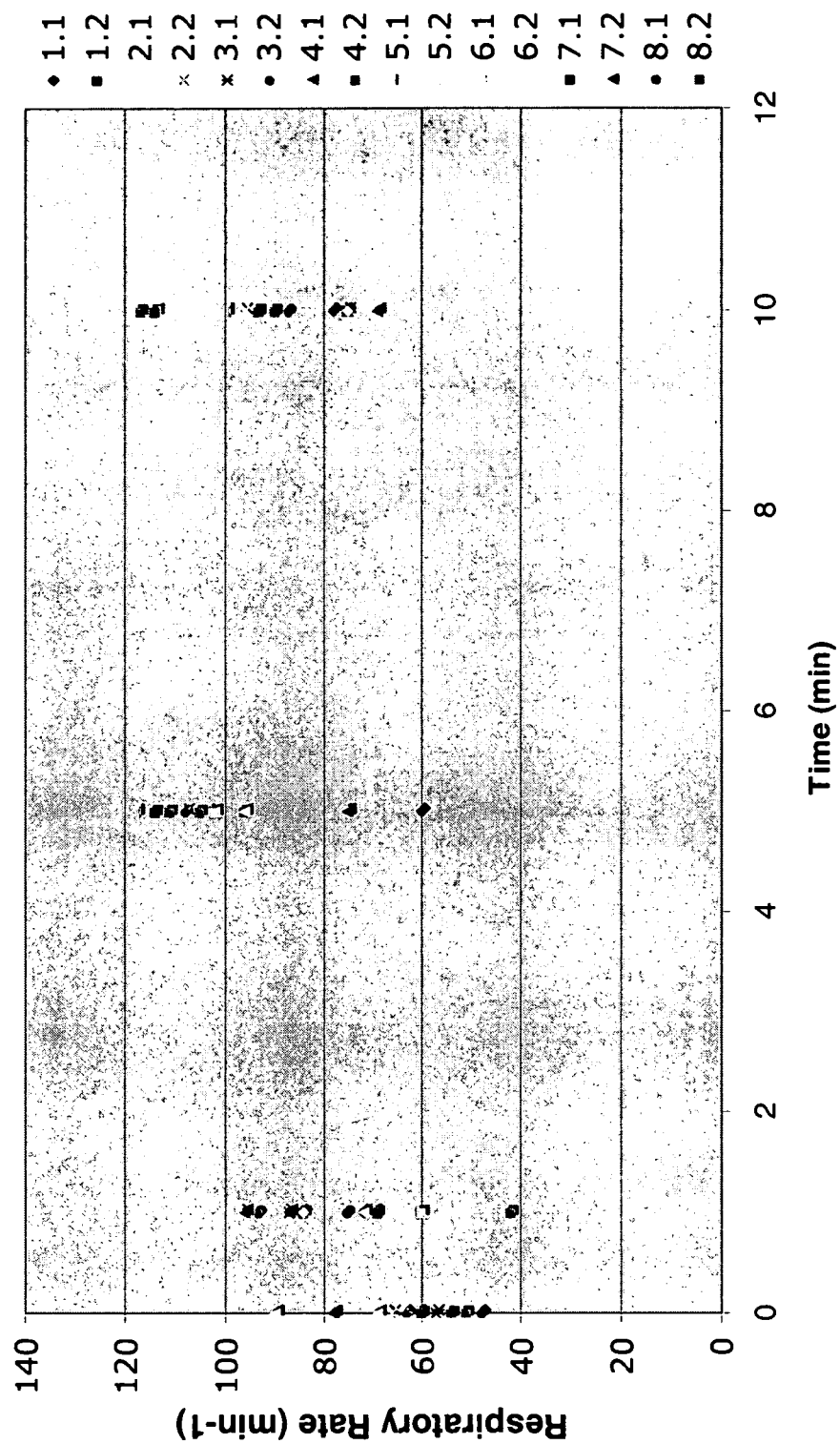
FIG. 6 is a graph showing that infusion of MAPCs does not adversely affect the health of recipients as determined by their respiratory rate. The graph is further described in Example 8.

All animals survived after intravenous cell injections. No significant differences or trends were observed in the respiratory rates under the different conditions. The results are shown in FIG. 6. Initial respiratory rates (0 min) were slightly reduced because the animals were anesthetized before the cells were injected. At each time-point, measurements were clustered without any apparent trends.

In summary, intravenous injection of 5-50 million MAPCs/kg did not cause changes in respiratory rates or mortality in any of the rats under any of the conditions. The results show that intravenous injection of MAPCs is safe even at high doses.

Example 9

MAPC Expression of Immune Markers

The immunomodulatory nature of MAPCs was further characterized by determining immune regulatory markers in MAPCs, such as those described by Barry et al. (2005). The markers were determined using marker-specific antibodies and FACS analysis.

Rat bone marrow MAPCs were isolated, cultured, and harvested as described above. For FACS analysis, the cells were suspended at $1-2 \times 10^8$ cells/ml in PBS. 200 µl of the cell suspension was added to each of a series of 12×75 polypropylene tubes. A marker-specific antibody or a control was added to each of the tubes, and they were then incubated for 15-20 minutes at room temperature. At the end of the incubation period, 2 ml of PBS was added to each tube and they were then centrifuged at 400×g for 5 minutes. Supernatants were discarded and the cells were resuspended in each tube in 100 µl of PBS. A fluorescent labeled secondary antibody was added to each tube in an appropriate volume, and the tubes were again incubated for 15-20 minutes at room temperature, this time in the dark. Thereafter, 2 ml of PBS was added to each tube and they were again centrifuged at 400×g for 5 minutes. Supernatants were discarded, and the cells in each tube were resuspended in 200 µl of PBS and were then kept on ice until analyzed by FACS.

Results are enumerated and presented graphically in Table 4. As shown in the table, rat MAPCs are: (a) positive for MHC class I, CD11c, CD29, and CD90, and (b) negative for MHC class II, CD11b, CD31, CD40, CD45, CD54, CD80, CD86, CD 95, and CD106. Negative results were validated for each antibody by positive staining of control cells, including rat peripheral blood and endothelial cells. These patterns of marker expression, as to both the markers that are detected in MAPCs and those that were not detected, are fully consistent with the low immunostimulatory cross-section of MAPCs.

TABLE 4

Detection of Immune Cell-Related Markers in MAPCs

| Marker | Name/Function of Marker | Commercial Anti-Rat-Marker Antibody | FACS Detection |
|---|---|---|---|
| MHC class I | | yes | Positive |
| MHC class II | | yes | Negative |
| CD11b | Mac-1 | yes | Negative |
| CD11c | Integrin αX | yes | Positive |
| CD29 | Integrin β1 | yes | Positive |
| CD31 | PECAM-1 | yes | Negative |
| CD40 | TNFRSF | yes | Negative |
| CD45 | Leucocyte common antigen | yes | Negative |
| CD54 | ICAM-1 | yes | Negative |
| CD80 | B7-1 | yes | Negative |
| CD86 | B7-2 | yes | Negative |
| CD90 | Thy-1 | yes | Positive |
| CD95 | Apo-1 | yes | Negative |
| CD106 | VCAM-1 | yes | Negative |

Example 10

MAPCs Suppress Previously Stimulated T-Cells in MLRs Cells

Responder cells were prepared from the lymph nodes of Lewis rats as described above. Splenocytes, prepared from Buffalo or DA rats, as described above, were used as stimulators. MAPCs were prepared as described above.

Procedures

MAPCs were added to a first group of MLRs at the same time as splenocytes (as was done in the foregoing examples). In addition, MAPCs were added to a second group of MLRs that were set-up identically to the first group. However, the MAPCs in the second group were added 3 days after the addition of the splenocytes (or control). Thus, in the first group, MAPCs were added before the T-cells began proliferating in response to the splenocytes. In the second group, the MAPCs were added when the T-cell response to the splenocytes had been underway for 3 days. All plates were incubated for a total of 4 days, then pulsed with $^3$H-thymidine and harvested, as described in the foregoing examples. The experiments otherwise were carried out as described for the MLRs in the foregoing examples.

Each data point is based on at least three determinations.

Results

As can be seen from the right side of FIG. 7, MAPCs strongly suppress T-cell proliferation in MLRs when they are added three days after stimulation by allogeneic splenocytes. Comparison of the left and right sides of FIG. 7 shows that MAPCs strongly suppress the on-going proliferation reaction. Quantitatively, the results show for Buffalo cells that MAPCs added 3 days post-stimulation suppressed T-cell proliferation 50% compared to controls (right side of the figure), and 75% when added at the same time as the stimulatory splenocytes (left side of the figure). Similarly, for DA cells, MAPCs added 3 days post-stimulation suppressed T-cell proliferation 33% compared to controls (right side of the figure), and 70% when added at the same time as the stimulatory splenocytes (left side of the figure).

In all cases, the degree of immunosuppression by MAPCs depended, in general, on the number of MAPCs that were added to the reaction. In other words, immunosuppression depended on the dose of MAPCs added to the MLRs.

Publications cited above are incorporated herein by reference in their entirety as to specific subject matter for which they have been cited.

What is claimed is:

1. A method of ameliorating an immune dysfunction in a subject; comprising administering to human subject mammalian multipotent adult progenitor cells characterized in that: they are not embryonic stem cells, embryonic germ cells, or germ cells, are allogeneic to the subject, express telomerase, have a normal karyotype, and have undergone at least 10-40 cell doublings in culture, wherein the cells are administered adjunctively to one or more other treatments wherein the cells have not been genetically engineered to improve their immunological properties, and wherein said immune dysfunction is not GVHD and is not diabetes.

2. A method according to claim 1, wherein said progenitor cells can differentiate into cells of at least two of the endodermal, ectodermal, and mesodermal embryonic lineages.

3. A method according to claim 1, wherein said progenitor cells are derived from cells isolated from any of placental tissue, umbilical cord tissue, umbilical cord blood, bone marrow, blood, spleen tissue, thymus tissue, spinal cord tissue, adipose tissue, and liver tissue.

4. A method according to claim 1, wherein said progenitor cells are administered to said subject in one or more doses comprising $10^4$ to $10^8$ of said cells per kilogram of the subject's mass.

5. A method according to claim 4, wherein said progenitor cells are administered to the subject in one or more doses comprising $10^6$ to $10^7$ of said progenitor cells per kilogram of the subject's mass.

6. A method according to claim 1, wherein in addition to said progenitor cells, one or more growth factors, differentiation factors, signaling factors, and/or factors that increase homing are administered to said subject.

7. A method according to claim 1, wherein further any combination of one or more of each of the following is administered to said subject: an antibiotic agent, an anti-fungal agent, and/or an anti-viral agent.

8. A method according to claim 1, wherein said progenitor cells are administered in a formulation comprising one or more other pharmaceutically active agents.

9. A method according to claim 8, wherein said formulation further comprises any combination of one or more of: an antibiotic agent, an anti-fungal agent, and/or an anti-viral agent.

10. A method according to claim 1, wherein said progenitor cells are administered to the subject by a parenteral route.

11. A method according to claim 10, wherein said progenitor cells are administered by intravenous infusion.

12. A method according to claim 2, wherein said progenitor cells are derived from cells isolated from any of placental tissue, umbilical cord tissue, umbilical cord blood, bone marrow, blood, spleen tissue, thymus tissue, spinal cord tissue, adipose tissue, and liver tissue.

13. A method according to claim 2, wherein said progenitor cells are administered to said subject in one or more doses comprising $10^4$ to $10^8$ of said cells per kilogram of the subject's mass.

14. A method according to claim 13, wherein said progenitor cells are administered to the subject in one or more doses comprising $10^6$ to $10^7$ of said progenitor cells per kilogram of the subject's mass.

15. A method according to claim 2, wherein in addition to said progenitor cells, one or more growth factors, differentiation factors, signaling factors, and/or factors that increase homing are administered to said subject.

16. A method according to claim 2, wherein further any combination of one or more of each of the following is administered to said subject: an antibiotic agent, an anti-fungal agent, and/or an anti-viral agent.

17. A method according to claim 2, wherein said progenitor cells are administered in a formulation comprising one or more other pharmaceutically active agents.

18. A method according to claim 2, wherein said formulation further comprises any combination of one or more of: an antibiotic agent, an anti-fungal agent, and/or an anti-viral agent.

19. A method according to claim 2, wherein said progenitor cells are administered to the subject by a parenteral route.

20. A method according to claim 2, wherein said progenitor cells are administered by intravenous infusion.

21. A method according to any of claims 1, 2, 3 and 4 to 20, where said cells are derived from bone marrow.

22. A method according to any of claims 1, 2, 3 and 4 to 20, wherein said progenitor cells are human cells.

23. A method according to 22, wherein said progenitor cells are derived from human bone marrow.

* * * * *